(12) United States Patent
Schmitt et al.

(10) Patent No.: US 11,370,810 B2
(45) Date of Patent: Jun. 28, 2022

(54) METHODS AND COMPOSITIONS FOR PREPARING NUCLEIC ACIDS THAT PRESERVE SPATIAL-PROXIMAL CONTIGUITY INFORMATION

(71) Applicant: ARIMA GENOMICS, INC., San Diego, CA (US)

(72) Inventors: Anthony Schmitt, Poway, CA (US); Catherine Tan, San Francisco, CA (US); Derek Reid, San Diego, CA (US); Chris De La Torre, Aliso Viejo, CA (US); Siddarth Selvaraj, San Diego, CA (US)

(73) Assignee: ARIMA GENOMICS, INC., San Diego, CA (US)

( * ) Notice: Subject to any disclaimer, the term of this patent is extended or adjusted under 35 U.S.C. 154(b) by 204 days.

(21) Appl. No.: 16/689,002

(22) Filed: Nov. 19, 2019

(65) Prior Publication Data

US 2020/0157130 A1 May 21, 2020

Related U.S. Application Data

(60) Provisional application No. 62/785,643, filed on Dec. 27, 2018, provisional application No. 62/770,135, filed on Nov. 20, 2018.

(51) Int. Cl.
*C07H 1/00* (2006.01)
*C07H 21/04* (2006.01)

(52) U.S. Cl.
CPC .............. *C07H 1/00* (2013.01); *C07H 21/04* (2013.01)

(58) Field of Classification Search
CPC ....... C12N 15/1003; C07H 21/04; C07H 1/00
See application file for complete search history.

(56) References Cited

U.S. PATENT DOCUMENTS

| | | |
|---|---|---|
| 8,071,296 B2 | 12/2011 | Ruan et al. |
| 8,642,295 B2 | 2/2014 | De Laat et al. |
| 9,273,309 B2 | 3/2016 | Dekker et al. |
| 9,434,985 B2 | 9/2016 | Dekker et al. |
| 9,708,648 B2 | 7/2017 | Dekker et al. |
| 2011/0287947 A1 | 11/2011 | Chen et al. |
| 2017/0362649 A1 | 12/2017 | Lieberman-Aiden et al. |

FOREIGN PATENT DOCUMENTS

| | | |
|---|---|---|
| WO | WO 2015/010051 A1 | 1/2015 |
| WO | WO 2017/004612 A1 | 1/2017 |
| WO | WO 2017/197300 A1 | 11/2017 |
| WO | WO 2020/106776 A2 | 5/2020 |

OTHER PUBLICATIONS

Belton et al., Methods, 2012, 58, p. 268-276. (Year: 2012).*
Acemel et al., Gene, 2021, 767, 145185, 5 pages. (Year: 2021).*
International Search Report and Written Opinion dated Jun. 29, 2020 in PCT Application No. PCT/US2019/062298, filed on Nov. 19, 2019 and published as WO 2020/106776 on May 28, 2020, 22 pages.
4 Methods for Extracting DNA from FFPE Tissue Samples, Geneticist, Oct. 26, 2017, 4 pages.
Adey et al., "In Vitro, Long-Range Sequence Information for De Novo Genome Assembly via Transposase Contiguity", Genome Research, 2014, 24:2041-2049.
Amatori et al., "Epigenomic Profiling of Archived FFPE Tissues by Enhanced PAT-ChIP (EPAT-ChIP) Technology", Clinical Epigenetics, 2018, 10:143:15 pages.
Amini et al., "Haplotype-resolved Whole-Genome Sequencing by Contiguity-Preserving Transposition and Combinatorial Indexing", Nature Genetics, Dec. 2014, 46(12):1343-1349.
Anonymous, "In situ Hi-C Experimental Standards of the ENCODE Consortium", Retrieved from the Internet: URL: https://www.encodeproject.org/documents/f3ec6a89-4cde-4b0d-9da4-50d35b7f023b/@@download/attachment/final_in_situ_hi_c_experimental_standards_of_the_encode_consortium.pdf, Jan. 21, 2018, 3 pages.
Chakraborty et al., "Identification of Copy Number Variations and Translocations in Cancer Cells from Hi-C Data", Bioinformatics, 2018, 34(2):338-345.
Comet et al., "A Chromatin Insulator Driving Three-Dimensional Polycomb Response Element (PRE) Contacts and Polycomb Association with the Chromatin Fiber", Proceedings of the National Academy of Sciences, Feb. 8, 2011, 108(6):2294-2299.
Dekker et al., "Capturing Chromosome Conformation", Science, Feb. 15, 2002, 295(5558):1306-1311.
Dixon et al., "Integrative Detection and Analysis of Structural Variation in Cancer Genomes", Nature Genetics, Oct. 2018, 50(10):1388-1398.
Do et al., "Sequence Artifacts in DNA from Formalin-Fixed Tissues: Causes and Strategies for Minimization", Clinical Chemistry, 2015, 61 (1):64-71.
Dostie et al., "Chromosome Conformation Capture Carbon Copy (5C): A Massively Parallel Solution for Mapping Interactions Between Genomic Elements", Genome Research, Oct. 2006, 16(10):1299-1309.
Duan et al., "A Genome-Wide 3C-Method for Characterizing the Three-Dimensional Architectures of Genomes", Methods, 2012, 58:277-288.
Einaga et al., "Assessment of the Quality of DNA From Various Formalin-Fixed Paraffin-Embedded (FFPE) Tissues and the Use of This DNA for Next-Generation Sequencing (NGS) With No Artifactual Mutation", PLoS One, e0176280, May 12, 2017, 12(5):18 pages.

(Continued)

*Primary Examiner* — Jonathan S Lau
(74) *Attorney, Agent, or Firm* — Grant IP, Inc.

(57) ABSTRACT

Provided herein are methods and compositions for preparing nucleic acids in samples that preserve spatial-proximal contiguity information. Samples include, but are not limited to, formalin-fixed paraffin-embedded (FFPE) samples, deeply formalin-fixed samples and samples that comprise protein:cfDNA complexes.

12 Claims, 32 Drawing Sheets

(56) References Cited

OTHER PUBLICATIONS

Engreitz et al., "Three-Dimensional Genome Architecture Influences Partner Selection for Chromosomal Translocations in Human Disease", PLoS One, 2012, 7(9):10 pages.
Fanelli et al., "Chromatin Immunoprecipitation and High-Throughput Sequencing from Paraffin-Embedded Pathology Tissue", Nature Protocols, 2011, 6(12):1905-1909.
Fanelli et al., "Pathology Tissue-Chromatin Immunoprecipitation, Coupled with High-Throughput Sequencing, Allows the Epigenetic Profiling of Patient Samples", Proceedings of the National Academy of Sciences, Dec. 14, 2010, 107(50): 21535-21540.
Fang et al., "Mapping of Long-Range Chromatin Interactions by Proximity Ligation-Assisted ChIP-seq", Cell Research, 2016, 26:1345-1348.
Foley et al., "Gene Expression Profiling of Single Cells from Archival Tissue with Laser-Capture Microdissection and Smart-3SEQ", Genome Research, Sep. 13, 2019, 29:1816-1825.
Gavrilov et al., "Chromosome Conformation Capture (From 3C to 5C) and Its ChIP-Based Modification", Methods in Molecular Biology, 2009, 567:171-188.
Golloshi et al., "Iteratively Improving Hi-C Experiments One Step at a Time", bioRxiv, Mar. 22, 2018, 49 pages.
Harewood et al., "Hi-C as a Tool for Precise Detection and Characterisation of Chromosomal Rearrangements and Copy Number Variation in Human Tumours", 2017, 18(125):11 pages.
Hughes et al., "Analysis of Hundreds of Cis-Regulatory Landscapes at High Resolution in a Single, High-Throughput Experiment", Nature Genetics, Feb. 2014, 46(2):205-212.
Jager et al., "Capture Hi-C Identifies the Chromatin Interactome of Colorectal Cancer Risk Loci", Nature Communications, Feb. 19, 2015, 6(6178):9 pages.
Kalhor et al., "Genome Architectures Revealed by Tethered Chromosome Conformation Capture and Population-Based Modeling", Nature Biotechnology, Dec. 25, 2011, 30(1):90-98.
Kennedy-Darling et al., "Measuring the Formaldehyde Protein-DNA Cross-Link Reversal Rate", Analytical Chemistry, 2014, 86:5678-5681.
Lai et al., "Trac-Looping Measures Genome Structure and Chromatin Accessibility", Nature Methods, Sep. 2018, 15:741-747.
Lehmann-Werman et al., "Identification of Tissue-Specific Cell Death Using Methylation Patterns of Circulating DNA", Proceedings of the National Academy of Sciences, Mar. 29, 2016, 113(13): E1826-1834.
Li et al., "Simultaneous Profiling of DNA Methylation and Chromatin Architecture in Mixed Populations and in Single Cells", bioRxiv, 2018, 35 pages.
Lieberman-Aiden et al., "Comprehensive Mapping of Long-Range Interactions Reveals Folding Principles of the Human Genome", Science, Oct. 2009, 326(5950):289-293.
Lister et al., "Human DNA Methylomes at Base Resolution Show Widespread Epigenomic Differences", Nature, Nov. 19, 2009, 462(7271):315-322.
Mumbach et al., "HiChIP: Efficient and Sensitive Analysis of Protein-Directed Genome Architecture", Nature Methods, Nov. 2016, 13(11):919-922.
Nagano et al., "Comparison of Hi-C Results Using in-Solution Versus In-Nucleus Ligation", Genome Biology, 2015, 16(175):13 pages.
Nagano et al., "Single Cell Hi-C Reveals Cell-To-Cell Variability in Chromosome Structure", Nature, Oct. 3, 2013, 502(7469):59-64.
Oud et al., "Extraction of Nuclei from Selected Regions in Paraffin-Embedded Tissue", Cytometry, 1986, 7:595-600.
Paternoster et al., "A New Method to Extract Nuclei from Paraffin-Embedded Tissue to Study Lymphomas Using Interphase Fluorescence in Situ Hybridization", The American Journal of Pathology, Jun. 2002, 160(6):1967-1972.
Rao et al., "A 3D Map of the Human Genome at Kilobase Resolution Reveals Principles of Chromatin Looping", Cell, Dec. 18, 2014, 159:1665-1680.
Schultz et al., "Human Body Epigenome Maps Reveal Noncanonical DNA Methylation Variation", Nature, Jul. 9, 2015, 523(7559):212-216.
Selvaraj et al., "Complete Haplotype Phasing of the MHC And KIR Loci with Targeted Haploseq", BMC Genomics, 2015, 16(900):7 pages.
Selvaraj et al., "Whole-Genome Haplotype Reconstruction Using Proximity-Ligation and Shotgun Sequencing", Nature Biotechnology, 2013, 31(12):1111-1118.
Senguven et al., "Comparison of Methods for the Extraction of DNA from Formalin-Fixed, Paraffin-Embedded Archival Tissues", International Journal of Medical Sciences, 2014, 11(5):494-499.
Sepp et al., "Rapid Techniques for DNA Extraction from Routinely Processed Archival Tissue for Use in PCR", Journal of Clinical Pathology, 1994, 47:318-323.
Shi et al., "Complete Solubilization of Formalin-Fixed, Parafffin-Embedded Tissue May Improve Proteomic Studies", Proteomics Clinical Applications, Apr. 2013, 7(0): 264-272.
Shi et al., "DNA Extraction from Archival Formalin-fixed, Paraffin-embedded Tissue Sections Based on the Antigen Retrieval Principle: Heating Under the Influence of pH", The Journal of Histochemistry & Cytochemistry, 2002, 50(8):1005-1011.
Shi et al., "DNA Extraction from Archival Formalin-Fixed, Paraffin-Embedded Tissues: Heat-Induced Retrieval in Alkaline Solution", Histochemistry and Cell Biology, Springer, Berlin, DE, 2002, 122:211-218.
Simonis et al., "Nuclear Organization of Active and Inactive Chromatin Domains Uncovered by Chromosome Conformation Capture-On-Chip (4C)", Nature Genetics, Nov. 2006, 38(11)1348-1354.
Stamenova et al., "The Hi-Culfite Assay Reveals Relationships Between Chromatin Contacts and DNA Methylation State", bioRxiv, 2018, 28 pages.
Troll et al., "Structural Variation Detection by Proximity Ligation from Formalin-Fixed, Paraffin-Embedded Tumor Tissue", The Journal of Molecular Diagnostics, May 2019, 21(3):375-383.
Van De Werken et al., "Robust 4C-seq Data Analysis to Screen for Regulatory DNA Interactions", Nature Methods, Oct. 2012, 9(10)969-972.
Zeng et al., "Liquid Biopsies: DNA Methylation Analyses in Circulating Cell-Free DNA", Journal of Genetics and Genomics, Apr. 20, 2018, 45(4):185-192.
Zhang et al., "Haplotype Phasing of Whole Human Genomes Using Bead-Based Barcode Partitioning in a Single Tube", Nat Biotechnology, Sep. 2017, 35(9):852-857.
Zheng et al., "Haplotyping Germline and Cancer Genomes with High-Throughput Linked-Read Sequencing", Nature Biotechnology, Mar. 2016, 34(3):303-311.
Zhong et al., "Enhanced and Controlled Chromatin Extraction from FFPE Tissues and the Application to ChIP-Seq", BMC Genomics, 2019, 20:249:11 pages.
International Preliminary Report on Patentability dated Jun. 3, 2021 in International Patent Application No. PCT/US2019/062298 filed on Nov. 19, 2019, 15 pages.
Shi, et al. "Antigen Retrieval Techniques: Current Perspectives", The Journal of Histochemistry & Cytochemistry, 2001, 49(8):931-937.

\* cited by examiner

Extension of the chromatin solubilization and decompaction reaction to 80min improves spatial-proximal contiguity signal from FFPE samples Extension of the chromatin solubilization and decompaction reaction to 180min does not significantly improve spatial-proximal contiguity signal from 5um FFPE samples Increasing the temperature of chromatin solubilization and decompaction to extreme heat improves spatial-proximal contiguity signal from 10um FFPE samples Chromatin solubilization and decompaction at 74C for 40min optimally captures spatial-proximal contiguity signal from a clinical human FFPE tumor sample Cellular lysis is not required to capture optimal spatial-proximal contiguity signal from FFPE samples Schematic of protein:cfDNA complexes after binding to a carboxylated solid phase element and undergoing protein:DNA crosslinking Schematic of capturing spatial-proximal contiguity information from protein:cfDNA complexes via compartmentalization with solid phase element and tagging with compartment-specific molecular barcodes (i) Native spatially proximal nucleic acid molecules in the form of marked protein:cfDNA co-bound to a solid phase element and crosslinked (ii) Detach from solid phase element (iii) Affinity purify, compartmentalize and tag, such as via ligation of a compartment-specific barcoded oligonucleotide.

(iv) After compartmentalization and tagging, purified templates are formed and prepared for sequencing.

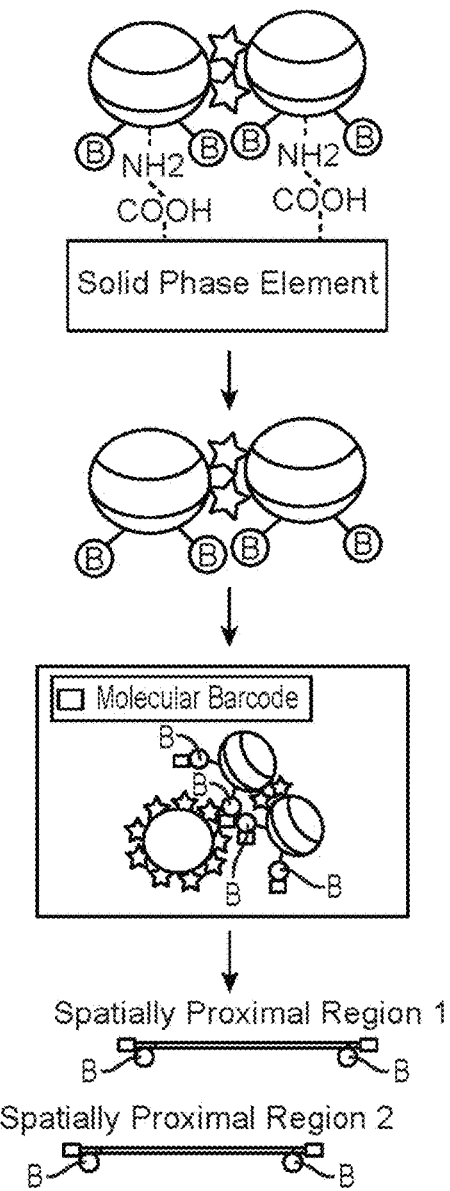

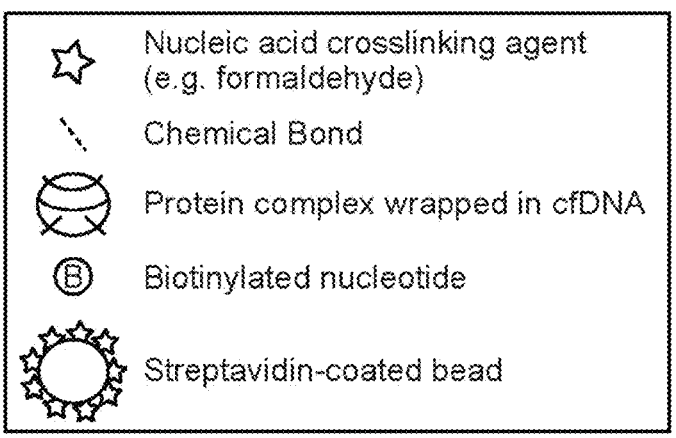

- ☆ Nucleic acid crosslinking agent (e.g. formaldehyde)
- \ Chemical Bond
- ◌ Protein complex wrapped in cfDNA
- Ⓑ Biotinylated nucleotide
- ✹ Streptavidin-coated bead

FIG. 13

Schematic of capturing spatial-proximal contiguity information from protein:cfDNA complexes via virtual compartmentalization using bead-linked transposome carrying virtual compartment-specific barcodes (i) Native spatially proximal nucleic acid molecules in the form of protein:cfDNA co-bound to a solid phase element and crosslinked

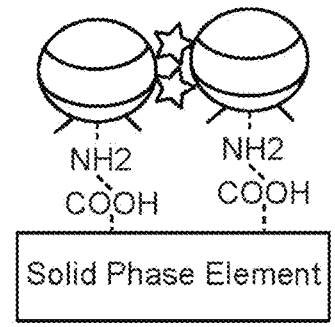

(ii) Detach from solid phase element

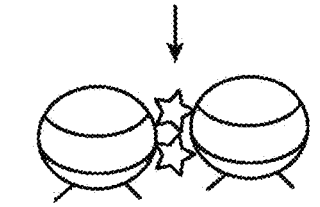

(iii) Tagment with bead-linked transposome carrying virtual compartment-specific barcoded oligonucleotides.

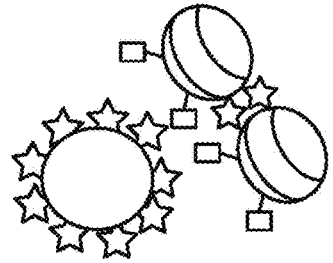

(iv) After virtual compartmentalization and tagging, purified templates are formed and prepared for sequencing.

Spatially Proximal Region 1

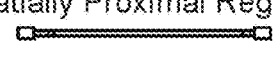

Spatially Proximal Region 2

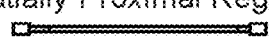

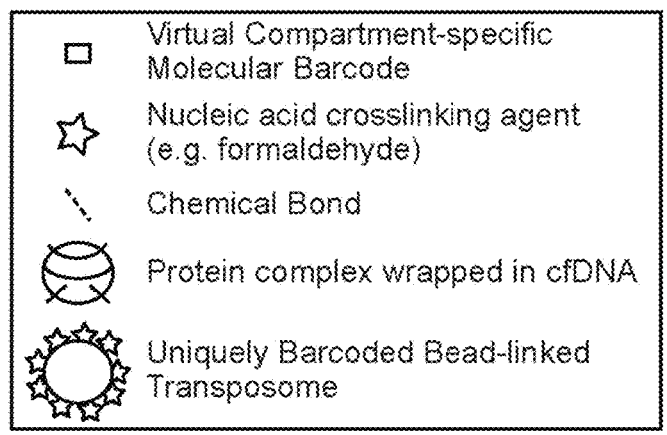

FIG. 14

Failed chromatin digestion in FFPE cells.

Discovery and validation of translocations in a FFPE GIST tumor.
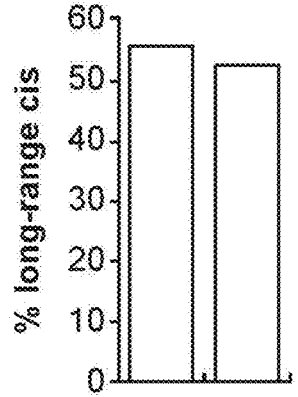
FIG. 23A
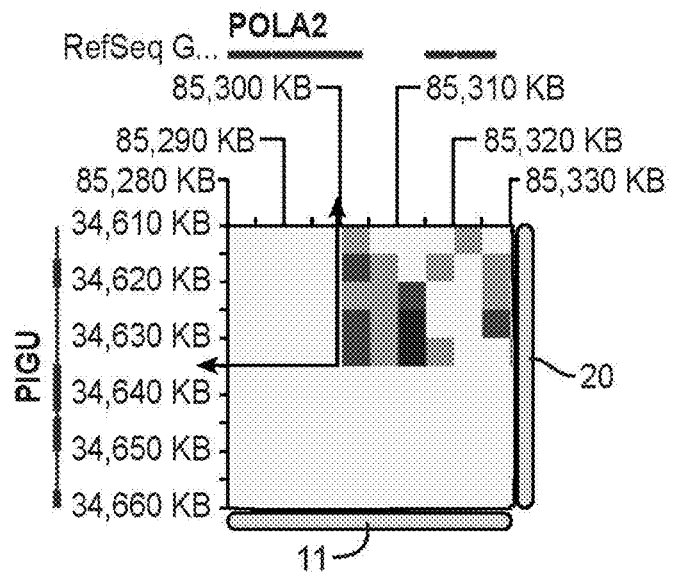
FIG. 23B
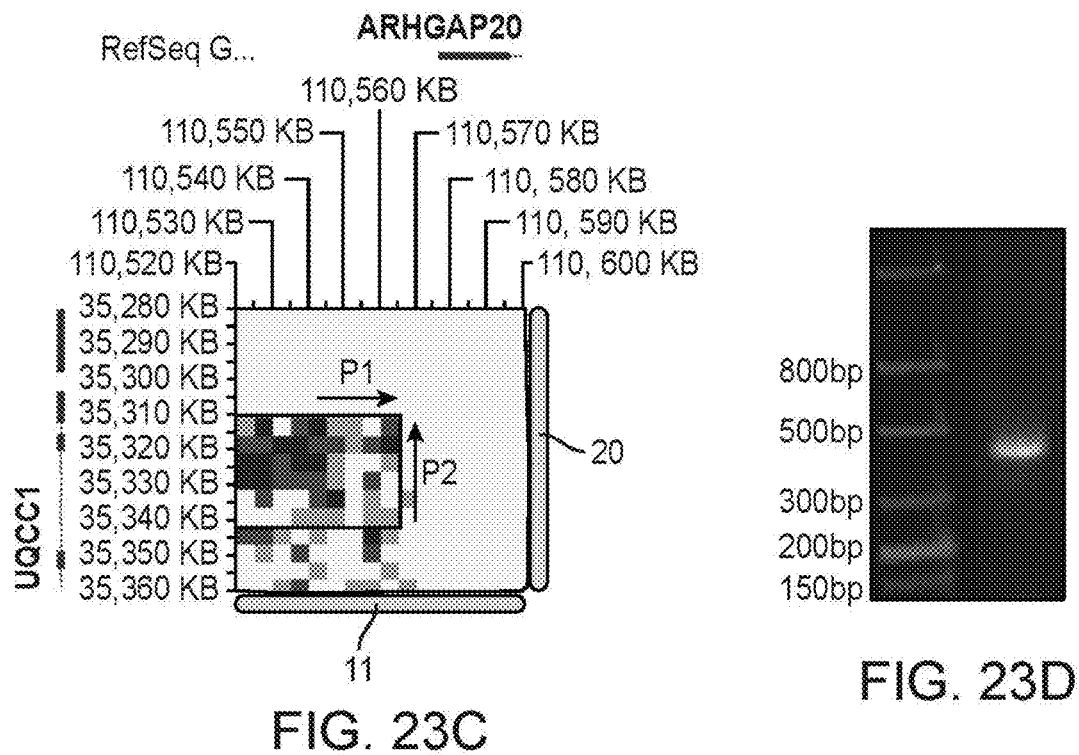
FIG. 23C
FIG. 23D Discovery of translocations in an FFPE ependymoma tumor Discovery of translocations in FFPE tumors across archival periods.

METHODS AND COMPOSITIONS FOR PREPARING NUCLEIC ACIDS THAT PRESERVE SPATIAL-PROXIMAL CONTIGUITY INFORMATION

RELATED PATENT APPLICATION(S)

This application claims the benefit of U.S. Provisional Patent Application No. 62/785,643 filed Dec. 27, 2018 entitled METHODS AND COMPOSITIONS FOR PREPARING NUCLEIC ACIDS THAT PRESERVE SPATIAL-PROXIMAL CONTIGUITY INFORMATION, naming Anthony Schmitt, Catherine Tan, Derek Reid, Chris De La Torre and Siddarth Selvaraj as inventors. This application also claims the benefit of U.S. Provisional Patent Application No. 62/770,135 filed Nov. 20, 2018, entitled METHODS FOR PREPARING NUCLEIC ACIDS THAT PRESERVE SPATIAL-PROXIMAL CONTIGUITY INFORMATION, naming Anthony Schmitt, Catherine Tan, Derek Reid, Chris De La Torre and Siddarth Selvaraj as inventors. This application is also related to U.S. Provisional Patent Application No. 62/589,505 filed Nov. 21, 2017, entitled PRESERVING SPATIAL-PROXIMAL CONTIGUITY AND MOLECULAR CONTIGUITY IN NUCLEIC ACID TEMPLATES, naming Siddarth Selvaraj, Anthony Schmitt and Bret Reid as inventors. This patent application is also related to PCT Application No. PCT/US18/62005 filed Nov. 20 2018, entitled PRESERVING SPATIAL-PROXIMAL CONTIGUITY AND MOLECULAR CONTIGUITY IN NUCLEIC ACID TEMPLATES naming Siddarth Selvaraj, Anthony Schmitt and Bret Reid as inventors. The entire content of the foregoing patent applications are incorporated herein by reference, including all text, tables and drawings.

FIELD

This technology relates to sequencing nucleic acids.

BACKGROUND

Next-generation sequencing (NGS) has emerged as the predominant set of methods for determining nucleic acid sequence for a plethora of research and clinical applications. The typical NGS workflow is as follows: the native genomic DNA, often organized as chromosome(s), is isolated from the nucleic acid source leading to its fragmentation, to produce nucleic acid templates which are subsequently read by a sequencing instrument to generate sequence data.

SUMMARY

The technology pertains to methods for preparing nucleic acids in such a way that preserves DNA spatial-proximal contiguity sequence information enabling the detection of spatially proximal nucleic acids (e.g. HiC), serving applications that benefit from long-range sequence contiguity information (e.g. haplotype phasing, genomic rearrangement detection and other applications that are enabled by long-range sequence contiguity information).

Preserving spatial-proximal contiguity information during the preparation of DNA from a sample of interest allows preserving contiguity in sequencing data obtained therefrom. Contiguity-preserved sequencing data enables comprehensive determination of nucleic acid sequence, as manifested in the contiguity-preserved nucleic acid template, by enabling identification of genomic variants, determination of contiguity information to inform genome assemblies de novo, deconvolution of haplotype phase information, genomic rearrangement detection, which together are fundamental to understand the role of genetics in living systems.

Formalin-fixed paraffin-embedded samples are typically not successfully prepared using the initial steps of standard protocols designed for cells, i.e., cells that are not formalin-fixed paraffin-embedded (see Example 18).

Provided in certain aspects is a method for preparing nucleic acids from a formalin-fixed paraffin-embedded (FFPE) sample, that preserves spatial-proximal contiguity information, comprising: a) providing a formalin-fixed paraffin-embedded sample; b) de-waxing the sample to produce a dewaxed sample; c) rehydrating the dewaxed sample, thereby generating a dewaxed/rehydrated sample; d) contacting the dewaxed/rehydrated sample with lysis buffer, thereby generating a lysed sample; e) contacting the lysed sample with denaturing detergent at a temperature greater than 65° C., thereby generating a solubilized and decompacted sample; and f) contacting the solubilized and decompacted sample with one or more reagents that preserve spatial-proximal contiguity information in the nucleic acids of the solubilized and decompacted sample.

Also provided in certain aspects is a method wherein the dewaxed/rehydrated sample is contacted with an extracellular matrix protease prior to contact with lysis buffer.

Also provided in certain aspects is a method for preparing nucleic acids from a formalin-fixed paraffin-embedded (FFPE) sample, that preserves spatial-proximal contiguity information, comprising: a) providing a formalin-fixed paraffin-embedded sample; b) de-waxing the sample to produce a dewaxed sample; c) rehydrating the dewaxed sample, thereby generating a dewaxed/rehydrated sample; d) contacting the dewaxed/rehydrated sample with denaturing detergent at a temperature greater than 65° C., thereby generating a solubilized and decompacted sample; and e) contacting the solubilized and decompacted sample with one or more reagents that preserve spatial-proximal contiguity information in the nucleic acids of the solubilized and decompacted sample.

Also provided in certain aspects is a method wherein the dewaxed/rehydrated sample is contacted with an extracellular matrix protease prior to contact with denaturing detergent.

Also provided in certain aspects is a method for preparing nucleic acids from a formalin-fixed paraffin-embedded (FFPE) sample, that preserves spatial-proximal contiguity information comprising: a) providing a formalin-fixed paraffin-embedded sample, that has not been dewaxed/rehydrated; b) contacting the formalin-fixed paraffin-embedded sample with lysis buffer, thereby generating a lysed sample; c) contacting the lysed sample with denaturing detergent at a temperature greater than 65° C., thereby generating a solubilized and decompacted sample; and d) contacting the solubilized and decompacted sample with one or more reagents that preserve spatial-proximal contiguity information in the nucleic acids of the solubilized and decompacted sample.

Also provided in certain aspects is a method wherein the sample is contacted with an extracellular matrix protease prior to contact with lysis buffer.

Also provided in certain aspects is a method for preparing nucleic acids from a formalin-fixed paraffin-embedded (FFPE) sample, that preserves spatial-proximal contiguity information comprising: a) providing a formalin-fixed paraffin-embedded sample, that has not been dewaxed/rehydrated; b) contacting the formalin-fixed paraffin-embedded sample with denaturing detergent at a temperature greater than 65° C., thereby generating a solubilized and decompacted sample; and c) contacting the solubilized and decompacted sample with one or more reagents that preserve spatial-proximal contiguity information in the nucleic acids of the solubilized and decompacted sample.

Also provided in certain aspects is a method wherein the sample is contacted with an extracellular matrix protease prior to contact with denaturing detergent.

Also provided in certain aspects is a method for preparing nucleic acids from a deeply formalin-fixed sample, that preserves spatial-proximal contiguity information comprising: a) providing a deeply formalin-fixed sample; b) contacting the deeply formalin-fixed sample with lysis buffer, thereby generated a lysed sample; c) contacting the lysed sample with denaturing detergent at a temperature greater than 65° C., thereby generating a solubilized and decompacted sample; and d) contacting the solubilized and decompacted sample with one or more reagents that preserve spatial-proximal contiguity information in the nucleic acids of the solubilized and decompacted sample.

Also provided in certain aspects is a method wherein the deeply formalin-fixed sample is contacted with an extracellular matrix protease prior to contact with lysis buffer.

Also provided in certain aspects is a method for preparing nucleic acids from a deeply formalin-fixed sample, that preserves spatial-proximal contiguity information comprising: a) providing a deeply formalin-fixed sample; b) contacting the deeply formalin-fixed sample with denaturing detergent at a temperature greater than 65° C., thereby generating a solubilized and decompacted sample; and c) contacting the solubilized and decompacted sample with one or more reagents that preserve spatial-proximal contiguity information in the nucleic acids of the solubilized and decompacted sample.

Also provided in certain aspects is a method wherein the deeply formalin-fixed sample is contacted with an extracellular matrix protease prior to contact with denaturing detergent.

Also provided in certain aspects is a method for preparing nucleic acids from a formalin-fixed paraffin-embedded (FFPE) sample, that preserves spatial-proximal contiguity information, comprising: a) providing a formalin-fixed paraffin-embedded sample; b) dewaxing the sample to produce a dewaxed sample; c) rehydrating the dewaxed sample, thereby generating a dewaxed/rehydrated sample; d) contacting the dewaxed/rehydrated sample with an extracellular matrix protease; thereby generating a dissociated sample; e) contacting the dissociated sample with lysis buffer, thereby generating a lysed sample; f) contacting the lysed sample with sodium dodecyl sulfate (SDS) at a temperature of 74° C. for 40 minutes, thereby generating a solubilized and decompacted sample; and g) contacting the solubilized and decompacted sample with one or more reagents that generate proximity ligated nucleic acid molecules in situ, thereby preserving spatial-proximal contiguity information in the nucleic acids of the solubilized and decompacted sample.

Also provided in certain aspects is a method for preparing nucleic acids from a formalin-fixed paraffin-embedded (FFPE) sample of cells, that preserves spatial-proximal contiguity information comprising: a) providing a formalin-fixed paraffin-embedded sample of cells; b) de-waxing the sample to produce a dewaxed sample; c) rehydrating the dewaxed sample, thereby generating a dewaxed/rehydrated sample; d) contacting the dewaxed/rehydrated sample with lysis buffer, thereby generating a lysed sample; e) contacting the lysed sample with denaturing detergent at a temperature of 62° C. for greater than 10 minutes, thereby generating a solubilized and decompacted sample; and f) contacting the solubilized and decompacted sample with one or more reagents that preserve spatial-proximal contiguity information in the nucleic acids of the solubilized and decompacted sample.

Also provided in certain aspects is a method for preparing nucleic acids from a formalin-fixed paraffin-embedded (FFPE) sample of cells, that preserves spatial-proximal contiguity information comprising: a) providing a formalin-fixed paraffin-embedded sample of cells; b) de-waxing the sample to produce a dewaxed sample; c) rehydrating the dewaxed sample, thereby generating a dewaxed/rehydrated sample; d) contacting the dewaxed/rehydrated sample; with denaturing detergent at a temperature of 62° C. for greater than 10 minutes, thereby generating a solubilized and decompacted sample; and e) contacting the solubilized and decompacted sample with one or more reagents that preserve spatial-proximal contiguity information in the nucleic acids of the solubilized and decompacted sample.

Also provided in certain aspects is a method for preparing nucleic acids from a deeply formalin-fixed sample of cells, that preserves spatial-proximal contiguity information comprising: a) providing a deeply formalin-fixed sample of cells; b) contacting the deeply formalin-fixed sample with lysis buffer, thereby generated a lysed sample; c) contacting the lysed sample with denaturing detergent at a temperature of 62° C. for greater than 10 minutes, thereby generating a solubilized and decompacted sample; and d) contacting the solubilized and decompacted sample with one or more reagents that preserve spatial-proximal contiguity information in the nucleic acids of the solubilized and decompacted sample.

Also provided in certain aspects is a method for preparing nucleic acids from a deeply formalin-fixed sample of cells, that preserves spatial-proximal contiguity information comprising: a) providing a deeply formalin-fixed sample of cells; b) contacting the deeply formalin-fixed sample with denaturing detergent at a temperature of 62° C. for greater than 10 minutes, thereby generating a solubilized and decompacted sample; and c) contacting the solubilized and decompacted sample with one or more reagents that preserve spatial-proximal contiguity information in the nucleic acids of the solubilized and decompacted sample.

Also provided in certain aspects is a method for preparing nucleic acids from a formalin-fixed paraffin-embedded (FFPE) sample of cells, that preserves spatial-proximal contiguity information comprising: a) providing a formalin-fixed paraffin-embedded sample of cells, b) contacting the formalin-fixed paraffin-embedded sample with lysis buffer, thereby generating a lysed sample; c) contacting the lysed sample with denaturing detergent at a temperature of 62° C. for greater than 10 minutes, thereby generating a solubilized and decompacted sample; and d) contacting the solubilized and decompacted sample with one or more reagents that preserve spatial-proximal contiguity information in the nucleic acids of the solubilized and decompacted sample.

Also provided in certain aspects is a method for preparing nucleic acids from a formalin-fixed paraffin-embedded (FFPE) sample of cells, that preserves spatial-proximal contiguity information comprising: a) providing a formalin-fixed paraffin-embedded sample of cells, b) contacting the formalin-fixed paraffin-embedded sample with denaturing detergent at a temperature of 62° C. for greater than 10 minutes, thereby generating a solubilized and decompacted sample; and c) contacting the solubilized and decompacted sample with one or more reagents that preserve spatial-proximal contiguity information in the nucleic acids of the solubilized and decompacted sample.

Also provided in certain aspects is a method for preparing nucleic acids from a sample comprising protein:cfDNA complexes, that preserves spatial-proximal contiguity information, comprising: a) providing a sample comprising protein:cfDNA complexes; b) crosslinking the protein:cfDNA complexes to neighboring protein:cfDNA complexes; and c) contacting the crosslinked protein:cfDNA complexes with one or more reagents that preserve spatial-proximal contiguity information in the cell free DNA of the sample.

Also provided in certain aspects is a method for preparing nucleic acids from a sample comprising protein:cfDNA complexes, that preserves spatial-proximal contiguity information, comprising: a) providing a sample comprising protein:cfDNA complexes; b) contacting the sample with a solid phase, thereby generating protein:cfDNA complexes associated with a solid phase; c) crosslinking the protein:cfDNA complexes to neighboring protein:cfDNA complexes or to the solid phase; and d) contacting the crosslinked protein:cfDNA complexes with one or more reagents that preserve spatial-proximal contiguity information in the cell free DNA of the sample.

Also provided in certain aspects are methods to preserve spatial-proximal contiguity information comprising use of proximity ligation, solid substrate-mediated proximity capture (SSPC), compartmentalization with or without a solid substrate or a Tn5 tetramer.

Also provided in certain aspects are methods wherein nucleic acids with preserved spatial-proximal contiguity information are sequenced to produce sequence readouts. In certain aspects, the sequence readouts are utilized in applications that are based on the use of long-range sequence contiguity information.

Also provided in certain aspects are methods wherein nucleic acids with preserved spatial-proximal contiguity information are subjected to bisulfite treatment to generate bisulfite treated nucleic acids with preserved spatial-proximal contiguity information.

Also provided in certain aspects are methods wherein the bisulfite treated nucleic acids with preserved spatial-proximal contiguity information are sequenced to determine the methylation status of the nucleic acids with preserved spatial-proximal contiguity information.

Also provided in certain aspects are kits comprising reagents for performing the methods described herein.

Also provided in certain aspects are methods for rapidly reversing crosslinking in a sample crosslinked to preserve spatial-proximal contiguity information.

Certain embodiments are described further in the following description, examples, claims and drawings.

BRIEF DESCRIPTION OF THE DRAWINGS

The drawings illustrate certain embodiments of the technology and are not limiting. For clarity and ease of illustration, the drawings are not made to scale and, in some instances, various aspects may be shown exaggerated or enlarged to facilitate an understanding of particular embodiments.

FIG. 1A shows results of experiments with 10 um sections and reaction times of 10 minutes and 40 minutes. FIG. 1B shows results of experiments with 10 um sections and reaction times of 40 minutes, 60 minutes and 80 minutes. FIG. 1C shows results of experiments with 10 um sections and reaction times of 40 minutes, 80 minutes, 120 minutes and 180 minutes. FIG. 1D shows results of experiments with 5 um sections and reaction times of 40 minutes, 80 minutes, 120 minutes and 180 minutes.

FIG. 2A shows the results of experiments with 5 um sections, at three temperatures (50° C., 62° C. and 74° C.) and reaction times of 10 minutes, 40 minutes and 80 minutes.

FIG. 2B shows the results of experiments with 10 um sections, at a temperature of 74° C. and reaction times of 10 minutes, 40 minutes and 80 minutes.

FIG. 5A shows de-waxing and rehydration is required to capture spatial-proximal contiguity signal from FFPE samples when the SDS reaction is at 62° C. FIG. 5B shows de-waxing and rehydration is not required to capture spatial-proximal contiguity signal from FFPE samples when the SDS reaction is at 74° C. and longer duration.

FIG. 13 illustrates capturing spatial-proximal contiguity information from protein:cfDNA complexes via compartmentalization with solid phase element and tagging with compartment-specific molecular barcodes.

FIG. 14 illustrates capturing spatial-proximal contiguity information from protein:cfDNA complexes via virtual compartmentalization using bead-linked transposome carrying virtual compartment-specific molecular barcodes.

FIGS. 23A-D show discovery and validation of translocations in an FFPE GIST tumor. FIG. 23A show shallow sequencing analysis (0.75×). FIG. 23B shows sequence analysis at 10×. FIG. 23C shows amplification across the translocation breakpoint. FIG. 23D shows PCR results.

FIG. 24A shows HiC data from PFE cell lines. FIG. 24B shows shallow sequencing analysis (0.25×). FIG. 24C shows FFPE-HiC analyses of a PFE tumor.

FIG. 25A shows shallow sequencing analysis (0.05×). FIG. 25B shows intra-chromosome translocations.

FIG. 25C shows inter-chromosome translocation between chr3;chr18. FIG. 25D shows inter-chromosome translocation between chr3; chr 7 translocation

DETAILED DESCRIPTION

Provided herein are methods for preparing nucleic acids from particular types of samples that preserves spatial-proximal contiguity information in the sequence of the nucleic acids. Nucleic acid molecules that preserve spatial-proximal contiguity information can fragmented and sequenced using short-read sequencing methods (e.g. Illumina, nucleic acid fragments of lengths approximately 500 bp) or intact molecules that preserve spatial-proximal contiguity information can be sequenced using long-read sequencing (e.g. Pacific Bioscience (now Illumina), Oxford Nanopore, or others, nucleic acid fragments of lengths approximately 30 Kbp or greater).

In certain embodiments, a sample can be a fixed sample that is embedded in a material such as paraffin (wax). In some embodiments, a sample can be a formalin fixed sample. In certain embodiments, a sample is formalin-fixed paraffin-embedded sample. In some embodiments, a formalin-fixed paraffin-embedded sample can be a tissue sample or a cell culture sample. In some embodiments, a tissue sample has been excised from a patient and can be diseased or damaged. In some embodiments, a tissue sample is not known to be diseased or damaged. In certain embodiments, a formalin-fixed paraffin-embedded sample can be a formalin-fixed paraffin-embedded section, block, scroll or slide. In certain embodiments, a sample can be a deeply formalin-fixed sample, as described below.

In certain embodiments, a formalin-fixed paraffin-embedded sample is provided on a solid surface and a method of preparing nucleic acid that preserves spatial-proximal contiguity information is performed on the solid surface. In some embodiments, a solid surface is a pathology slide. In some embodiments, additional downstream reactions are also performed on the solid surface. Those of skill in the art are familiar with methods that can be substituted for steps requiring centrifugation and that achieve a comparable result, but are performed on a solid surface.

Low Input DNA

Figure 26:
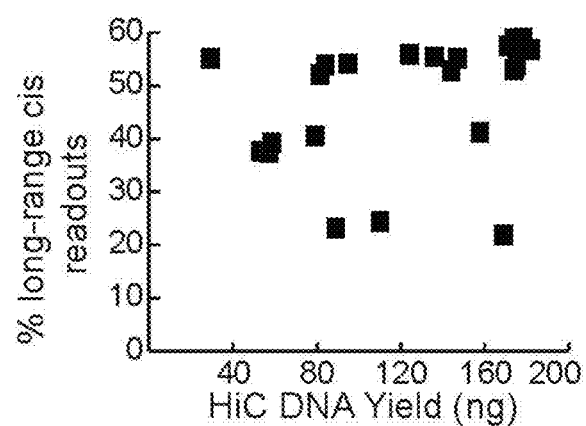
FIG. 26 shows high quality FFPE-HiC from low input FFPE tissue.

Often it is difficult to obtain even small amounts of DNA from FFPE samples (input DNA) that is of a quality that allows for spatial-proximity analysis, such as HiC analysis. In certain embodiments, utilizing the optimized protocols described herein, DNA is extracted from an FFPE sample or a deeply formalin-fixed sample, even in a low amount, that produces sufficient long-range cis readouts for robust spatial-proximity analysis and use in other applications (see FIG. 26). In certain embodiments, the input DNA extracted from a sample is less than 200 ng. In certain embodiments, the amount of input DNA extracted from a sample is less than 160 ng, less than 120 ng, less than 80 ng, less than 40 ng, less than 20 ng, less than 10 ng, less than 5 ng, less than 2 ng or less than 1 ng.

Extended Archival Periods

Prolonged FFPE archival periods or prolonged deeply formalin-fixed archival periods are known to degrade DNA and make genomic analyses more technically challenging and therefore is a critical parameter to evaluate when developing a robust genomic analysis method for FFPE samples and for deeply formalin-fixed samples. In certain aspects, utilizing the optimized protocols described herein, DNA is obtained from long archival periods that results in sufficient long-cis readouts for robust spatial-proximity analysis and use in other applications (see FIGS. 25A-D). In some embodiments, an extended archival period is greater than about 1 year, greater than about 4 years, greater than about 10 years, greater than about 20 years, greater than about 30 years, greater than about 40 years, greater than about 50 years, greater than about 60 years or greater than about 70 years, or sometimes about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80 years. In certain embodiments, the sample has an archival period of about 4 years to about 20 years. In certain embodiments, the sample has an archival period of about 20 years to about 70 years. In some embodiments, the archival period can be less than about 4 years, less than about 3 years, less than about 2 years or less than about 1 year, if the sample is of low quality, i.e., the DNA of the sample is degraded to an extent often observed for samples with longer archival periods.

Preparation of Formalin-Fixed Paraffin Embedded (FFPE) Samples with De-Waxing/Rehydrating In certain embodiments, a formalin-fixed paraffin-embedded sample is dewaxed. De-waxing can be carried out by contacting the formalin-fixed paraffin-embedded sample with any known agent that dissolves wax. In some embodiments, the agent is a solvent. In some embodiments, the solvent is an organic solvent. In some embodiments, the solvent is xylene. In some embodiments, the solvent is toluene, benzene or any other suitable solvent. In some embodiments, the agent is a non-toxic agent, including but not limited to mineral oil, or an agent with low-toxicity, including but not limited to limonene.

In certain embodiments, a dewaxed formalin-fixed paraffin-embedded sample is rehydrated. In certain embodiments, the dewaxed sample is rehydrated by contact with ethanol (or any agent that is useful for removing a solvent from the sample) and re-suspended in water or a suitable buffer.

In some embodiments, a dewaxed/rehydrated formalin-fixed paraffin-embedded sample is contacted with a lysis buffer prior to contact with a denaturing detergent. As used herein, the term "lysis buffer" refers to a buffered solution able to lyse cell membranes. Lysis buffers typically comprise salts, a protease inhibitor and a non-ionic, non-denaturing detergent and are known by those who practice the art. In certain embodiments the lysis buffer is hypotonic. In certain embodiments, the lysis buffer comprises a protease inhibitor. In certain embodiments the lysis buffer comprises a nonionic non-denaturing detergent. In some embodiments, the non-ionic non-denaturing detergent is IGEPAL or an equivalent detergent. In certain embodiments the lysis buffer does not include a protease.

In certain embodiments, a dewaxed/rehydrated formalin-fixed paraffin-embedded sample is not contacted with a lysis buffer prior to contact with a denaturing detergent. Without being held to a theory, whether lysis buffer is required may depend on the thickness of a formalin-fixed paraffin-embedded tissue section. In certain embodiments, the formalin-fixed paraffin-embedded tissue section is from about 5 to about 10 um in thickness. In certain embodiments, the formalin-fixed paraffin-embedded tissue section is about 5 um or less in thickness. A tissue section with a thickness of about 5 um is less than the thickness of a nucleus. Without being bound by theory, a tissue section with a thickness of about 5 um slices through a nucleus and provides direct access to the interior of the nucleus, thus cell lysis may not be required. Lysis buffer may also not be required when contact with denaturing detergent is at an elevated temperature (e.g., greater than 65° C.) and/or for greater than 10 minutes.

In certain embodiments, there is no reagent utilized specifically to dissociate or break apart the tissue of the sample. For example, there is no enzymatic dissociation with a protease.

In certain embodiments, a dewaxed/rehydrated formalin-fixed paraffin-embedded sample is contacted with a protease. In certain embodiments, the dewaxed/rehydrated formalin-fixed paraffin-embedded sample is contacted with the protease prior to contact with other reagents (e.g., lysis buffer, denaturing detergent). In some embodiments the protease is an extracellular matrix (ECM) protease that dissociates the tissue of the sample. In some embodiments, the extracellular matrix protease is collagenase and/or dispase. In certain embodiments the collagenase is ColI ColIII or ColIV. In some embodiments the dispase is Dispase I (Neutral Protease I). Without being bound to a theory, a protease may dissociate extracellular matrix proteins in the sample, thus improving the ease of handling and transfer of the sample.

In some embodiments, a dewaxed/rehydrated formalin-fixed paraffin-embedded sample is contacted with a denaturing detergent. As used herein, the term "denaturing detergent" refers to an anionic or cationic detergent. In certain embodiments the detergent can be sodium dodecyl sulfate (SDS).

As used herein, the term "solubilized and decompacted sample" refers to a sample contacted with a denaturing detergent and having one or more of the following features: permeabilized nuclei, de-condensed chromatin (decompacted) and/or solubilized chromatin that has preserved spatial-proximal contiguity information.

In some embodiments, contact with a denaturing detergent is for greater than about 10 minutes, or about 15 to about 80 minutes, about 20 to about 60 minutes, greater than 10 minutes to about 40 minutes, about 30 to about 50 minutes, about 35 minutes to about 45 minutes or sometimes about 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 or 80 minutes. In some embodiments, contact with a denaturing detergent is for about 40 minutes. In some embodiments, contact with a denaturing detergent is for 40 minutes.

In some embodiments, contact with a denaturing detergent is at a temperature of about 65° C. to about 90° C., about 70° C. to about 80° C. or sometimes about 65, 66, 67, 68, 69, 70, 71, 72, 73, 74, 75, 76, 77, 78, 79, 80, 81, 82, 83, 84, 85, 86, 87, 88, 89 or 90° C. In certain embodiments the temperature is 74° C. In some embodiments, contact with a detergent is at a temperature of greater than 65° C., at a temperature of greater than 65° C. and less than 80° C., at a temperature of between 70° C. and 80° C., or at a temperature of about 74° C. In some embodiments, the sample is a tissue sample.

In some embodiments, the sample comprises cells and contact with a denaturing detergent is at a temperature of about 62° C. for greater than 10 minutes. In some embodiments, the sample comprises cells and contact with a denaturing detergent is at a temperature of about 62° C. for 40 minutes.

In certain embodiments, the sample comprises tissues and contact with a denaturing detergent is at a temperature of about 74° C. for 40 minutes.

Preparation of Formalin-Fixed Paraffin Embedded (FFPE) Samples without De-Waxing/Rehydrating In certain embodiments, a formalin-fixed paraffin-embedded sample is not dewaxed and rehydrated. In some embodiments, a formalin-fixed paraffin-embedded sample that is not dewaxed and rehydrated is contacted with lysis buffer and the lysed sample is contacted with denaturing detergent. In some embodiments, a formalin-fixed paraffin-embedded sample that is not dewaxed and rehydrated is not contacted with lysis buffer and is directly contacted with denaturing detergent. In certain embodiments, a formalin-fixed paraffin-embedded sample that is not dewaxed and rehydrated is a tissue sample that is contacted with denaturing detergent at a temperature that is greater than 65° C. In some embodiments, the temperature is 74° C. In certain embodiments, a formalin-fixed paraffin-embedded tissue section that is not dewaxed and rehydrated is from about 5 to about 10 um in thickness. In certain embodiments, the formalin-fixed paraffin-embedded tissue section that is not dewaxed and rehydrated is about 5 um or less in thickness.

In certain embodiments, a formalin-fixed paraffin-embedded sample that is not dewaxed and rehydrated is provided on a solid surface. In some embodiments, the solid surface is a pathology slide.

Preparation of Deeply Formalin-Fixed Samples

In some embodiments, a sample is deeply fixed using formalin, but is not paraffin-embedded. For example, some surgical samples are fixed with formalin and preserved in a liquid solution.

Accordingly, such a deeply formalin-fixed sample does not require dewaxing and/or rehydration, but is otherwise typically processed the same as an FFPE sample.

In some embodiments, a deeply formalin-fixed sample is contacted with lysis buffer (as described herein) and the lysed sample is contacted with denaturing detergent. In some embodiments, a deeply formalin-fixed sample is not contacted with lysis buffer (as described herein) and the sample is contacted with denaturing detergent. In some embodiments, a deeply formalin-fixed sample is contacted with a protease.

Preserving Spatial-Proximal Contiguity Information

In certain embodiments, formalin-fixed paraffin-embedded (FFPE) samples with and without de-waxing/rehydrating and deeply formalin-fixed samples are processed using the described methods to generate a solubilized and decompacted sample which is contacted with one or more reagents that preserve spatial-proximal contiguity information in the nucleic acids of the sample. In certain embodiments, the formalin-fixed paraffin-embedded (FFPE) samples and deeply formalin-fixed samples are samples of tissues. In certain embodiments, the formalin-fixed paraffin-embedded (FFPE) samples and deeply formalin-fixed samples are samples of cells. Regardless of the type of sample, the same reagents that preserve spatial-proximal contiguity information are utilized.

As used herein, the term "reagents that preserve spatial-proximal contiguity information" refers to reagents and their methods of use that capture and preserve the native spatial conformation exhibited by nucleic acids when associated with proteins as in chromatin and/or as part of a nuclear matrix. Spatial-proximal contiguity information can be preserved by proximity ligation, by solid substrate-mediated proximity capture (SSPC), by compartmentalization with or without a solid substrate or by use of a Tn5 tetramer.

Proximity Ligation

In some embodiments, reagents that preserve spatial-proximal contiguity information are reagents that generate proximity ligated nucleic acid molecules that are utilized in methodologies comprising proximity ligation. A proximity ligation method is one in which natively occurring spatially proximal nucleic acid molecules are captured by ligation to generate ligated products. In some embodiments, reagents that generate proximity ligated nucleic acid molecules can include a restriction endonuclease, a DNA polymerase, a plurality of nucleotides comprising at least one biotinylated nucleotide, and a ligase. In certain embodiments, there are two restriction endonucleases.

Figure 15:
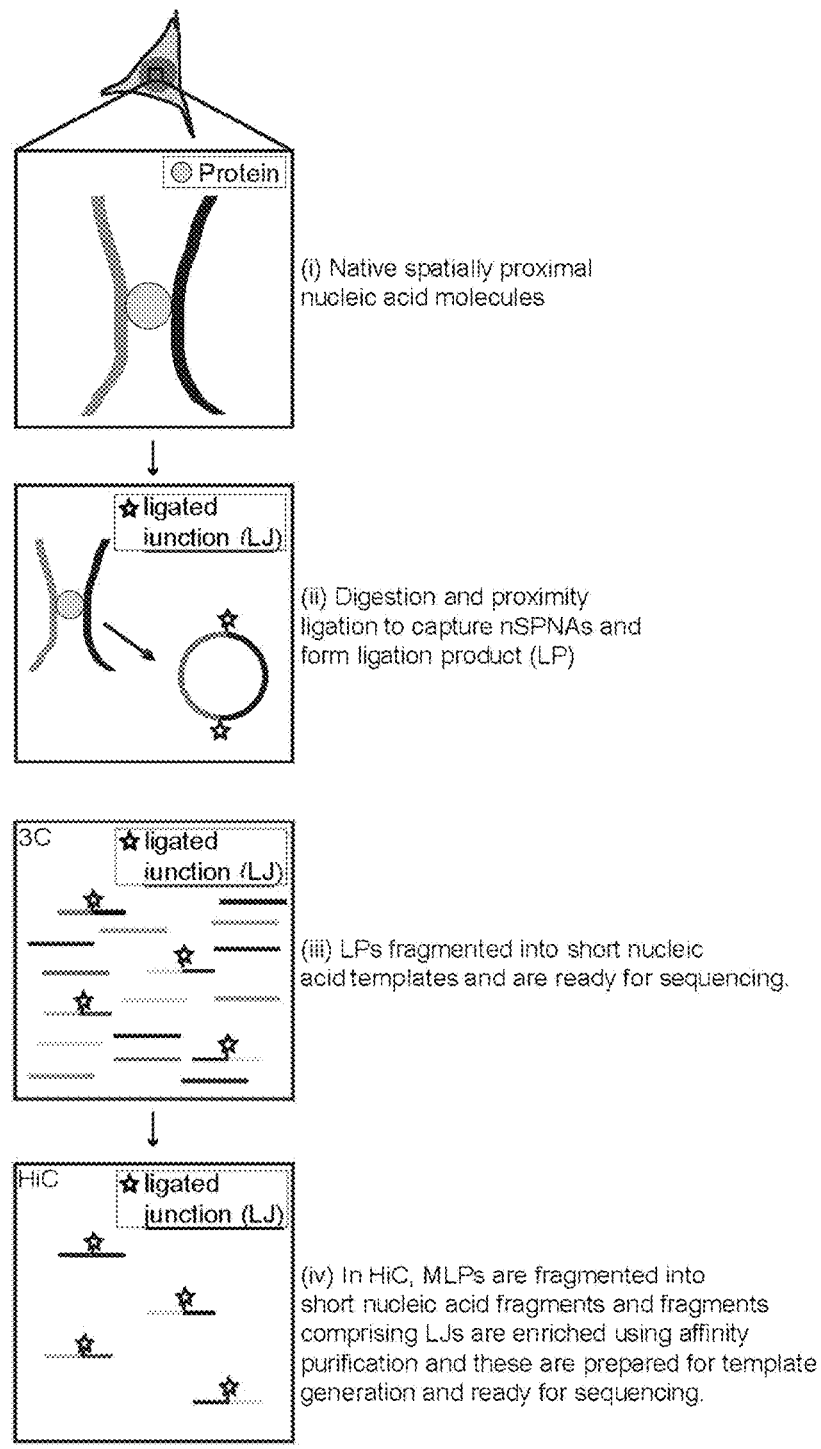
FIG. 15 illustrates capturing spatial-proximal contiguity information from FFPE samples via proximity ligation.

FIG. 15 shows capturing spatial-proximal contiguity information from FFPE samples via PL (Proximity Ligation) methods. PL methods begin with (i) native spatially proximal nucleic acids (nSPNAs) within a nucleic acids source (e.g. FFPE sample), followed by (ii) digestion (e.g. via RE) and ligation to generate ligation products (LPs). Note that for FFPE samples that are already highly fragmented, digestion of the DNA may not be necessary. Broadly, PL methods are classified as 3C-based and HiC-based, although there are many specific variations of PL. In 3C (iii), the plurality of LPs are fragmented, prepared as short nucleic acid templates and ready for sequencing. In HiC (iv), the digested nucleic acid ends are marked (e.g. biotinylated) and then ligated to create marked ligated products (MLPs, MLPs are a manifestation of LPs), bearing an affinity purification marker at the ligation junctions (Us). After the plurality of MLPs are fragmented, affinity purification is used to enrich for fragments of MLPs comprising Us and such fragments are prepared as nucleic acid templates and are ready for sequencing—i.e. the fragmented nucleic acids from the MLPs that contain at least an LJ are enriched and prepared as a template and sequenced in HiC, to deplete uMLPs (unligated MLPs that do not usually manifest Us).

Methods of carrying out proximity ligation are known in the art. For example, in the HiC method steps typically include: (1) digestion of chromatin of the solubilized and decompacted sample with a restriction enzyme (or fragmentation); (2) labelling the digested ends by filling in the 5'-overhangs with biotinylated nucleotides; and (3) ligating the spatially proximal digested ends, thus preserving spatial-proximal contiguity information. Once spatial-proximal contiguity information is preserved, further steps in the HiC method include: purifying and enriching the biotin-labelled ligation junction fragments, preparing a library from the enriched fragments and sequencing the library. (see Lieberman-Aiden et al. US2017/0362649, Lieberman-Aiden et al. Science 326, 289-293 (2009), Dekker et al. (U.S. Pat. No. 9,434,985)). (see FIG. 15) Another example of a proximity ligation method, often includes steps: (1) digestion of chromatin of the solubilized and decompacted sample with a restriction enzyme (or fragmentation); (2) blunting the digested or fragmented ends or omission of the blunting procedure; and (3) ligating the spatially proximal ends, thus preserving spatial-proximal contiguity information. Once spatial-proximal contiguity information is preserved, further steps can include: using size selection to purify and enrich ligated fragments, which represent ligation junction fragments, preparing a library from the enriched fragments and sequencing the library.

In some embodiments, the proximity ligated nucleic acid molecules are generated in situ. As used herein the term "in situ" refers to within a nucleus (see U.S. Application US2017/0362649).

Proximity ligation methods include, but are not limited to 3C (Dekker et al. Science 295, 1306-1311 (2002), 4C (Simonis et al. Nature Genetics 38, 1348-1354 (2006), De Laat et al. (U.S. Pat. No. 8,642,295)) 5C (Dostie et al. Genome Research 16, 1299-1309 (2006), Dekker et al. (U.S. Pat. No. 9,273,309), HiC (Lieberman-Aiden et al. US2017/0362649, Lieberman-Aiden et al. Science 326, 289-293 (2009), Dekker et al. (U.S. Pat. No. 9,434,985), TCC (Kalhor et al. Nature Biotechnology 30, 90-98 (2012), Chen et al. (US20110287947) 4C-seq (Van de Werken et al. Nat Methods. (2012)), ChIA-PET (Ruan et al U.S. Pat. No. 8,071,296), HiChIP (Mumbach et al. Nat Methods. (2016) PLAC-seq (Fang et al. Cell Research (2016)), Capture-C(Hughes et al. Nature Genetics (2014), Capture-HiC (Jager et al. Nature Communications, 2015), or other methods or combination of methods.

Regardless of the specific PL method, all PL methods capture spatial-proximal contiguity information in the form of ligation products, whereby a ligation junction is formed between two natively spatially proximal nucleic acids. Once the LPs are formed, the spatial-proximal contiguity information is detected using next generation sequencing, whereby one or more ligation junctions (either from an entire LP or fragment of an LP) are sequenced (as described herein). With these sequence information, one is informed that the nucleic acid molecules from a given ligation product (or ligation junction) are natively spatially proximal nucleic acids.

Solid Substrate-Mediated Proximity Capture (SSPC)

In some embodiments, reagents that preserve spatial-proximal contiguity information are reagents that comprise solid substrates that form complexes with the nucleic acid of the solubilized and decompacted sample and are utilized in methodologies comprising solid substrate-mediated proximity capture (SSPC). SSPC methods comprise introducing an exogenous solid substrate functionalized with surface molecule(s) that captures natively occurring spatially proximal nucleic acid molecules by binding to them. In some embodiments of solid substrate-mediated proximity capture (SSPC) a sample is contacted with solid substrates that form complexes with the nucleic acid of the sample prior to the sample being solubilized and decompacted.

Figure 16:
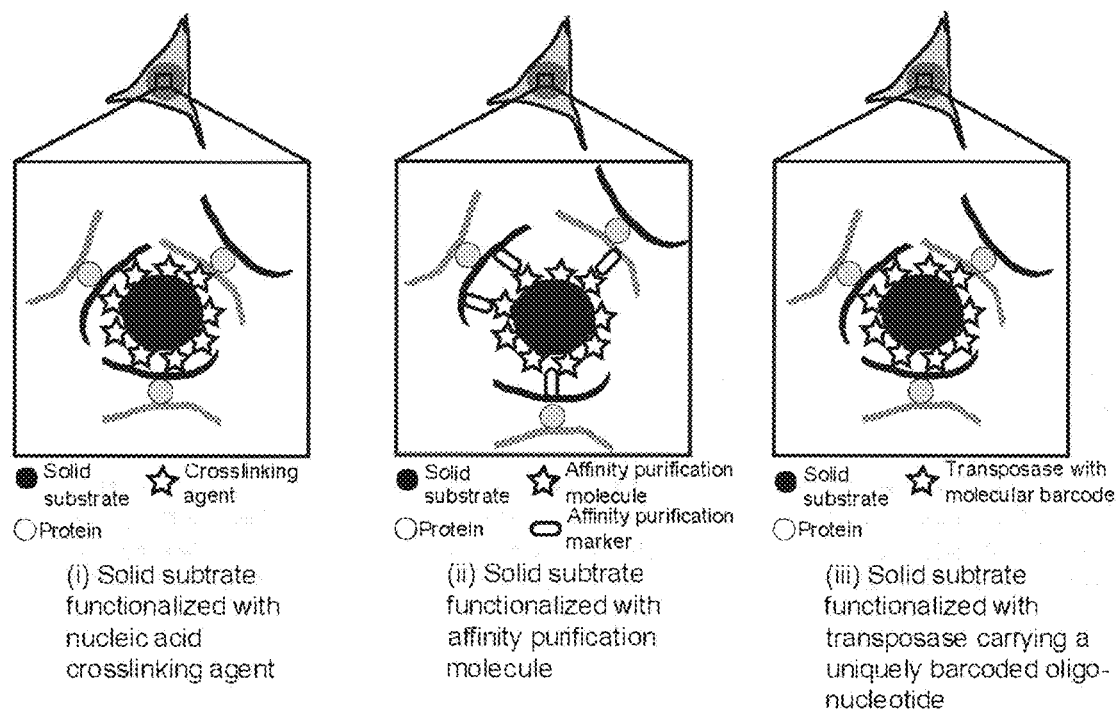
FIG. 16 illustrates capturing spatial-proximal contiguity information from FFPE samples via SSPC methods.

FIG. 16 illustrates of capturing spatial-proximal contiguity information from FFPE samples via SSPC methods. SSPC methods comprise introducing an exogenous solid substrate functionalized with surface molecule(s) that captures nSPNAs by binding them. In all cases, the solid substrate is introduced into a source of nucleic acids (e.g. FFPE sample), and in (i) the solid substrate is functionalized with a nucleic acid crosslinking agent such that the surface of the solid substrate becomes chemically bound to the nSPNAs for which it physically contacts. In (ii) the nucleic acids of the nucleic acid source are first labeled with an affinity purification marker and then a solid substrate functionalized with an affinity purification molecule is introduced such that the surface of the solid substrate becomes chemically bound to the labeled nSPNAs for which it physically contacts. In (iii) the solid substrate is functionalized with transposase bearing barcoded oligonucleotides, such that each solid substrate has its own set of uniquely barcoded oligonucleotides, and such that when the surface of the solid substrate comes in physical contact with nSPNAs, the barcoded oligonucleotides are integrated into nSPNAs.

As used herein, the term "solid substrate" refers to, for example, beads or other small solid phase particles or surfaces.

In certain embodiments, the solid substrates are solid substrates functionalized (e.g., coated) with a nucleic acid crosslinking agent (see FIG. 16, left panel). The surface of the solid substrate becomes chemically bound to the natively occurring spatially proximal nucleic acid molecules for which it physically contacts. Crosslinking agents are known in the art. In some embodiments the crosslinking reagent is psoralen. Spatial-proximal contiguity information is preserved by compartmentalizing (see below) and tagging molecules bound to a common solid phase substrate with a unique compartment specific molecular barcode (see below).

In some embodiments, nucleic acids are first labeled with an affinity purification marker (e.g. biotin), and a solid substrate is functionalized with an affinity purification molecule capable of binding the affinity purification marker (e.g. streptavidin) (see FIG. 16, middle panel) Similar to the aforementioned crosslinking-based SSPC method, spatial-proximal contiguity information is preserved by compartmentalizing and tagging molecules bound to a common solid phase substrate with a unique compartment-specific molecular barcode (see below).

In certain embodiments, the solid substrate is functionalized with transposases comprising barcoded oligonucleotides (e.g., Tn5). Each solid substrate has its own set of uniquely barcoded oligonucleotides, such that when the surface of the solid substrate comes in physical contact with nucleic acid molecules in the solubilized and decompacted sample the barcoded oligonucleotides are integrated into nucleic acid molecules, thus preserving spatial-proximal contiguity information (see FIG. 16, right panel). This is an example of "virtual" compartmentalization, as the uniquely barcoded transposases affixed to the solid substrate can be thought to represent its own "virtual" compartment, within which are a collection of uniquely barcoded nucleic acid molecules that represent spatial-proximal contiguity information (e.g. as in CPT-seqV2 (Zhang et al. Nature biotechnology 35, 852-857 (2017)). After tagging is completed, the transposome protein is typically denatured and thus would release the barcoded spatially proximal nucleic acid molecules from the bead-linked transposome. In some embodiments, denaturing is by contact with a detergent (e.g., 0.2% SDS for 15-30 minutes at about 55° C.) or contact with a chaotropic salt (e.g., guanidine hydrochloride). In some embodiments after the barcoded spatially proximal nucleic acid molecules are released, the beads are removed and the nucleic acid is purified (see below).

As used herein, the term "compartmentalizing" refers to the act of partitioning a plurality of nucleic acids which preserve spatial-proximal contiguity information into a multitude of discrete compartments such that each compartment is allocated with a sub-haploid quantity of nucleic acids. In cases of "physical" compartmentalization, a plurality of nucleic acids can be partitioned into discrete physical spaces (i.e. compartments) that are barred from intermixing with other compartments. Such a physical compartment might be the well of a microtiter plate (e.g. as in CPT-Seq (Adey et al. Genome Research 24, 2041-2049 (2014) and Amini et al. Nature Genetics 46 1343-1349 (2014))), a microfluidic droplet (e.g. as in 10× Genomics (Zheng et al. Nature Biotechnology 34, 303-311 (2016))) or other compartmentalization reagents. Compartmentalization can be carried out with natively occurring spatially proximal nucleic acid molecules crosslinked to a solid substrate or bound to a solid substrate via the interaction of an affinity purification molecule and an affinity purification marker. Spatially proximal nucleic acid molecules crosslinked or bound to a common solid phase substrate can be captured in a droplet (thus compartmentalized). In some embodiments, compartmentalization does not require the spatially proximal nucleic acid molecules be associated with a solid substrate.

As used herein, the term "tagging" refers to physically integrating unique molecular identifiers (i.e. molecular barcodes, defined below) as part of (or in amplicons of) the nucleic acids which preserve spatial-proximal contiguity information. As described herein, molecular barcodes can be integrated into nucleic acids of interest using transposases to integrate a uniquely barcoded oligonucleotide into the nucleic acid molecule or, via techniques such as primer extension polymerization (PEP), where a polymerase and a primer comprising a molecular barcode anneals to and extends along the nucleic acid molecule, thereby creating amplicons of the nucleic acid molecule that are contiguous with the barcoded primer nucleic acids. Also described is an alternate form of tagging involving the ligation of an oligonucleotide comprising a molecular barcode to a terminal end(s) of a nucleic acid molecule. Tagging of the spatially proximal nucleic acid molecules can be carried out with the spatially proximal nucleic acid molecules associated with a solid substrate.

As used herein, the term "molecular barcode" refers to a uniquely identifiable nucleic acid sequence that uniquely informs the context for which the molecular barcode was introduced. For example, when a molecular barcode is integrated into a nucleic acid molecule and subsequently sequenced, the molecular barcode manifested in the sequencing readout informs about the compartment or virtual compartment with which the nucleic acid molecule was associated and thus contains spatial-proximal contiguity information.

Typically, after compartmentalization and tagging, the compartments (e.g., droplets) would be merged together (for example, droplets would burst and combine into a single intermixing sample) and any protein may be denatured (e.g. ProK treatment) to release the spatially proximal nucleic acid molecules from a solid substrate. The solid substrate (e.g., beads) could be removed magnetically, if the beads are magnetic, or pelleted, if the beads are not magnetic. The spatially proximal nucleic acid molecules would be purified using standard methods (e.g. ethanol precipitation, SPRI beads, Qiagen columns, etc.).

Regardless of the specific SSPC method, all SSPC methods capture spatial-proximal contiguity information in compartment-specific or virtual compartment-specific molecular barcode. Once the SSPC products are formed, the spatial-proximal contiguity information is detected using DNA sequencing, whereby two or more common molecular barcode sequences and the contiguous adjacent nucleic acids are sequenced (as described herein). With these sequence information, one is informed that the nucleic acid molecules adjoined to a common molecular barcode are natively spatially proximal nucleic acids.

Compartmentalization without a Solid Substrate

In some embodiments, reagents that preserve spatial-proximal contiguity information are reagents that compartmentalize and tag by attaching compartment-specific molecular barcodes (as previously described), in the absence of a solid substrate. In some embodiments, compartment-specific barcoded oligonucleotides are attached to natively spatially proximal nucleic acid molecules by ligation. In some embodiments, compartment-specific barcoded oligonucleotides are attached to natively spatially proximal nucleic acid molecules by primer extension reactions.

Figure 17:
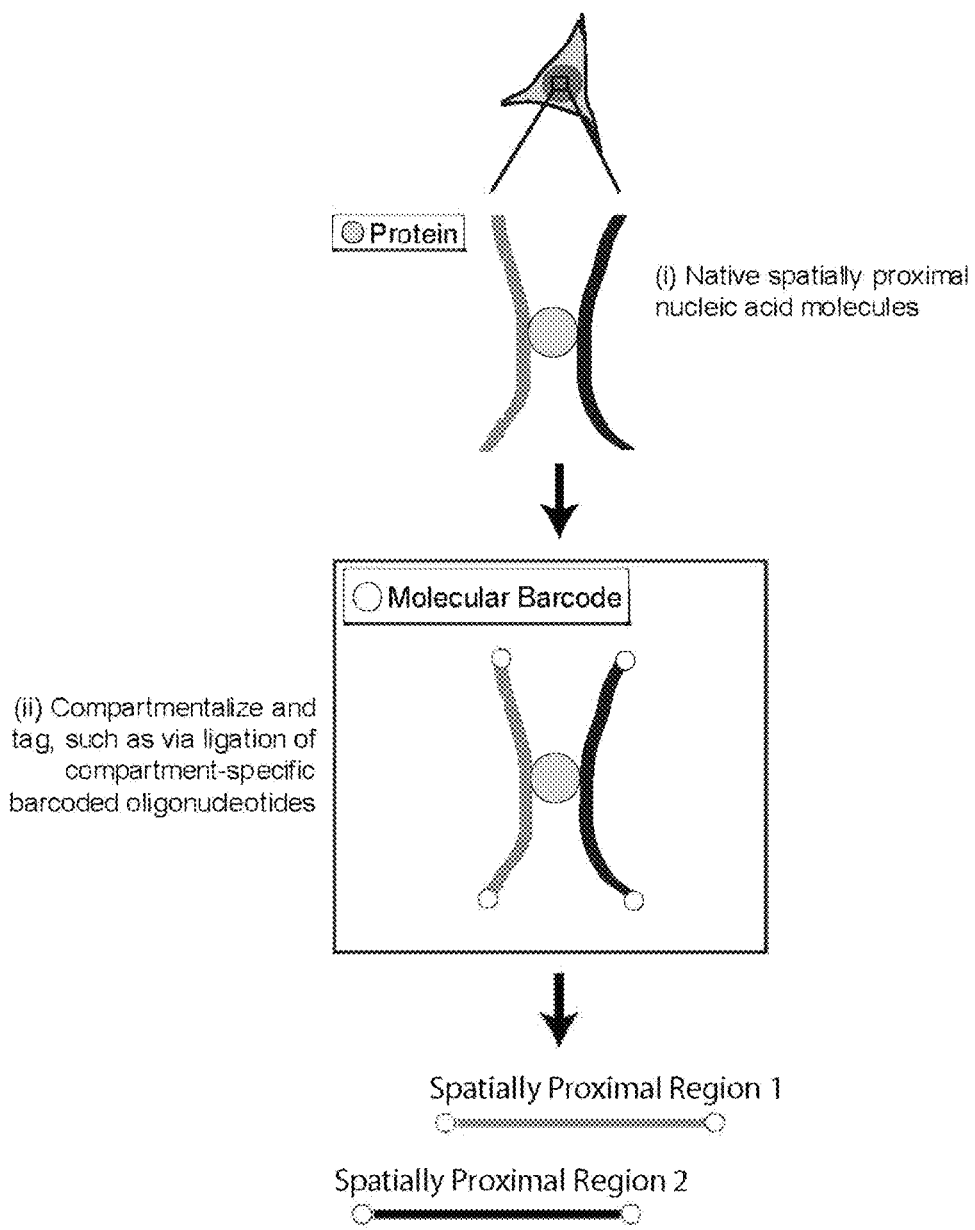
FIG. 17 illustrates capturing spatial-proximal contiguity information from FFPE samples via compartmentalization and tagging with compartment-specific molecular barcodes.

FIG. 17 illustrates capturing spatial-proximal contiguity information from FFPE samples via compartmentalization and tagging with compartment-specific molecular barcodes. In one embodiment of the method, the method begins with (i) native spatially proximal nucleic acids (nSPNAs), followed by (ii) compartmentalization of the crosslinked nSPNAs and introducing a compartment specific molecular barcode, such as ligating a compartment-specific barcoded oligonucleotide. Finally (iii), barcoded template molecules are purified and prepared as nucleic acid templates and are ready for sequencing, whereby the molecular barcode is the molecular identifier for which nSPNAs were spatially proximal.

Similar to the SSPC methods, spatial-proximal contiguity information is detected using DNA sequencing, whereby two or more common molecular barcode sequences and the contiguous adjacent nucleic acids are sequenced (as described herein). With these sequence information, one is informed that the nucleic acid molecules adjoined to a common molecular barcode are natively spatially proximal nucleic acids.

Tn5 Tetramer

In certain embodiments, reagents that preserve spatial-proximal contiguity information comprise a Tn5 tetramer (see Lai et al. Nature Methods. Vol. 15, September 2018, 741-747). Methods involving the use of the Tn5 tetramer (as described herein) capture spatial-proximal contiguity information in the form of Tn5-mediated looping products, whereby a physical link, mediated by the Tn5 linker oligonucleotide, is formed between two natively spatially proximal nucleic acids. Once the Tn5-mediated looping products are formed, the nucleic acid is released from Tn5 (see discussion above), the spatial-proximal contiguity information is detected using DNA sequencing, whereby the nucleic acids on both sides of a given Tn5 linker oligonucleotide are sequenced (as described herein). With these sequence information, one is informed that the nucleic acid molecules from a given Tn5-mediated looping product are natively spatially proximal nucleic acids. (see detailed description below)

In certain embodiments, one or more steps of the methods described herein is performed using automated equipment (see Example 19). In some embodiments, essentially all of the steps of the methods described herein are performed using automated equipment.

Sequencing

In certain embodiments, nucleic acids with preserved spatial-proximal contiguity information from formalin-fixed paraffin-embedded or deeply formalin-fixed samples, as described herein, are sequenced to produce sequence readouts. In some embodiments, sequencing is at a depth of 30× or less. In some embodiments, sequencing is at a depth of 15× or less, 10× or less, 5× or less, 1× or less, 0.75× or less, 0.5× or less, 0.1× or less, 0.05× or less or 0.01× or less.

Quality of DNA Templates

One metric for the quality of the DNA templates from FFPE samples or deeply formalin-fixed samples prepared utilizing the methods described herein when further analyzed by methods that preserve spatial-proximal contiguity information (e.g., proximity ligation methods, such as HiC) is the percent of long-cis readouts (long-range) readouts. In some embodiments, the criteria for assessing quality is that >40% of mapped de-duplicated reads represent long-range readouts of at least 15 kb. In some embodiments, depending on the properties of the sample, such as the extent of the archival period, the criteria may be lower than greater than 40%, such about 20 to 25% long-range readouts (see FIG. 25A). Such readouts enable identification of translocations at low sequencing depth (se FIGS. 25B-D). In some embodiments, the criteria is greater than 35%, 30%, 25%, 20% or 15% long-range readouts greater than 15 kb. In certain embodiments, the long range readout are defined as 100 kb-1 Mb, >20 kb, >10 kb, >5 kb, or >1 kb in length and the respective percent of long-range readouts will change depending on the definition of long-range readouts. DNA templates prepared from FFPE samples or deeply formalin-fixed samples utilizing the methods described herein result in a greater % of long-range readouts than when samples are prepared without utilizing the described methods for solubilizing and decompacting (e.g., contact with a denaturing detergent at a temperature greater than 65° C., contact with a denaturing detergent at a temperature greater than 65° C. for greater than 10 minutes, contact with a denaturing detergent at a temperature of 74° C. for 40 minutes, contact with a denaturing detergent at a temperature of about 62° C. for greater than 10 minutes, contact with a denaturing detergent at a temperature of 62° C. for 40 minutes).

In certain embodiments, other metrics to measure quality of the DNA templates include measurements of frequency, sensitivity, specificity, false positive rate, etc., for example when identifying translocations.

Reversal of Crosslinking

In certain embodiments, crosslinking is reversed by incubation with protease K (ProK) at a reduced temperature for a shortened period of time. In some embodiments, the temperature is less than 68° C. and the time is about 30 min. In some embodiments the temperature is about 55° C. In some embodiments the temperature is 55° C. (see Example 20).

In certain embodiments, crosslinking is reversed by incubating the sample at a temperature of about 95° C. for about 1 hour in the absence of proteinase K. In some embodiments, crosslinking is reversed by incubating the sample at a temperature of 95° C. for 1 hour in the absence of proteinase K.

Preparation of Samples with Protein:cfDNA Complexes

In some embodiments, a sample comprises protein:cfDNA (protein:cell-free DNA) complexes in solution. As used herein, the term "protein:cfDNA complexes" refers to protein:DNA complexes that are ex situ, i.e., not in a cell or nucleus. Protein:cfDNA complexes include but are not limited to, DNA wrapped around or associated with nuclear proteins such as nucleosomes (DNA wrapped around core of histone proteins), chromatosomes, transcription factors, or other nuclear proteins. In some embodiments a sample comprising protein:cfDNA complexes can be blood serum, blood plasma, urine or other bodily fluids.

In some embodiments, a sample comprising protein:cfDNA complexes is contacted with a solid phase. A solid phase or solid phase element can be any solid phase that can associate with protein:cfDNA complexes or can be functionalized to associate with protein:cfDNA complexes. In some embodiments a solid phase is a microplate or a bead.

In certain embodiments, the surface of the solid phase is functionalized so as to bind protein. In some embodiments, the solid phase is carboxylated. A solid phase can be functionalized with other suitable reagents able to bind to protein. In certain embodiments, the solid phase is a carboxylated bead or a carboxylated microplate. Native spatially proximal nucleic acid molecules in the form of protein:cfDNA co-bound to a solid phase element are crosslinked. In certain embodiments, protein:cfDNA complexes bound to a carboxylated solid phase are crosslinked to spatially and proximally bound protein:cfDNA complexes by contacting with a crosslinking reagent. In certain embodiments, a crosslinking reagent is formaldehyde. Other suitable crosslinking reagents can be utilized. In some embodiments, native spatially proximal nucleic acid molecules in the form of crosslinked protein:cfDNA co-bound to a solid phase element are released from the solid phase (e.g., by an amide hydrolysis reaction).

Figure 7:
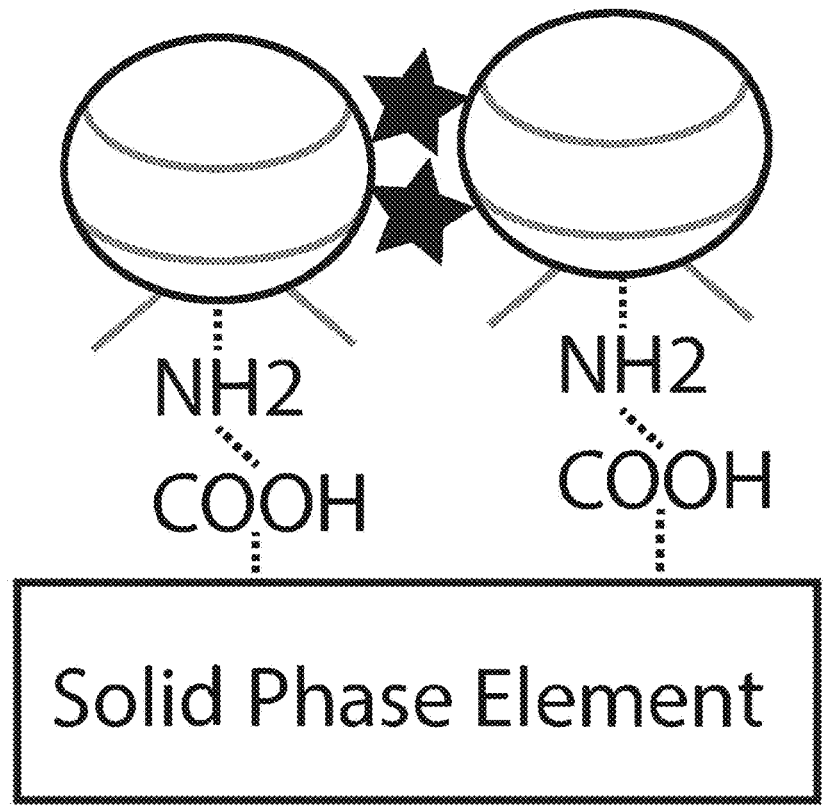
FIG. 7 illustrates protein:cfDNA complexes after binding to a carboxylated solid phase element and protein:cfDNA crosslinking.

FIG. 7 shows protein:cfDNA complexes after binding to a carboxylated solid phase element and undergoing protein:DNA crosslinking. In an embodiment, co-bound circulating protein:cfDNA complexes from blood plasma are immobilized to a carboxylated surface, which binds proteins (e.g. COOH—NH2), and then crosslinked to each other to hold nSPNAs (natively occurring spatially proximal nucleic acid molecules) in close spatial proximity. Binding to a solid phase element prior to crosslinking mitigates the chance of non-nSPNAs crosslinking to each other by randomly colliding in solution if standard crosslinking was performed. This approach also allows the washing away of free-floating cfDNA that is not bound to protein, because carboxylated surfaces only bind proteins.

In certain embodiments, protein:cfDNA complexes are associated with a solid phase coated with a crosslinking reagent and are crosslinked to the solid phase. In some embodiments, the crosslinking reagent is psoralen. Other nucleic acid crosslinking agents can be utilized.

Figure 8:
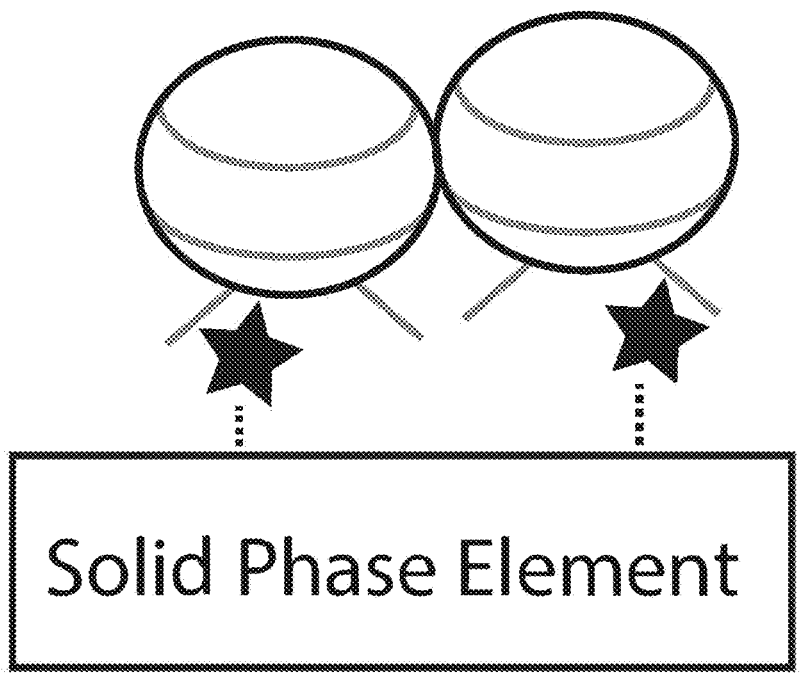
FIG. 8 illustrates protein:cfDNA complexes after crosslinking to a solid phase element coated with a nucleic acid crosslinking reagent.

FIG. 8 shows protein:cfDNA complexes after crosslinking to a solid phase element coated in a nucleic acid crosslinking agent. In an embodiment, co-bound protein:cfDNA complexes from blood plasma are immobilized to a solid phase element via nucleic acid crosslinking, which binds DNA of the protein:cfDNA complexes to its surface. Crosslinking mediated by binding to a solid phase mitigates the chance of non-nSPNAs crosslinking to each other by random chance in solution if standard crosslinking was performed. This approach also allows the removal of proteins, since the proteins can be degraded (e.g. Proteinase K treatment), while leaving the DNA bound to the solid phase element.

In some embodiments, the protein:cfDNA complexes, either crosslinked to one another or crosslinked to a solid phase are contacted with one or more reagents that preserve spatial-proximal contiguity information in the cell free DNA of the sample.

In certain embodiments, the one or more reagents that preserve spatial-proximal contiguity information comprise reagents that generate proximity ligated nucleic acid molecules. In some embodiments, an affinity purification marker is incorporated into the crosslinked protein:cfDNA complexes. In certain embodiments, the affinity purification marker is a biotinylated nucleotide. In some embodiments, the spatially proximal cell free DNA of the protein:cfDNA complexes is ligated to produce ligation products. In some embodiments, the ligation products are isolated. In some embodiments, the ligation products are isolated by affinity purification. In some embodiments, the affinity purification is biotin:streptavidin enrichment of ligation junctions. In certain embodiments, the ligation products do not contain an affinity purification marker (e.g., a biotinylated nucleotide) and are isolated by size selection. Size selection includes, but is not limited to, SPRI beads and gel purification. In certain embodiments, reagents that generate proximity ligated nucleic acid molecules comprise one or more of at least one restriction endonuclease, a DNA polymerase, a plurality of nucleotides comprising at least one biotinylated nucleotide, and a ligase. In some embodiments, there are two restriction endonucleases.

Figure 9:
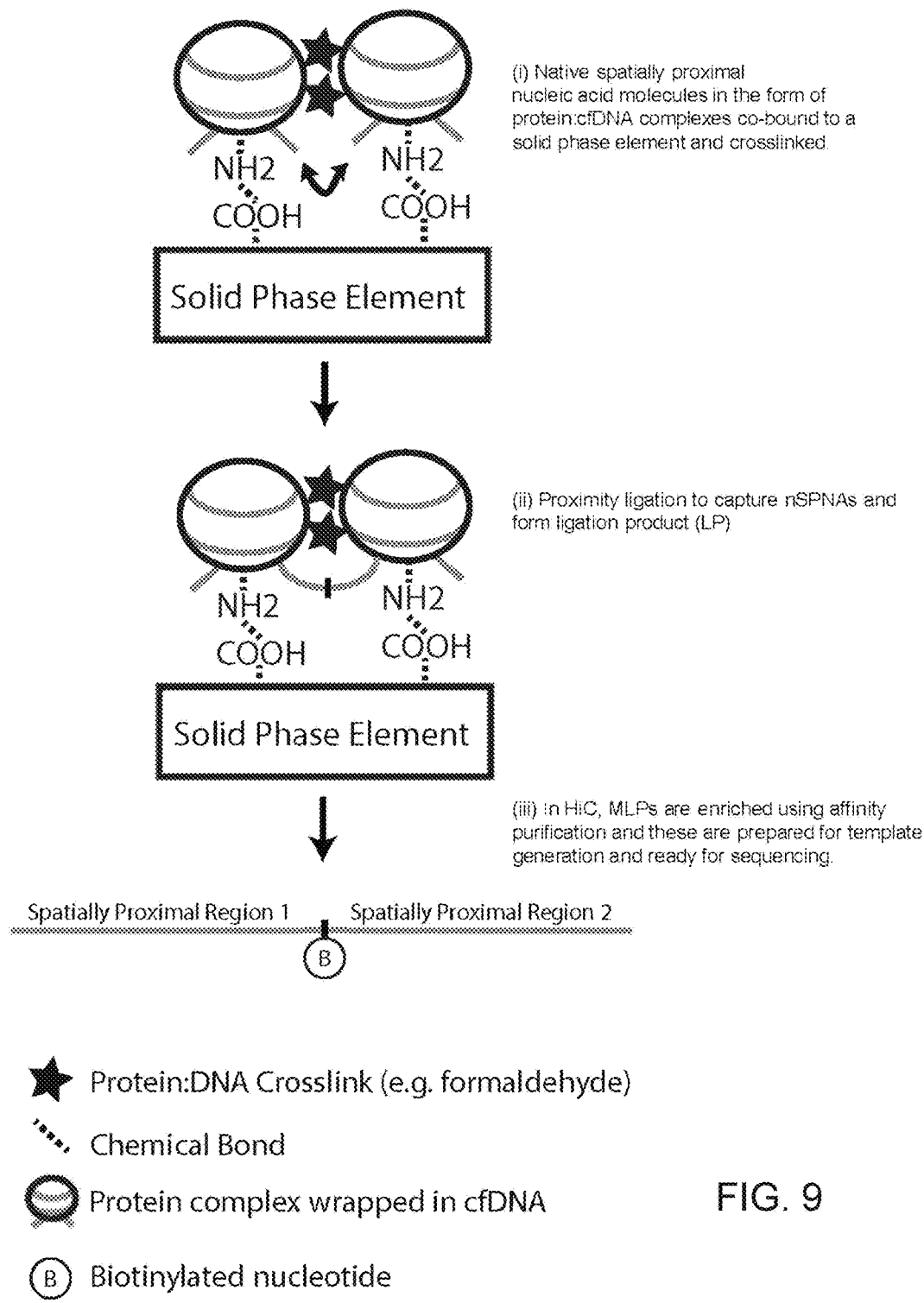
FIG. 9 illustrates capturing spatial-proximal contiguity information from protein:cfDNA complexes via proximity ligation.

FIG. 9 shows capturing spatial-proximal contiguity information via proximity ligation from protein:cfDNA complexes. In an embodiment of the method, (i) native spatially proximal nucleic acids (nSPNAs) from a cell-free nucleic acids source (e.g. blood plasma), are co-bound to a solid phase element and crosslinked. This is followed by (ii) proximity ligation to generate ligation products (LPs), which may have an affinity purification marker at the ligation junction (e.g. an incorporated biotinylated nucleotide). While HiC is depicted, PL methods are sub-classified as 3C-based and HiC-based and there are many specific variations of PL (as described herein). In HiC (iv), the cell-free nucleic acid ends are marked (e.g. biotinylated) and then ligated to create marked ligated products (MLPs, MLPs are a manifestation of LPs), bearing an affinity purification marker at the Us. After MLP generation, affinity purification is used to enrich for MLPs comprising Us and such fragments are prepared as nucleic acid templates and are ready for sequencing—i.e. the nucleic acids from the MLPs that contain at least an LJ are enriched and prepared as a template and sequenced in HiC, to deplete uMLPs (unligated MLPs that do not usually manifest Us).

Proximity ligation can also be utilized to preserve spatial-proximal contiguity information when protein:cfDNA complexes are crosslinked to a solid phase.

In certain embodiments, the one or more reagents that preserve spatial-proximal contiguity information comprise a Tn5 tetramer (see Lai et al. Nature Methods. Vol. 15, September 2018, 741-747). In some embodiments, the Tn5 tetramer has a biotinylated linker sequence. In some embodiments, the marked Tn5-mediated loops are isolated by affinity purification. In some embodiments, the affinity purification is biotin:streptavidin enrichment of the marked Tn5-mediated loops. In certain embodiments, Tn5-mediated loops are isolated by size selection. Size selection includes, but is not limited to, SPRI beads and gel purification.

Figure 10:
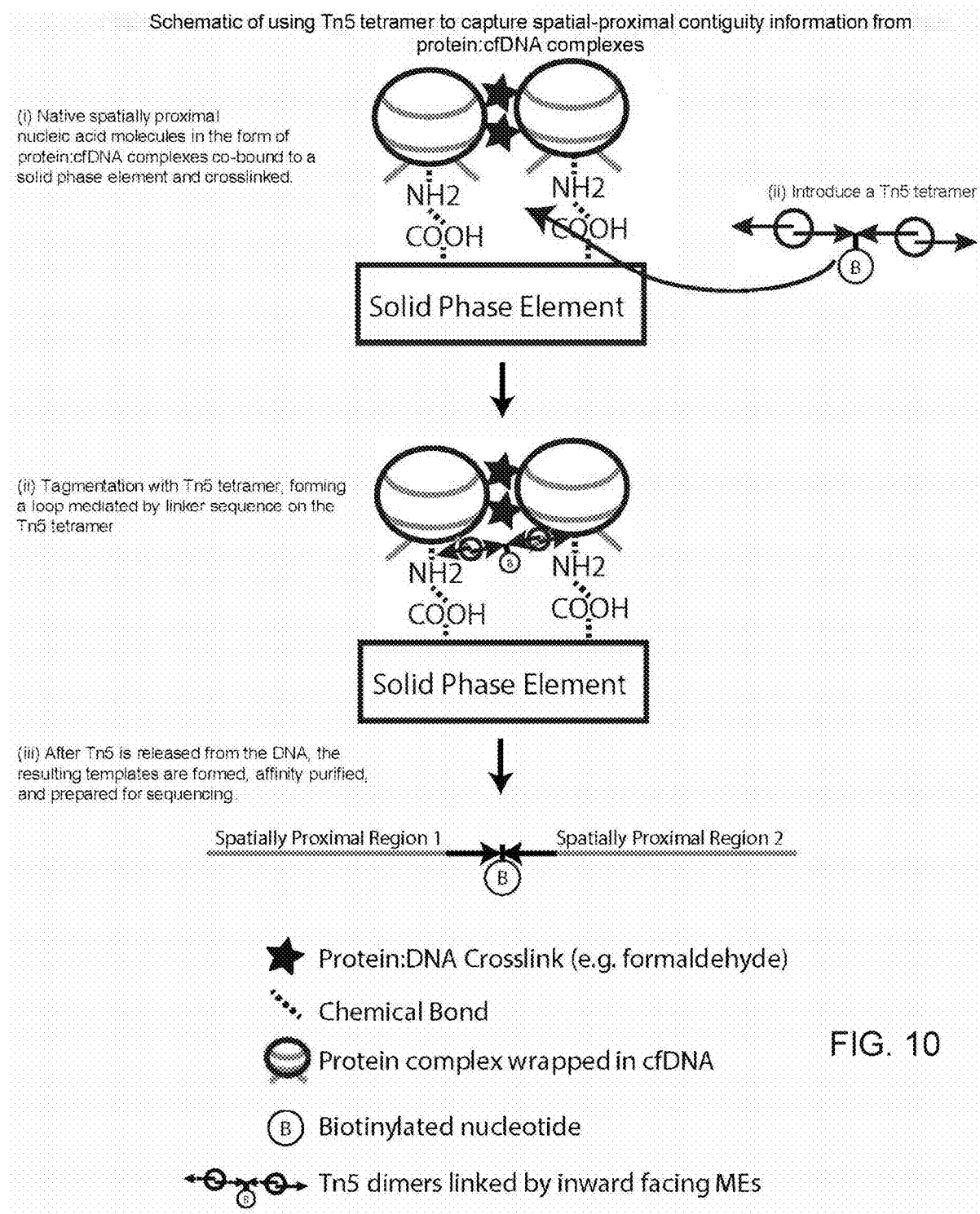
FIG. 10 illustrates using Tn5 tetramer to capture to capture spatial-proximal contiguity information from crosslinked protein:cfDNA complexes.

FIG. 10 shows capturing spatial-proximal contiguity information via Tn5-mediated looping from protein:cfDNA complexes bound to a solid phase. In an embodiment, (i) native spatially proximal nucleic acids (nSPNAs) from a cell-free nucleic acids source (e.g. blood plasma), are co-bound to a solid phase element and crosslinked. Followed by (ii) introduction of a Tn5 tetramer, comprising two Tn5 dimers linked by a linker sequence comprising inward facing mosaic end (ME) sequences. Then (iii), tagmentation by the Tn5 tetramer on both co-bound protein:cfDNA complexes creates an oligonucleotide link between the nSPNAs, with biotin marking the successful co-tagmentation events. Finally (iv), once fragments are separated from Tn5, affinity purification is used to enrich for marked Tn5-mediated loops and fragments prepared as nucleic acid templates and are ready for sequencing.

Figure 11:
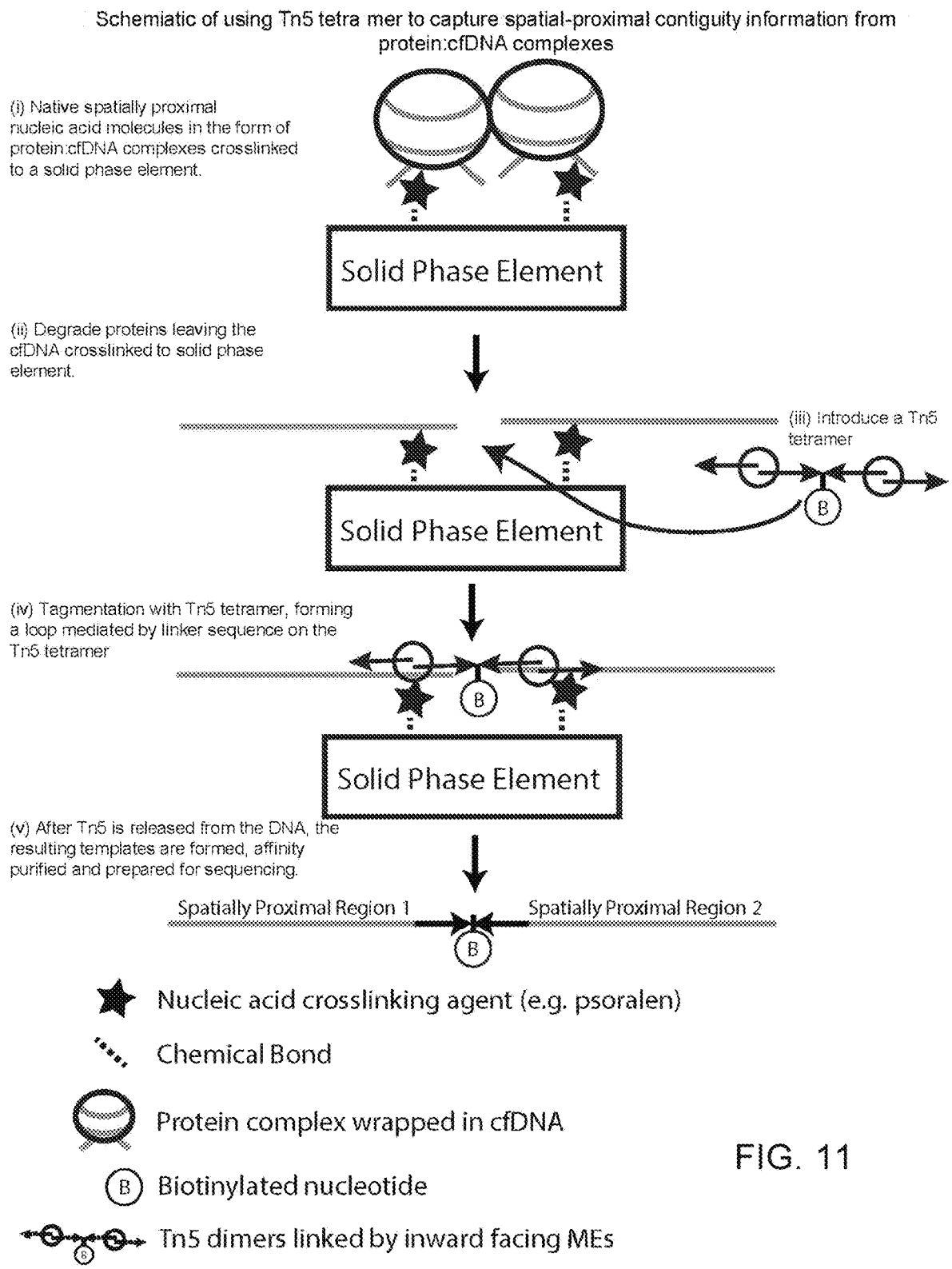
FIG. 11 illustrates using Tn5 tetramer to capture spatial-proximal contiguity information for cell free nucleic acids crosslinked to solid phase element (e.g., via psoralen).

FIG. 11 shows capturing spatial-proximal contiguity information via Tn5-mediated looping from protein:cfDNA complexes crosslinked to a solid phase element. In an embodiment, (i) native spatially proximal nucleic acids (nSPNAs) from a cell-free nucleic acids source (e.g. blood plasma), are crosslinked to a solid phase element. This is followed by (ii) degrading of proteins, leaving cfDNA crosslinked to the solid phase element. Then (iii) introduction of a Tn5 tetramer, comprising two Tn5 dimers linked by a linker sequence comprising inward facing mosaic end (ME) sequences. Then (iv), tagmentation by the Tn5 tetramer on both co-crosslinked cfDNA molecules creates an oligonucleotide link between the nSPNAs, with biotin marking the successful co-tagmentation events. Finally (v), affinity purification is used to enrich for marked Tn5-mediated loops and such fragments are prepared as nucleic acid templates and are ready for sequencing.

In some embodiments, the one or more reagents that preserve spatial-proximal contiguity information in the cell free DNA of the sample are used with methods in which the native spatially proximal nucleic acids (nSPNAs) from a cell-free nucleic acids source (e.g. blood plasma), are bound to a solid phase element (not crosslinked to the solid phase element). Reagents may include one or more of at least one restriction endonuclease, a DNA polymerase, a plurality of nucleotides comprising at least one biotinylated nucleotide, a ligase and a Tn5 tetramer with a biotinylated linker sequence.

In some embodiments, the one or more reagents that preserve spatial-proximal contiguity information comprise reagents that compartmentalize the cell-free DNA protein complexes released from a solid support and tag the compartmentalized cell-free DNA protein complexes with a compartment-specific barcoded oligonucleotide. In some embodiments, tagging is by ligating on a compartment-specific barcoded sequencing adaptor. In some embodiments, tagging is by annealing and extending using a compartment specific barcoded primer. In some embodiments, tagging is by a transposome carrying a compartment-specific molecular barcode. Reagents may include one or more of a liquid droplet generator, a barcoded oligonucleotide, a ligase, a DNA polymerase, and nucleotides.

Figure 12:
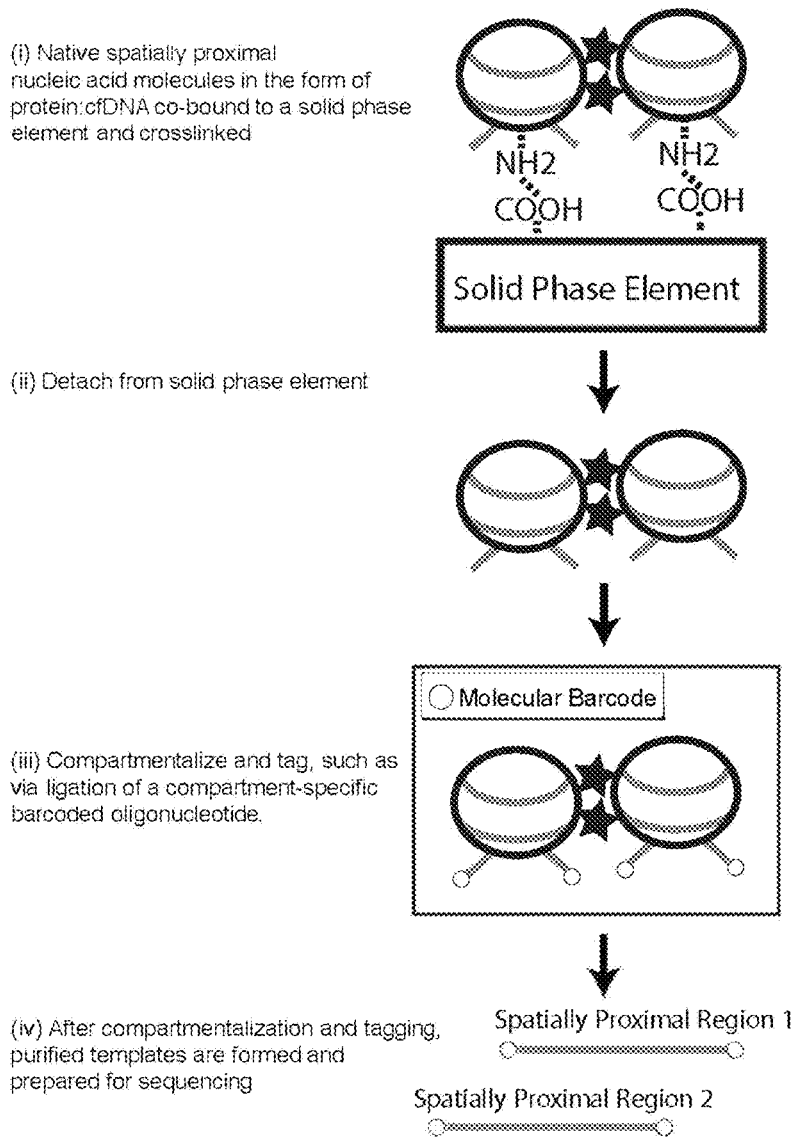
FIG. 12 illustrates capturing spatial-proximal contiguity information from protein:cfDNA complexes via compartmentalization and tagging with compartment-specific molecular barcodes.

FIG. 12 shows capturing spatial-proximal contiguity information from protein:cfDNA complexes via compartmentalization and tagging with compartment-specific molecular barcodes. In an embodiment, (i) native spatially proximal nucleic acids (nSPNAs) from a cell-free nucleic acids source (e.g. blood plasma), are co-bound to a solid phase element and crosslinked. Followed by (ii) detachment of the crosslinked protein:cfDNA complex from the solid phase element. Then (iii) compartmentalization of the crosslinked protein:cfDNA complexes and introducing a compartment-specific molecular barcode, such as ligating a compartment-specific barcoded oligonucleotide. Finally (v), barcoded template molecules are purified and prepared as nucleic acid templates and are ready for sequencing, whereby the molecular barcode is the molecular identifier for which nSPNAs were spatially proximal.

In some embodiments, the one or more reagents that preserve spatial-proximal contiguity information comprise reagents that affinity purify the protein:cfDNA complexes, compartmentalize the affinity purified protein:cfDNA complexes and tag the compartmentalized protein:cfDNA complexes with a compartment specific molecular barcode. In some embodiments, tagging is by ligating on a compartment-specific barcoded sequencing adaptor. In some embodiments, tagging is by annealing a compartment specific barcoded PCR primer and extending the primer. In some embodiments, tagging is by a transposome carrying a compartment-specific molecular barcode.

FIG. 13 shows capturing spatial-proximal contiguity information from protein:cfDNA complexes via compartmentalization with solid phase element and tagging with compartment-specific molecular barcodes. In an embodiment, (i) native spatially proximal nucleic acids (nSPNAs) from a cell-free nucleic acids source (e.g. blood plasma), are co-bound to a solid phase element and crosslinked. This is followed by (ii) detachment of the crosslinked protein:cfDNA complex from the solid phase element. Then (iii) affinity purification, such as with streptavidin coated beads, followed by compartmentalization of the crosslinked protein:cfDNA complexes bound to the solid phase element whereby a compartment-specific molecular barcode is tagged to the cfDNA. Finally (iv), barcoded template molecules are purified and prepared as nucleic acid templates and are ready for sequencing, whereby the molecular barcode is the molecular identifier for which nSPNAs were spatially proximal.

In some embodiments, the one or more reagents that preserve spatial-proximal contiguity information comprise Tn5 bound to a solid phase. In some embodiments, the solid phase is a bead. In certain embodiments, the Tn5 comprises a virtual compartment-specific molecular barcode.

FIG. 14 shows capturing spatial-proximal contiguity information from protein:cfDNA complexes via virtual compartmentalization using bead-linked transposome carrying a virtual compartment-specific molecular barcode. In an embodiment, (i) native spatially proximal nucleic acids (nSPNAs) from a cell-free nucleic acids source (e.g. blood plasma), are co-bound to a solid phase element and crosslinked. This is followed by (ii) detachment of the crosslinked protein:cfDNA complex from the solid phase element. Then (iii) tagmentation with bead-linked transposome carrying unique molecular barcodes, thereby creating virtual compartments. Finally (iv), barcoded template molecules are purified and prepared as nucleic acid templates and are ready for sequencing, whereby the molecular barcode is the molecular identifier for which nSPNAs were spatially proximal.

Data Analysis/Applications

Nucleic acids from FFPE samples, deeply formalin-fixed samples or samples comprising protein:cfDNA complexes prepared by methods described herein, in conjunction with proximity ligation methods (e.g., HiC, 3C, 4C, 5C) or other methods that capture spatial-proximal contiguity information generate contiguity-preserved sequencing data for applications, such as haplotype phasing and genomic rearrangement detection For example, Selvaraj et al. BMC Genomics (2015), Selvaraj et al, Nature Biotechnol (2013), and PCT/US2014/047243 described HiC data for haplotype phasing and Engreitz et al. (PLOS ONE September 2012/Volume 7/Issue 9/e44196) has described HiC data for genomic rearrangement analysis in human disease. Several other papers have described using HiC data for genomic rearrangement detection (Dixon et al. Nature Genetics (2018); Chakraborty and Ay, Bioinformatics (2018); Harewood et al. Genome Biology (2017). One such analysis tool for rearrangement detection is HiC-Breakfinder tool (https://github.com/dixonlab/hic_breakfinder) from Dixon et al, Nature Genetics, 2018. For example, as described in Example 21 FFPE-HiC data can be used be used to identify a translocation in samples exhibiting a range of mutant allele frequencies (50% to 10%) and at different sequencing depths (15×, 5× and 1×). Also, as described in Example 22, translocations can be detected by applying Capture-HiC to processed FFPE samples for which a breakpoint is not captured by a capture sequencing probe. Other contiguity-preservation-enabled analyses and applications include, but are not limited to, de novo genome and metagenome assembly, structural variation detection, and others.

Experiments demonstrating the value of the described protocols for preparing FFPE tumor tissue samples in conjunction with HiC for the discovery of translocations in tumor tissue samples are described in Example 23 and Example 24.

Methylation

In some embodiments the nucleic acids with preserved spatial-proximal contiguity information generated by the methods described herein are contacted with a bisulfite reagent prior to PCR and sequencing to enable the concurrent analysis of spatial proximity and DNA methylation at base resolution. In some embodiments the bisulfite reagent is sodium bisulfite.

In some embodiments HiC ligation products are generated using a HiC protocol as previously described (Rao et al, Cell, 2014, Li et al, Biorxiv 2018). DNA is sheared to an approximate length of 400 bp, and ligation junction are enriched using streptavidin beads. Illumina library construction ensues while the DNA is attached to the streptavidin bead, as previously described (Rao et al, Cell, 2014). Directly after adapter ligation, DNA is subject to bisulfite conversion, using methods known in the art. Unmethylated lambda DNA is spiked in at 0.5% prior to bisulfite conversion in order to estimate the conversion rate. The bisulfite converted DNA is purified, amplified, and sequenced.

In some embodiments sheared HiC ligation products are treated with a bisulfite reagent and purified (Stamenova, Biorxiv, 2018). Ligation junctions are then enriched using streptavidin beads. DNA is then detached from the beads, and prepared as a sequencing library using techniques known in the art for converting ssDNA into a dsDNA sequencing library. Adapter ligated molecules are then subject to library amplification and sequencing.

Methods of bisulfite conversion or derivations of these methods can be applied to nucleic acids molecules comprising spatial-proximal contiguity information obtained from FFPE, deeply fixed, or protein:cfDNA samples using the methods described herein (e.g., proximity ligation, solid substrate-mediated proximity capture (SSPC), compartmentalization and tagging an and use of a Tn5 tetramer).

After sequencing, methods known to the art can be used to analyze the data in the context of spatial-proximity and long-range sequence contiguity, such as but not limited to using the spatial proximal contiguity information to inform genome folding patterns (Lieberman-Aiden, Science, 2009), and genomic rearrangement analysis (Dixon et al, Nature Genetics, 2018). Similarly, methods known to the art can also be applied to analyze the DNA methylation status (Lister et al, Nature, 2009; Shultz et al, Nature, 2015). Additionally, methods known in the art can also be applied to concurrently analyze the DNA methylation status with respect to 3D genome folding (Li et al, Biorxiv 2018; Stamenova, Biorxiv, 2018), revealing DNA chemical modifications properties and DNA folding patterns in parallel. Specifically in the context of applying this method to protein:cfDNA complexes, it is well known in the art that DNA methylation status of cell free nucleic acids can inform tissue of origin analyses as well as several other cfDNA analysis, including but not limited to the non-invasive detection of tumor DNA, prenatal diagnoses, and organ transplantation monitoring (Zeng et al, Journal of Genetics and Genomics, 2018; Lehmann-Werman et al, PNAS, 2016). Moreover, similar to DNA methylation status, DNA folding patterns are also tissue-type specific, and thus HiC signal obtained from cfDNA:protein complexes may also aid in such non-invasive cfDNA analyses such as cancer diagnoses and organ transplantation monitoring. Also, because it is known that HiC signal uniquely captures long-range sequence contiguity information to significantly enhance genomic rearrangement analyses (Dixon et al, Nature Genetics, 2018), HiC applied to cfDNA:protein complexes could enrich for such genomic rearrangement signal from liquid biopsy samples and greatly benefit early non-invasive cancer diagnoses. And finally, the combination and concurrent analysis of both DNA methylation and DNA spatial proximity and long-range contiguity will synergize to better enable the analyses described herein.

Kits

In some embodiments, provided are kits for carrying out methods described herein. Kits often comprise one or more containers that contain one or more components described herein. A kit comprises one or more components in any number of separate containers, packets, tubes, vials, multi-well plates and the like, or components may be combined in various combinations in such containers. Kit components and reagents are as described herein.

One or more of the following components, for example, may be included in a kit: (i) one or more dewaxing reagents (e.g., xylene, mineral oil, etc); (ii) one or more lysis buffers (e.g., lysis buffer with one or more salts, a protease inhibitor and a non-ionic, non-denaturing detergent, etc); (iii) one or more denaturing detergents (e.g., sodium dodecyl sulfate, etc.); (iv) one or more reagents to quench a denaturing detergent (e.g. TritonX-100, etc.), (v) one or more extracellular matrix proteases (e.g., a collagenase and/or a dispase, ColI, ColIII, ColIV, Dispase I, etc.); (vi) one or more reagents that preserve spatial-proximal contiguity information and (vii) printed matter (e.g. directions, labels, etc). In some embodiments, a kit comprises one or more reagents that preserve spatial-proximal contiguity information that generate proximity ligated nucleic acid molecules (e.g., a restriction endonuclease or two restriction endonucleases, a DNA polymerase, a plurality of nucleotides comprising at least one biotinylated nucleotide, and a ligase, etc.). In some embodiments, a kit comprises one or more reagents that preserve spatial-proximal contiguity information comprising solid phase elements (e.g., beads, solid phase substrates functionalized with a nucleic acid crosslinking reagent, such as psoralen, solid phase substrates functionalized with an affinity purification molecule, such as streptavidin, and an affinity purification marker, such as biotin, solid phase substrates functionalized with a transposase, such as Tn5, comprising a barcoded oligonucleotide. In some embodiments, a kit comprises one or more reagents that preserve spatial-proximal contiguity information comprising compartmentalization reagents and compartment-specific molecular barcodes. In some embodiments, a kit comprises one or more reagents that preserve spatial-proximal contiguity information comprising a Tn5 tetramer (e.g., a Tn5 tetramer that comprises a biotinylated linker sequence). In some embodiments, a kit comprises a surface on which the methods described herein are carried out, in whole or part, (e.g., a pathology slide, etc.).

In some embodiments, a kit does not include one or more dewaxing reagents.

One or more of the following components, for example, may be included in a kit: (i) a solid phase and (ii) one or more reagents that preserve spatial-proximal contiguity information. In some embodiments, a kit comprises a solid phase that comprises a carboxylated surface (e.g., a microplate, a bead, etc.). In some embodiments, a kit comprises a solid phase (e.g., a magnetic bead, etc.) that is coated with a cross-linking reagent (e.g., psoralen, etc.). In some embodiments, a kit comprises one or more reagents that preserve spatial-proximal contiguity information that generate proximity-ligated nucleic acid molecules (e.g., a restriction endonuclease or two restriction endonucleases, a DNA polymerase, a plurality of nucleotides sometimes comprising at least one biotinylated nucleotide, and a ligase, etc.). In some embodiments, a kit comprises compartmentalization reagents (e.g., a microfluidic compartmentalization device that produces microfluidic droplets or microtiter plate wells into which complexes are diluted), compartment-specific molecular barcodes and one or more reagents to attach barcodes to preserve spatial-proximal contiguity information (e.g., reagents for primer extension polymerization (PEP), reagents for ligation or a transposase comprising a barcoded oligonucleotide).

In some embodiments, a kit comprises one or more reagents to affinity purify native spatially proximal nucleic acids in the form of protein:cfDNA complexes prior to compartmentalization (e.g., an affinity purification marker such as a biotinylated nucleotide and an affinity purification molecule such as streptavidin). In some embodiments, a kit comprises one or more reagents that preserve spatial-proximal contiguity information comprising a Tn5 tetramer (e.g., a Tn5 tetramer that comprises a biotinylated linker sequence). In some embodiments, a kit comprises one or more reagents that preserve spatial-proximal contiguity information comprise a bead-linked transposome (e.g., Tn5, etc.) comprising a compartment-specific barcoded oligonucleotide.

In some embodiments, a kit comprises a bisulfite reagent. In some embodiments, the bisulfite reagent is sodium bisulfite.

A kit sometimes is utilized in conjunction with a process, and can include instructions for performing one or more processes and/or a description of one or more compositions. A kit may be utilized to carry out a process described herein. Instructions and/or descriptions may be in tangible form (e.g., paper and the like) or electronic form (e.g., computer readable file on a tangle medium (e.g., compact disc) and the like) and may be included in a kit insert. A kit also may include a written description of an internet location that provides such instructions or descriptions.

EXAMPLES

The examples set forth below illustrate certain embodiments and do not limit the technology.

Example 1: Preparation of Formalin-Fixed Paraffin Embedded (FFPE) Samples

De-Waxing and Re-Hydration
1. Collect FFPE tissue sections (e.g., 5-10 um in thickness) from an FFPE block or FFPE slide. Transfer FFPE section to clean 1.5 ml tube.
2. Add 1 mL of xylene solution and incubate for 10 min. at RT.
3. Centrifuge at 17,860×g (15,000 rpm) for 5 min. at RT
4. Resuspend the deparaffinized tissue in 1 mL of 100% ethanol and incubate for 10 min. at RT
5. Centrifuge at 17,860×g for 5 min. at RT
6. Resuspend the deparaffinized tissue in 1 mL of water and incubate for 10 min. at RT
7. Centrifuge at 17,860×g for 5 min. at RT
ECM Protease Dissociation (Optional)
Example tissue dissociation buffers (all diluted in 1×PBS, pH=7.4):
Buffer 1: 0.05% Collagenase III
Buffer 2: 0.05% Collagenase IV
Buffer 3: 0.025% Collagenase IV+0.025% Dispase I (Neutral Protease I)
Buffer 4: 0.1% Collagenase I+0.025% Dispase I (Neutral Protease I)
Buffer 5: 0.05% Dispase I (Neutral Protease)
8. Add 1 mL of enzymatic tissue dissociation buffer (see above) and incubate for ~20 min at 37° C.
9. Centrifuge at 1,000×g for 10 min at RT and remove supernatant.
10. Add 200 uL of lysis buffer as described herein and incubate at 4° C. for 20 min and vortex every 4 minutes throughout the incubation.
11. Spin down at 1000×g and remove supernatant.
12. Resuspend sample in 1× Tris.
13. Add SDS to a final concentration of 0.5% and incubate at 74° C. for 40 min.
14. Add TritonX-100 to a final 10:1 v/v concentration relative to SDS, incubate at 37° C. for 15 min.

Prepare proximity ligation products, solid substrate-mediated proximity capture (SSPC) products, compartmentalized and tagged products or Tn5 tetramer products for use in DNA sequencing as described herein.

Example 2: Alternative Method for Preparation of Formalin-Fixed Paraffin-Embedded (FFPE) Samples (No De-Waxing and Rehydrating)

1. Collect FFPE tissue sections (e.g., 5-10 um in thickness) from an FFPE block or FFPE slide. Transfer FFPE section to clean 1.5 ml tube.
2. Add 200 uL of lysis buffer as described herein and incubate at 4° C. for 20 min and vortex every 4 minutes throughout the incubation.
3. Spin down at 1000×g and decant supernatant.
4. Resuspend sample in 1× Tris.
5. Add SDS to a final concentration of 0.5% and incubate at 74° C. for 40 min.
6. Add TritonX-100 to a final 10:1 v/v concentration relative to SDS, incubate at 37° C. for 15 min.

Prepare proximity ligation products, solid substrate-mediated proximity capture (SSPC) products, compartmentalized and tagged products or Tn5 tetramer products for use in DNA sequencing as described herein.

Example 3: FFPE—De-Waxing/Rehydration, No Cell Lysis, SDS Step, with/without Enzymatic Tissue Dissociation De-Waxing and Re-Hydration 1. Collect FFPE tissue sections (e.g. 5-10 um in thickness) from an FFPE block or FFPE slide. Transfer FFPE section to clean 1.5 ml tube.
2. Add 1 mL of xylene solution and incubate for 10 min. at RT.
3. Centrifuge at 17,860×g (15,000 rpm) for 5 min. at RT
4. Resuspend the deparaffinized tissue in 1 mL of 100% ethanol and incubate for 10 min. at RT
5. Centrifuge at 17,860×g for 5 min. at RT
6. Resuspend the deparaffinized tissue in 1 mL of water and incubate for 10 min. at RT
7. Centrifuge at 17,860×g for 5 min. at RT ECM Protease Dissociation (Optional)

Example tissue dissociation buffers (all diluted in 1×PBS, pH=7.4):

Buffer 1: 0.05% Collagenase III

Buffer 2: 0.05% Collagenase IV

Buffer 3: 0.025% Collagenase IV+0.025% Dispase I (Neutral Protease I)

Buffer 4: 0.1% Collagenase I+0.025% Dispase I (Neutral Protease I)

Buffer 5: 0.05% Dispase I (Neutral Protease)

8. Add 1 mL of enzymatic tissue dissociation buffer (see above) and incubate for ~20 min at 37° C.
9. Centrifuge at 1,000×g for 10 min at RT and remove supernatant.
10. Resuspend sample in 1× Tris.
11. Add SDS to a final concentration of 0.5% and incubate at 74° C. for 40 min.
12. Add TritonX-100 to a final 10:1 v/v concentration relative to SDS, incubate at 37° C. for 15 min.

Prepare proximity ligation products, solid substrate-mediated proximity capture (SSPC) products, compartmentalized and tagged products or Tn5 tetramer products for use in DNA sequencing as described herein.

Example 4—FFPE—(without De-Waxing/Rehydration), No Cell Lysis, SDS Step, No Enzymatic Tissue Dissociation 1. Collect FFPE tissue sections (e.g. 5-10 um in thickness) from an FFPE block or FFPE slide. Transfer FFPE section to clean 1.5 ml tube.
2. Resuspend sample in 1× Tris.
3. Add SDS to a final concentration of 0.5% and incubate at 74° C. for 40 min.
4. Add TritonX-100 to a final 10:1 v/v concentration relative to SDS, incubate at 37° C. for 15 min.

Prepare proximity ligation products, solid substrate-mediated proximity capture (SSPC) products, compartmentalized and tagged products or Tn5 tetramer products for use in DNA sequencing as described herein.

Example 5: Deeply Formalin-Fixed Sample (Pulverize, with/without Enzyme Dissociation, Lysis, SDS)

1. Pulverize tissue on dry ice with liquid nitrogen, mortar and pestle.
2. Transfer tissue to clean 1.5 mL microcentrifuge tube.

ECM Protease Dissociation (Optional)

Example tissue dissociation buffers (all diluted in 1×PBS, pH=7.4):

Buffer 1: 0.05% Collagenase III

Buffer 2: 0.05% Collagenase IV

Buffer 3: 0.025% Collagenase IV+0.025% Dispase I (Neutral Protease I)

Buffer 4: 0.1% Collagenase I+0.025% Dispase I (Neutral Protease I)

Buffer 5: 0.05% Dispase I (Neutral Protease)

3. Add 1 mL of enzymatic tissue dissociation buffer (see above) and incubate for ~20 min at 37° C.
4. Centrifuge at 1,000×g for 10 min at RT and remove supernatant.
5. Add 200 uL of lysis buffer as described herein and incubate at 4° C. for 20 min and vortex every 4 minutes throughout the incubation.
6. Spin down at 1000×g and decant supernatant.
7. Resuspend sample in 1× Tris.
8. Add SDS to a final concentration of 0.5% and incubate at 74° C. for 40 min.
9. Add TritonX-100 to a final 10:1 v/v concentration relative to SDS, incubate at 37° C. for 15 min.

Prepare proximity ligation products, solid substrate-mediated proximity capture (SSPC) products, compartmentalized and tagged products or Tn5 tetramer products for use in DNA sequencing as described herein.

Example 6: Protein:cfDNA Spatial-Proximal Contiguity Preservation

Plasma Isolation:
1. Collect blood into blood collection tube (BCT).
2. Isolate plasma, containing protein/cfDNA complexes.

Crosslinking Methods:

Using a Carboxylated Surface
1. Bind the proteins of the protein:cfDNA complexes to a carboxylated surface, such as a carboxylated bead or carboxylated microplate surface.
2. Wash away free-floating cfDNA, leaving behind only protein:cfDNA complexes bound to the carboxylated surface.
3. Crosslink the protein to cfDNA, such as using formaldehyde.

Using a Solid Phase Element Coated with a Crosslinking Reagent
1. Crosslink protein:cfDNA complexes to a solid phase element coated in a crosslinking reagent, e.g., a magnetic bead coated in a nucleic acid crosslinking reagent, such as psoralen.
2. Optional: Degrade proteins, such as using Proteinase K, leaving the cfDNA crosslinked to the solid phase element.

If Capturing Spatial-Proximal Contiguity Information Via Proximity Ligation:
1. Blunt ends of cfDNA
   a. Optionally incorporate an affinity purification marker, such as a biotinylated nucleotide.
2. Ligate spatially proximal cfDNA, producing ligation products.

3. Isolate ligation products by either:
   a. Affinity purification (e.g. biotin:streptavidin enrichment of the ligation junctions)
   b. Size selection—unligated cfDNA fragments are 100-240 bp, so any proximally ligated cfDNA molecules must be >240 bp and can be purified via SPRI beads, gel purification, etc.

If Capturing Spatial-Proximal Contiguity Information Via Tn5 Tetramer:
1. Add Tn5 tetramer to tagment the spatially proximal cfDNA, creating a physical link (or "loop") between two spatially proximal cfDNA fragments via an oligonucleotide linker sequence and thereby producing Tn5-mediating loop products.
   a. Optionally use a biotinylated linker sequence.
2. Isolate spatially linked products by either:
   a. Affinity purification (e.g. biotin:streptavidin enrichment of the biotinylated linker)
   b. Size selection—typical cfDNA fragments are 100-240 bp, so any Tn5 mediating loop products must be >240 bp and can be purified via SPRI beads, gel purification, etc.

If Capturing Spatial-Proximal Contiguity Information Via Compartmentalizing the Crosslinked Protein:cfDNA Complexes (without a Solid Phase Element) and Tagging with a Compartment Specific Molecular Barcode:
1. Release (i.e. unbind) crosslinked protein:cfDNA complexes, such as from the carboxylated surface.
2. Physically compartmentalize protein:cfDNA complexes, such as in a liquid droplet.
3. Tag cfDNA within each compartment with a compartment-specific molecular barcode
   a. For example, ligating a compartment-specific barcoded sequencing adapter or annealing a compartment specific barcoded PCR primer.

If Capturing Spatial-Proximal Contiguity Information Via Compartmentalizing the Crosslinked Protein:cfDNA Complexes (with a Solid Phase Elements) and Tagging with a Compartment Specific Molecular Barcode:
1. Blunt ends of cfDNA and incorporate an affinity purification marker, such as a biotinylated nucleotide.
2. Release (i.e. unbind) crosslinked protein:cfDNA complexes, such as from the carboxylated surface.
3. Affinity purify protein:cfDNA complexes, for example using streptavidin-coated beads.
4. Physically compartmentalize protein:cfDNA complexes bound to a solid phase element, such as in a liquid droplet.
5. Tag cfDNA within each compartment with a compartment-specific molecular barcode
   a. For example, ligating a compartment-specific barcoded sequencing adapter or annealing a compartment specific barcoded PCR primer.

If Capturing Spatial-Proximal Information Via Virtually Compartmentalizing the Cross Linked Protein:cfDNA Complexes by Tagging with a Unique Molecular Barcode, Mediated by Tn5 Bound to a Solid Phase Element (a "Bead-Linked Transposome"):
1. Release (i.e. unbind) crosslinked protein:cfDNA complexes, such as from the carboxylated surface.
2. Add uniquely barcoded bead-linked transposomes.
3. Tag cfDNA from the same protein:cfDNA complex with the same molecular barcode using tagmentation from the bead-linked transposome.

Figure 1A:
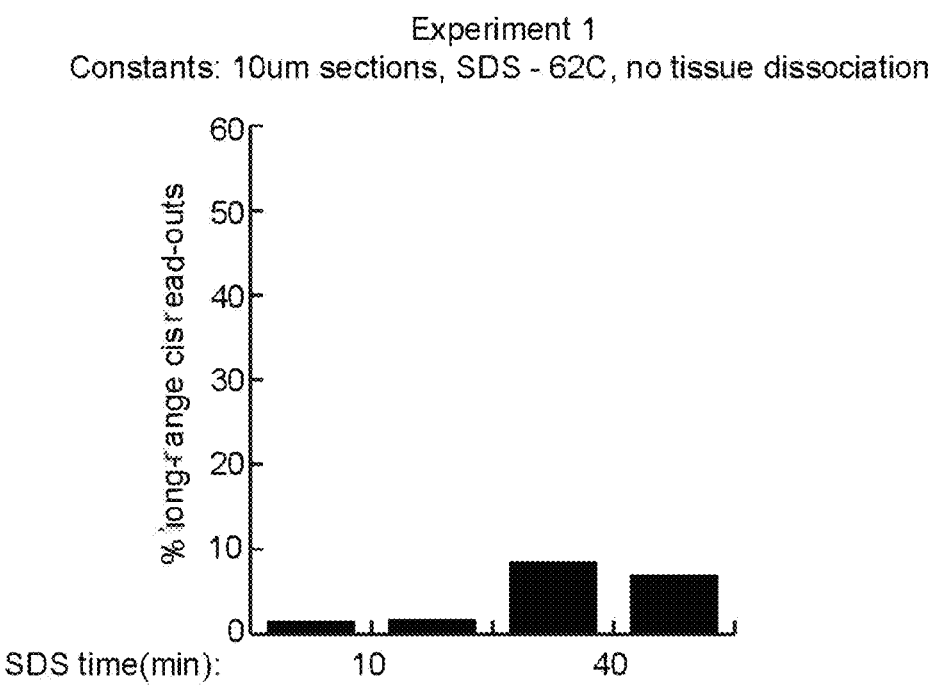
FIGS. 1A-D show the extension of chromatin solubilization and decompaction reaction improves capture of spatial-proximal contiguity signal from formalin-fixed paraffin-embedded (FFPE) samples.

Example 7: Extension of the Chromatin Solubilization and Decompaction Reaction Improves Spatial-Proximal Contiguity Signal from FFPE Samples LPs were prepared from 10 um FFPE sections with a combination of two 4-cutter restriction enzymes, but solubilized and decompacted the chromatin prior to digestion using the published time of 10 minutes of SDS treatment, or extended treatments of 40 minutes, in replicate. Once LPs were generated, the protocol continued with fragmentation, biotin enrichment, and preparation as a template and short-read sequencing. The fraction of sequencing readouts that are long-cis was used as a proxy for the preservation of spatial-proximal contiguity. The published SDS treatment time of 10 min contained only ~1.65% of templates that are long-cis, while 40 minutes of SDS treatment increased this fraction to ~7.75%, nearly a 5-fold increase (see FIG. 1A), yet still below state-of-the-art levels of capturing spatial-proximal contiguity (~40% long-cis readouts). These results indicate that the spatial-proximal contiguity signal can be improved by chromatin solubility and decompaction optimization.

Figure 1B:
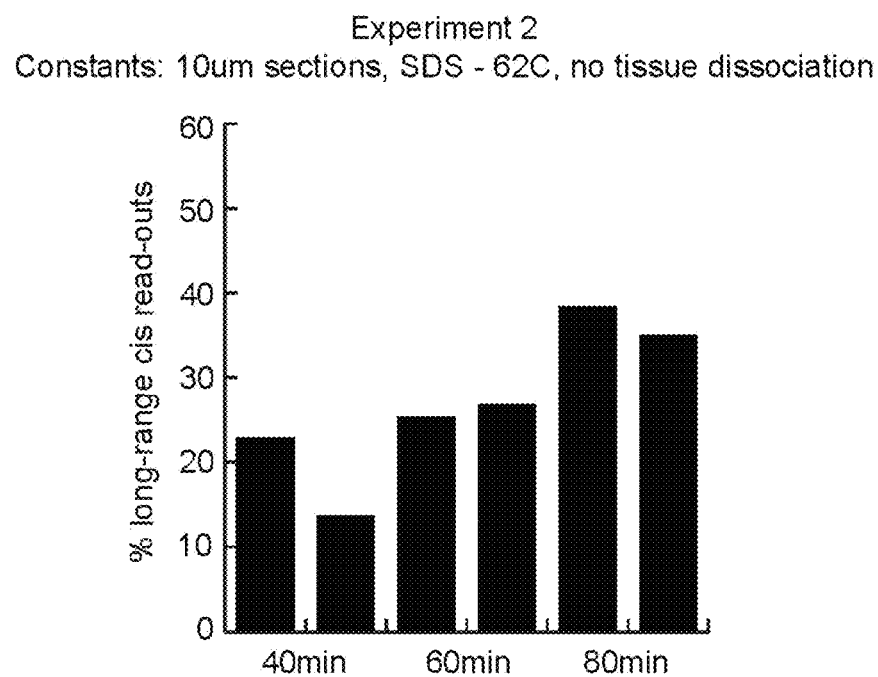
Figure 1C:
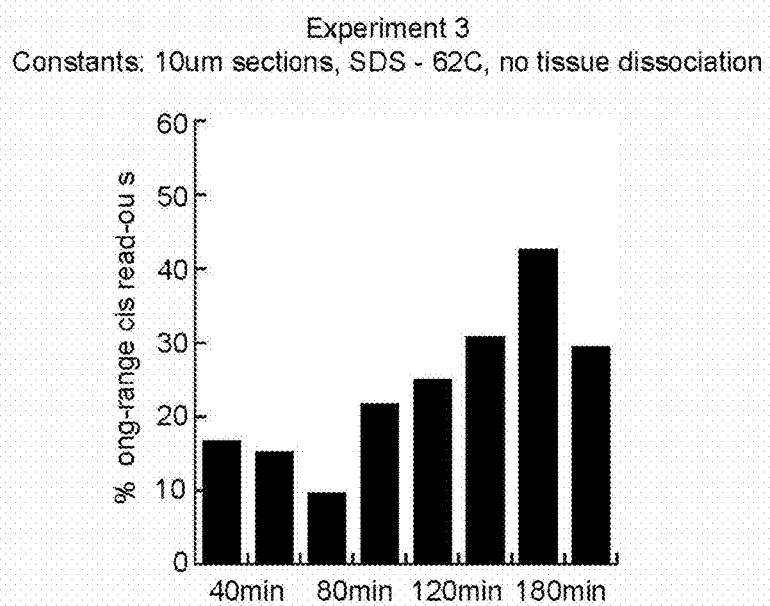

Example 8: Extension of the Chromatin Solubilization and Decompaction Reaction to 80 Min Improves Spatial-Proximal Contiguity Signal from FFPE Samples LPs were prepared from 10 um FFPE sections using a combination of two 4-cutter restriction enzymes, but solubilized and decompacted the chromatin prior to digestion using previously optimized 40 min (See FIG. 1A), or extended treatment durations of 60 or 80 minutes, in replicate. Once LPs were generated, the protocol continued with fragmentation, biotin enrichment, and preparation as a template and short-read sequencing. The fraction of sequencing readouts that are long-cis was used as a proxy for the preservation of spatial-proximal contiguity. The previous extended SDS treatment time of 40 min contained only ~18% of templates that are long-cis, while 60 minutes of SDS treatment increased this fraction to ~25%, and 80 minutes of SDS treatment increased to ~37% long-cis (see FIG. 1B). The long-cis from 80 min SDS duration indicates a >20-fold increase relative to 10 min of SDS (See FIG. 1A), yet still below state-of-the-art levels of capturing spatial-proximal contiguity (~40% long-cis readouts). These results indicate that the spatial-proximal contiguity signal can be improved by chromatin solubility and decompaction optimization.

Example 9: Extension of the Chromatin Solubilization and Decompaction Reaction to 180 Min Improves Spatial-Proximal Contiguity Signal from 10 um FFPE Samples LPs were prepared from 10 um FFPE sections using a combination of two 4-cutter restriction enzymes, but solubilized and decompacted the chromatin prior to digestion using 40 min, or extended treatment durations of 80, 120, or 180 minutes, in replicate. Once LPs were generated, the protocol continued with fragmentation, biotin enrichment, and preparation as a template and short-read sequencing. The fraction of sequencing readouts that are long-cis was used as a proxy for the preservation of spatial-proximal contiguity. The SDS treatment time of 40 min contained only ~16% of templates that are long-cis, while 80, 120, and 180 minutes of SDS treatment increased this fraction to ~16%, 28%, and 37%, on average (see FIG. 10). The long-cis from 180 min SDS duration indicates a >20-fold increase relative to 10 min of SDS (See FIG. 1A), yet still below state-of-the-art levels of capturing spatial-proximal contiguity (~40% long-cis readouts).

Figure 1D:
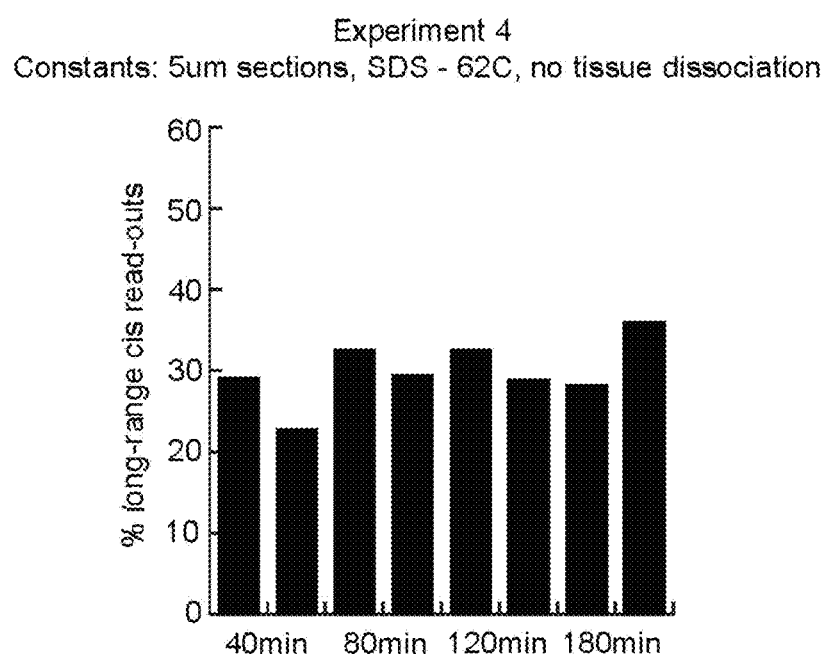

Example 10: Extension of the Chromatin Solubilization and Decompaction Reaction to 180 Min does not Significantly Improve Spatial-Proximal Contiguity Signal from 5 um FFPE Samples LPs were prepared from 5 um FFPE sections using a combination of two 4-cutter restriction enzymes, but solubilized and decompacted the chromatin prior to digestion using 40 min, or extended treatment durations of 80, 120, or 180 minutes, in replicate. Once LPs were generated, the protocol continued with fragmentation, biotin enrichment, and preparation as a template and short-read sequencing. The fraction of sequencing readouts that are long-cis was used as a proxy for the preservation of spatial-proximal contiguity. SDS treatment time of 40 min contained only ~26% of templates that are long-cis, while 80, 120, and 180 minutes of SDS treatment increased this fraction to ~30.5%, 31%, and 32%, on average (see FIG. 1D). While the long-cis is still a significant improvement relative to 10 min of SDS (See FIG. 1D), it still below state-of-the-art levels of capturing spatial-proximal contiguity (~40% long-cis readouts). These results indicate that for 5 um sections, there is no tangible benefit of extending the SDS reaction beyond 80 min, and it appears the SDS duration optimization plateaus below desirable levels of long-cis readouts.

Example 11: Increasing the Temperature of Chromatin Solubilization and Decompaction to Extreme Heat Surprisingly Improves Spatial-Proximal Contiguity Signal from 5 um FFPE Samples To explore the effect of temperature and duration of the chromatin solubilization and decompaction reaction, LPs were prepared from 5 um FFPE sections using a combination of two 4-cutter restriction enzymes, but solubilized and decompacted the chromatin prior to digestion using 10, 40, or 80 minutes at 50° C., 62° C., or 74° C., as indicated. Once LPs were generated, the protocol continued with fragmentation, biotin enrichment, and preparation as a template and short-read sequencing. The fraction of sequencing readouts that are long-cis was used as a proxy for the preservation of spatial-proximal contiguity. 50° C. SDS treatments from 10-80 min resulted in ~2.8-10.2% long-cis templates, while 62° C. SDS treatments from 10-80 min resulted in ~6.8-39% long-cis templates. Surprisingly, 74° C. SDS treatments from 10-40 min resulted in ~31.7-54.2% long-cis templates (see FIG. 2A), a significant improvement over conventional 62° C. treatments reaching superior levels of spatial-proximal contiguity signal. This result is surprising because extremely high heat can begin to denature AT-rich dsDNA and reverse the formalin crosslinks that are critical to hold together the 3D chromatin structure and required for capturing spatial-proximal contiguity via proximity ligation or other methods that entail crosslinking.

Example 12: Increasing the Temperature of Chromatin Solubilization and Decompaction to Extreme Heat Surprisingly Improves Spatial-Proximal Contiguity Signal from 10 um FFPE Samples To determine whether the extreme heat during chromatin solubilization and decompaction reaction improves long-cis in thicker (10 um) FFPE section, we prepared LPs from 10 um FFPE sections using a combination of two 4-cutter restriction enzymes, but solubilized and decompacted the chromatin prior to digestion using 10, 40, or 80 minutes at 74° C., in replicate. Once LPs were generated, the protocol continued with fragmentation, biotin enrichment, and preparation as a template and short-read sequencing. The fraction of sequencing readouts that are long-cis was used as a proxy for the preservation of spatial-proximal contiguity. 74° C. SDS treatments for 10 min resulted in virtually no (~0.5%) long-cis templates, while 40 and 80 min resulted in ~53.5% and 55.5% long-cis templates, on average, respectively (see FIG. 2B). This surprising result also indicates the robustness of the 74° C. for 40 min protocol to 5 and 10 um FFPE samples.

Figure 2A:
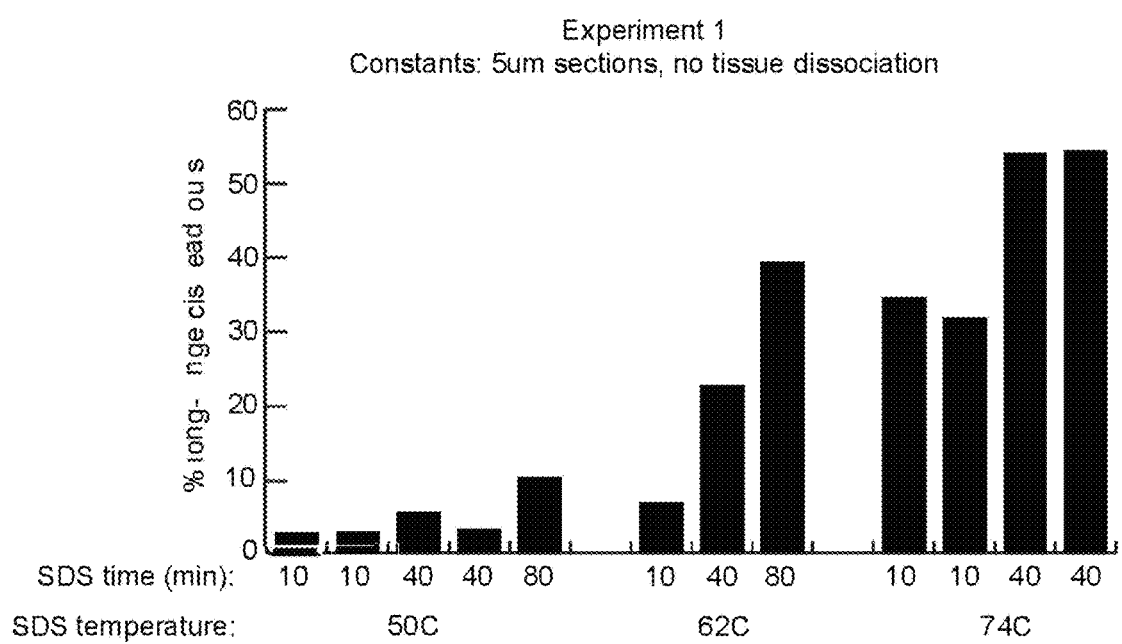
FIGS. 2A and 2B show increasing the temperature of chromatin solubilization and decompaction improves capture of spatial-proximal contiguity signal from formalin-fixed paraffin-embedded (FFPE) samples.
Figure 2B:
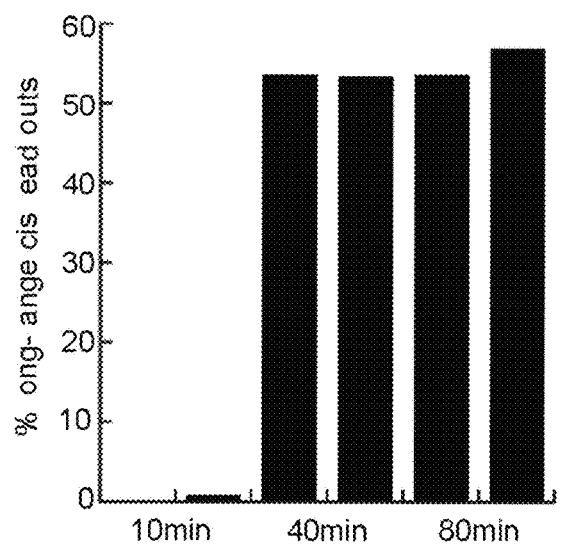
Figure 3:
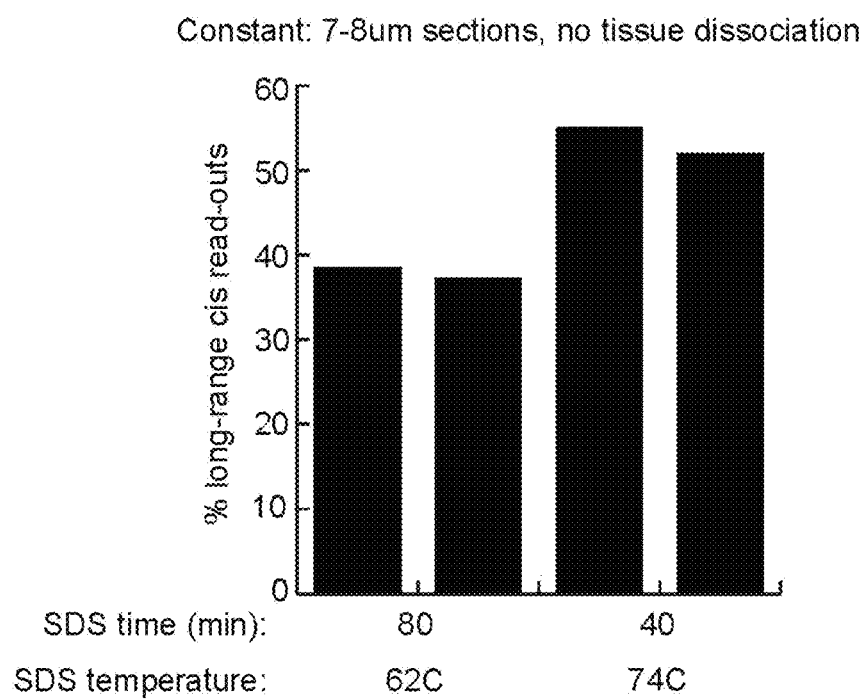
FIG. 3 shows chromatin solubilization and decompaction at 74° C. for 40 minutes optimally captures spatial-proximal contiguity signal in a clinical human FFPE tumor sample.

Example 13: Chromatin Solubilization and Decompaction at 74° C. for 40 Min Optimally Captures Spatial-Proximal Contiguity Signal from a Clinical Human FFPE Tumor Sample To examine whether the extreme heat during chromatin solubilization and decompaction reaction improves long-cis in a patient-derived FFPE tumor sample, LPs were prepared from 7-8 um FFPE sections, including a cellular lysis step and using a combination of two 4-cutter restriction enzymes, but solubilized the chromatin prior to digestion using 40, or 80 minutes at 62° C. or 74° C., in replicate, as indicated. 62° C. for 80 minutes was selected because 80 minutes was the time at which further extension yielded no improvement in long-cis on 5 um sections, whereas 74° C. for 40 min was selected based on the optimal performance and robustness at various section thickness (FIGS. 2A and 2B). Once LPs were generated, the protocol continued with fragmentation, biotin enrichment, and preparation as a template and short-read sequencing. The fraction of sequencing readouts that are long-cis was used as a proxy for the preservation of spatial-proximal contiguity. 62° C. SDS treatment for 80 min resulted in 38% long-cis templates, whereas 74° C. SDS treatments for 40 min resulted in 53.5% long-cis templates (FIG. 3). This surprising result indicates the optimal capture of spatial-proximal contiguity and robustness of the 74° C. for 40 min protocol in patient-derived FFPE tissue.

Figure 4:
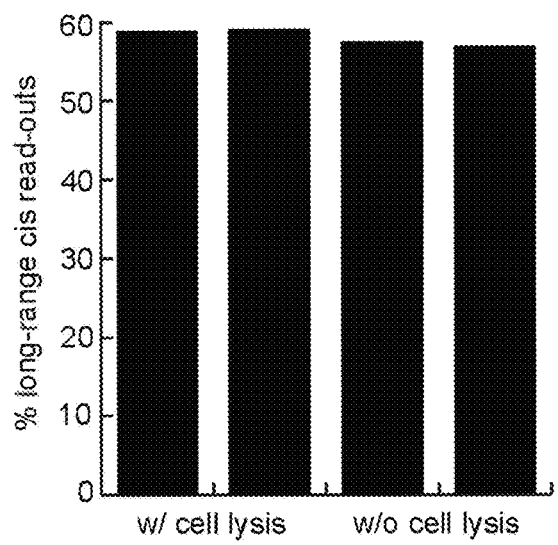
FIG. 4 shows cellular lysis is not required to optimally capture spatial-proximal contiguity signal in FFPE samples.

Example 14: Cellular Lysis is not Required to Capture Optimal Spatial-Proximal Contiguity Signal from FFPE Samples To examine whether the extreme heat during chromatin solubilization and decompaction reaction eliminates the need for cellular lysis for FFPE samples, LPs were prepared from 5 um FFPE sections by either including a cellular lysis step per the optimized protocol described herein (see FIGS. 1 to 3), or, without cellular lysis. A combination of two 4-cutter restriction enzymes was used, but solubilized and decompacted the chromatin prior to digestion using 40 minutes at 74° C., in replicate. Once LPs were generated, the protocol continued with fragmentation, biotin enrichment, and preparation as a template and short-read sequencing. The fraction of sequencing readouts that are long-cis was used as a proxy for the preservation of spatial-proximal contiguity. FFPE samples that underwent cellular lysis resulted in 59% long-cis templates, whereas FFPE samples that had foregone cellular lysis resulted in 57.5% long-cis templates, on average (see FIG. 4). This surprising result indicates the optimal capture of spatial-proximal contiguity and robustness of the 74° C. for 40 min protocol, which also obviates the need for cellular lysis.

Example 15: De-Waxing and Rehydration is Required to Capture Spatial-Proximal Contiguity Signal from FFPE Samples when the SDS Reaction is at 62° C.

Figure 5A:
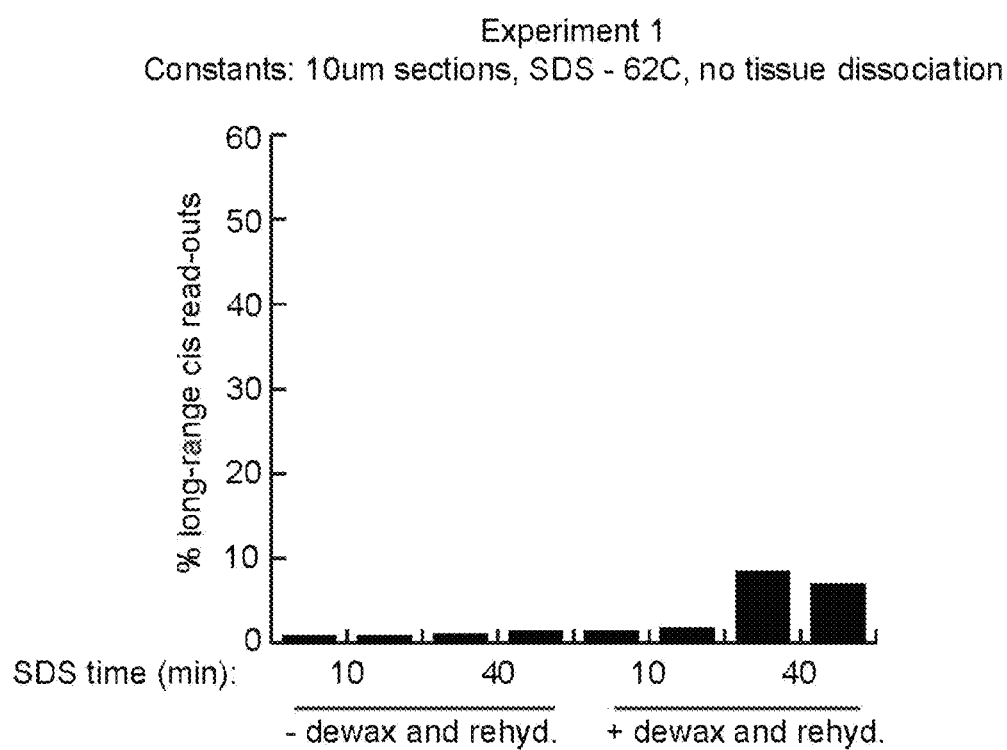
FIGS. 5A and 5B show the effect of time and temperature of the SDS reaction on the need for de-waxing and rehydration to optimally capture spatial-proximal contiguity from FFPE samples.

To examine whether one can capture spatial-proximal contiguity signal from FFPE samples without having to de-wax and rehydrate the tissue, LPs were prepared from 10 um FFPE sections by either including standard de-waxing and rehydration per the optimized protocol described herein (see FIGS. 1-4), or, without subjecting the FFPE samples to de-waxing or rehydration (contrary to the standard procedures used for next-generation sequencing from FFPE samples). A combination of two 4-cutter restriction enzymes was used, but solubilized and decompacted the chromatin prior to digestion using 10 or 40 minutes at 62° C., in replicate. Once LPs were generated, the protocol continued with fragmentation, biotin enrichment, and preparation as a template and short-read sequencing. The fraction of sequencing readouts that are long-cis was used as a proxy for the preservation of spatial-proximal contiguity. FFPE samples that were not dewaxed and rehydrated resulted in 0.8-1.4% long-cis templates, whereas FFPE samples that did receive de-waxing and rehydration resulted in 1.5-8.5% long-cis templates, on average, with a greater fraction of long-cis templates at longer SDS reaction durations (see FIG. 5A). These results indicate that the capture of spatial-proximal contiguity signal is minimal when the FFPE sample forgoes de-waxing and rehydration and a 62° C. chromatin solubilization and decompaction reaction.

Figure 5B:
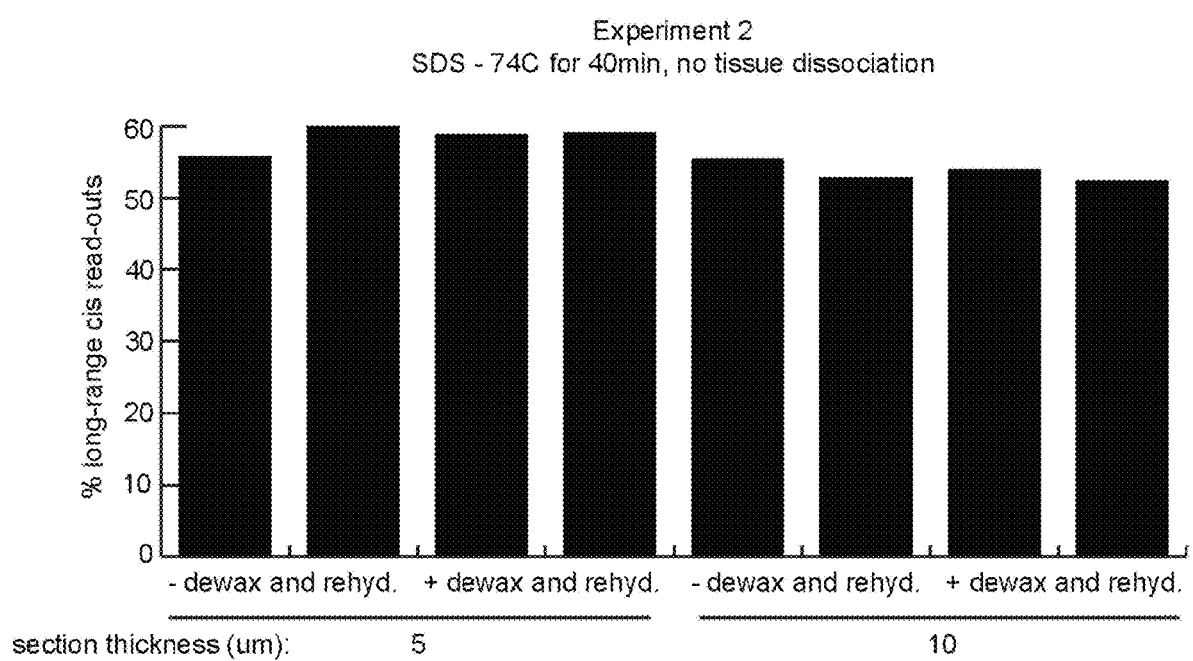

Example 16: De-Waxing and Rehydration is not Required to Capture Optimal Spatial-Proximal Contiguity Signal from FFPE Samples when the SDS Reaction is at 74° C. for 40 Min To examine whether one can capture optimal spatial-proximal contiguity signal from FFPE samples without having to de-wax and rehydrate the tissue, LPs were prepared from 5 and 10 um FFPE sections by either including standard de-waxing and rehydration per the optimized protocol described herein (see FIGS. 1-4), or, without subjecting the FFPE samples to de-waxing or rehydration (contrary to the standard procedure used for next-generation sequencing from FFPE samples). A combination of two 4-cutter restriction enzymes was used, but solubilized and decompacted the chromatin prior to digestion using SDS for 40 minutes at 74° C., in replicate. Once LPs were generated, the protocol continued with fragmentation, biotin enrichment, and preparation as a template and short-read sequencing. The fraction of sequencing readouts that are long-cis was used as a proxy for the preservation of spatial-proximal contiguity. FFPE samples that were not dewaxed and rehydrated resulted in 53-60% long-cis templates, whereas FFPE samples that did receive de-waxing and rehydration resulted in 52.4-59% long-cis templates, on average (see FIG. 5B). These results surprisingly indicate the optimal capture of spatial-proximal contiguity from FFPE samples that forego de-waxing and rehydration and undergo a 74° C. chromatin solubilization and decompaction reaction.

Figure 6:
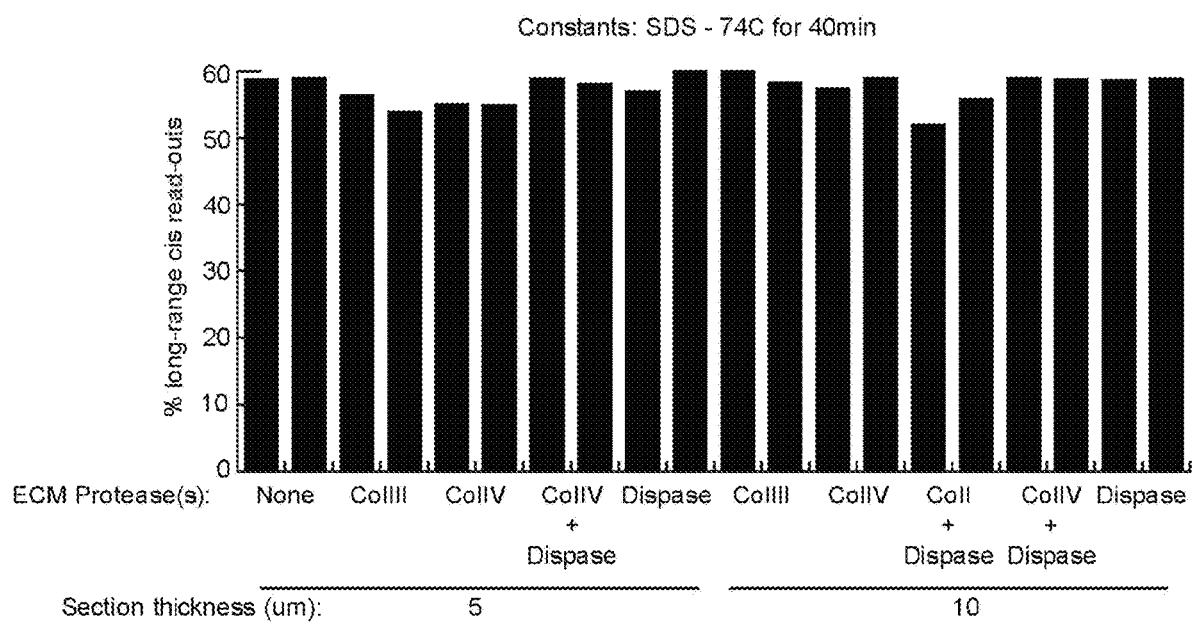
FIG. 6 shows enzymatic dissociation of extracellular matrix proteins improves ease of sample use without compromising optimal capture of spatial-proximal contiguity signal from FFPE samples.

Example 17: Enzymatic Dissociation of Extracellular Matrix Proteins Improves User-Friendliness without Compromising Optimal Capture of Spatial-Proximal Contiguity Signal from FFPE Samples To examine whether one can enzymatically dissociate the FFPE samples to improve user-friendliness (e.g. improve ease of pipetting) without sacrificing the optimal capture of spatial-proximal contiguity, LPs were prepared from 5 and 10 um FFPE sections by either including an enzymatic dissociation step (with Collagenase III, Collagenase IV, Collagenase I, Dispase, or a combination as indicated), or, without enzymatic dissociation per the optimized protocols described herein (see FIGS. 1-5). A combination of two 4-cutter restriction enzymes, but solubilized and decompacted the chromatin prior to digestion using SDS for 40 minutes at 74° C., in replicate. Once LPs were generated, the protocol continued with fragmentation, biotin enrichment, and preparation as a template and short-read sequencing. The fraction of sequencing readouts that are long-cis was used as a proxy for the preservation of spatial-proximal contiguity. All FFPE samples resulted in 50-60% long-cis templates, on average (see FIG. 6). These results indicate the optimal capture of spatial-proximal contiguity from FFPE samples even when the samples are pre-treated with an ECM protease to improve user-friendliness of the workflow.

Figure 18:
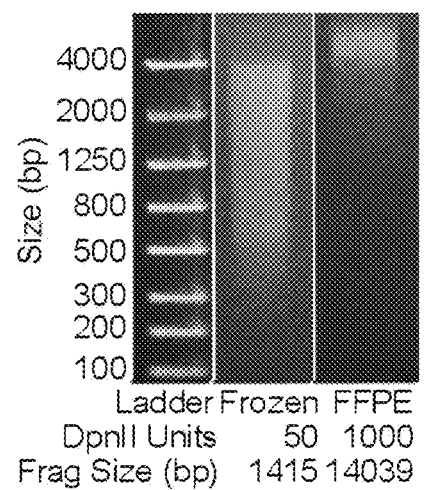
FIG. 18 shows failure of chromatin digestion in FFPE cells.

Example 18: Failure of Chromatin Digestion in FFPE Cells Processed Using Standard Protocol for Crosslinked Cells 10 um FFPE sections were prepared from human cell lines. The sample was dewaxed and rehydrated and then processed using the initial steps of a standard HiC protocol for mammalian cells (treatment with lysis buffer followed by 10 min of solubilization and decompaction at 62° C.) and then digestion using 1000 U of a 4-cutter restriction enzyme (DpnII). An excess of restriction enzyme was used to anticipate the overly fixed chromatin resulting from the FFPE sample. As a control, frozen fixed cells (not FFPE) were subject to standard HiC protocol for mammalian cells, with just 50 U of DpnII. After digestion the crosslinks were reversed and DNA was purified and the size was analyzed by gel electrophoresis and Agilent TapeStation instrument (Agilent Technologies, Inc., Santa Clara, Calif.). The gel electrophoresis analysis indicated efficiently digested chromatin for the frozen cells and virtually no digestion for the FFPE cells, despite having 20-fold more restriction enzyme units (See FIG. 18). The TapeStation analysis of the average fragment size (see "Frag Size (bp)" row) supports the gel analysis and provides more precise quantitation of the average size of the DNA after digestion.

Figure 19:
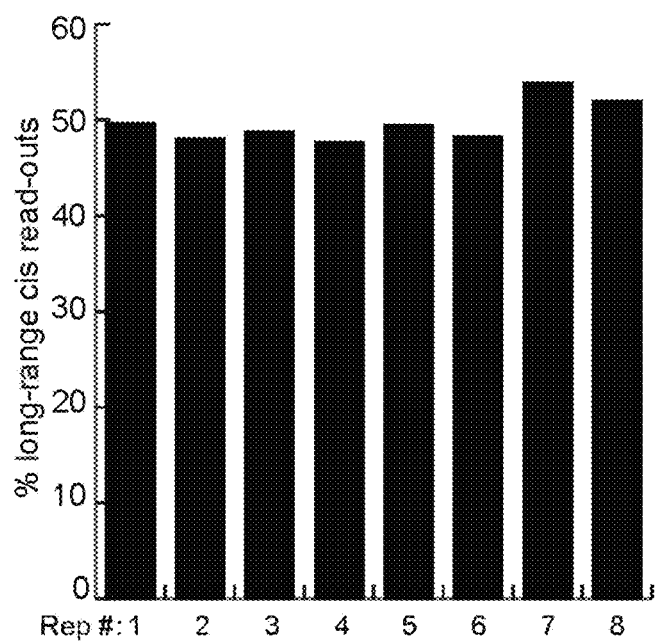
FIG. 19 shows automated HiC on FFPE tissues.

Example 19: Automated HiC on FFPE Tissues 5 um FFPE sections of mouse liver tissue were de-waxed and rehydrated, and then put through a protocol optimized for FFPE samples, as described herein (no tissue dissociation (extracellular matrix protease), treatment with lysis buffer and 40 min of solubilization and decompaction at 74° C.) and subject to HiC using with 2 4-cutter restriction enzymes. However the entire HiC protocol, from lysis through reverse crosslinking and DNA purification was carried out on the Agilent Bravo automated liquid handling platform (Agilent Technologies, Inc., Santa Clara, Calif.). LPs were sheared using the Bioruptor® Pico instrument (Diagenode, Danville, N.J.) and then DNA was returned to the Bravo for automated library prep using KAPA Hyper-Prep (KAPABIOSYSTEMS, Capetown, South Africa). Library amplification was carried out in a PCR machine, and the post-PCR amplicons were returned to the Bravo automated liquid handling platform for purification. Upon shallow sequencing and analysis, consistently high long-range cis readouts from each of the 8 replicates analyzed in the automated experiment was observed (see FIG. 19).

Figure 20:
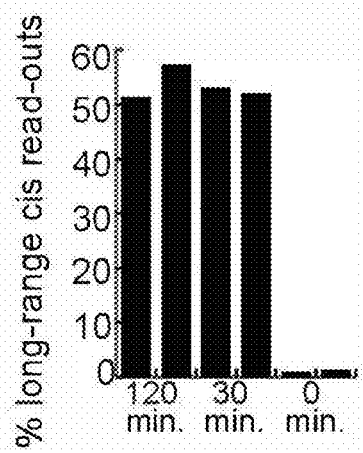
FIG. 20 shows rapid reverse crosslinking in FFPE tissues.

Example 20: Rapid Reverse Crosslinking in FFPE Tissues 5 um FFPE sections were put through a HiC protocol. Mouse liver tissue was de-waxed and rehydrated, and then put through a protocol optimized for FFPE samples, as described herein (no tissue dissociation (extracellular matrix protease), treatment with lysis buffer and 40 min of solubilization and decompaction at 74° C.). The sample was then subject to HiC using 2 4-cutter restriction enzymes. However the reverse crosslinking procedure was varied such that the tissue received the standard treatment (30 min of Proteinase K (ProK) at 55° C. then 90 min at 68C), just the lower temperature treatment (30 min of ProK at 55° C.), or no reverse crosslinking at all as a negative control. Shallow sequencing and analysis indicated high long-range cis readouts from the reduced reverse crosslinking protocol, comparable to the full reverse crosslinking protocol, and significantly better than no reverse crosslinking (see FIG. 20). Also, see Example 17 and FIG. 6, which reversed crosslinking using the 30 min of ProK at 55° C. protocol.

In another set of experiments, the reverse crosslinking procedure was incubation at 95° C. for 60 minutes in the absence of Proteinase K. The amount of DNA that was purified was approximately equivalent to the amount obtained using the full reverse crosslinking protocol. The long cis values were approximately 48-50% long-range cis, comparable to values obtained using the full reverse crosslinking protocol.

Figure 21:
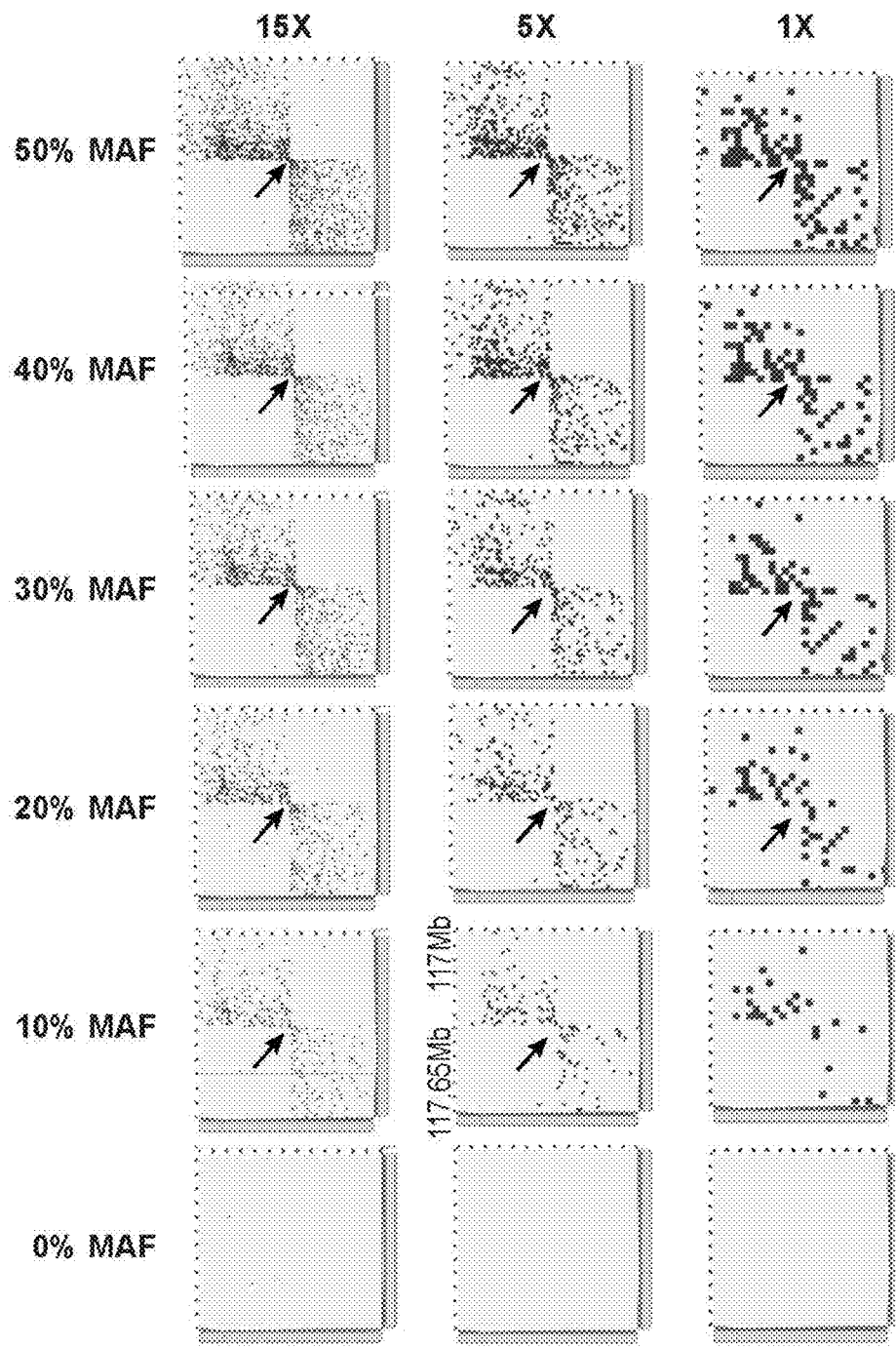
FIG. 21 shows highly sensitive discovery of a known translocation as a function of mutant allele frequency and sequencing depth using genome-wide HiC data from FFPE cells.

Example 21: Highly Sensitive Discovery of a Known Translocation as a Function of Mutant Allele Frequency and Sequencing Depth Using Genome-Wide FFPE-HiC Data FFPE blocks of cells harboring a heterozygous a ROS1-SLC34A2 translocation in every cell (50% mutant allele frequency (MAF)) or a karyotypically normal cell line (GM24385) were obtained from Horizon Discovery (Waterbeach, United Kingdom). 10 um FFPE sections were de-waxed, rehydrated, treated with lysis buffer followed by 40 min of solubilization and decompaction at 62° C. and subject to HiC using digestion with 2 4-cutter restriction enzymes. Following deep sequencing analysis (~30×) on each sample, raw reads were computationally mixed at the following cancer:normal ratios: 100:0; 80:20; 60:40, 40:60, 20:80, and 0:100, thus representing 50%, 40%, 30%, 20%, 10%, and 0% mutant allele frequency of the ROS1:SLC34A2 translocation (rows). This read mixing was also conducted in such a way that the total depth would be fixed at either 15×, 5×, or 1× (columns). The translocation was then identified using HiC-Breakfinder which found the ROS1-SLC34A2 translocation in all depth and MAF combination except the 10% MAF at 1× depth, and all the negative control conditions (0% MAF). Black arrows are overlaid on the HiC contact maps around the ROS1-SLC34A2 genes in cases which HiC-Breakfinder made the translocation call (see FIG. 21).

Figure 22:
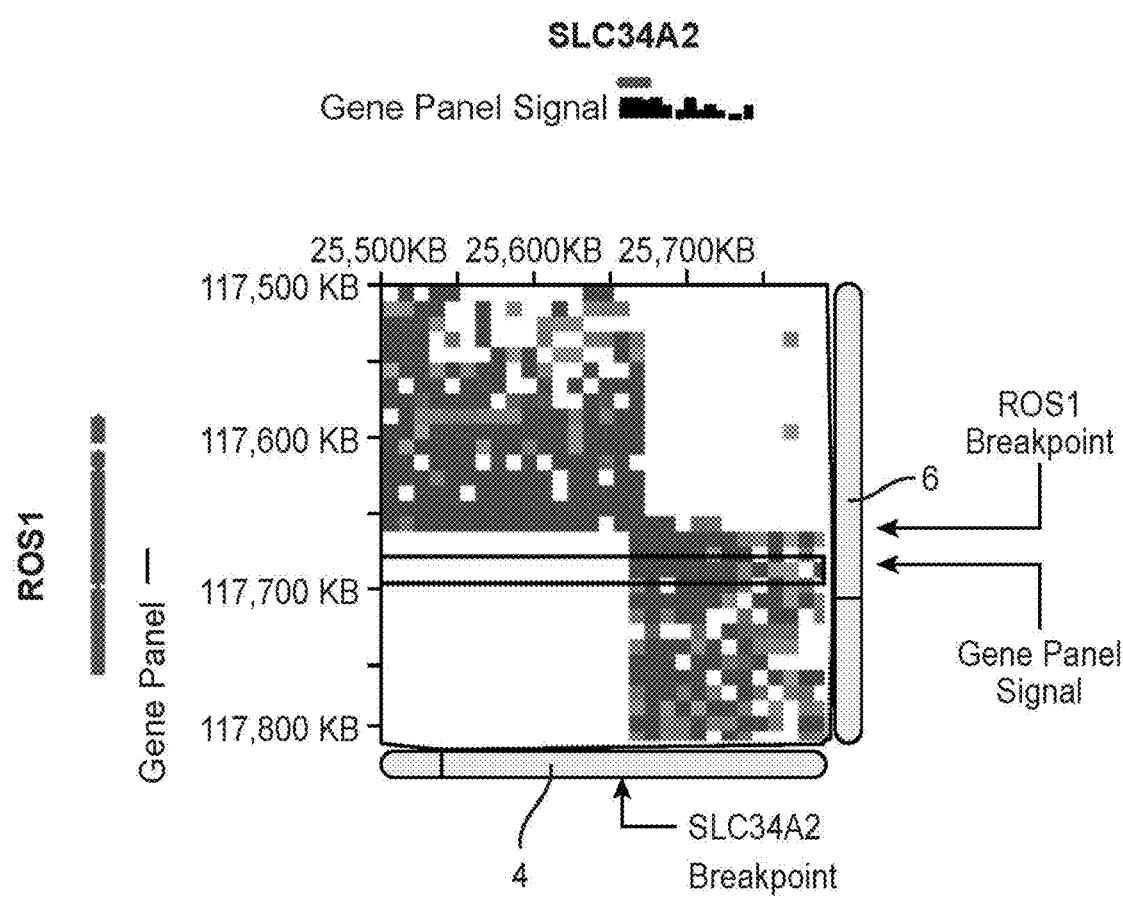
FIG. 22 shows highly sensitive discovery of a known translocation enabled by targeted HiC data from FFPE cells.

Example 22: Highly Sensitive Discovery of a Known Translocation Enabled by Targeted FFPE-HiC Data 10 um FFPE sections of cells harboring a heterozygous a ROS1-SLC34A2 translocation in every cell (50% mutant allele frequency (MAF)) were de-waxed, rehydrated, treated with lysis buffer followed by 40 min of solubilization and decompaction at 62° C. and subject to HiC using digestion with 2 4-cutter restriction enzymes. Following deep sequencing analysis (~30×) on each sample, the effect of targeted HiC ("Capture-HiC") was simulated by capturing all the HiC signal derived from one locus in the genome ~50 kb downstream from the true ROS1-SLC34A2 breakpoint. The HiC signal produced at only 30× depth (which is significantly less than typically oncology gene panel sequencing) was plotted across the top. Virtually zero HiC signal was observed upstream of the breakpoint on SLC34A2. The HiC signal was observed to peak at the breakpoint in SLC34A2 and then decrease for loci moving downstream from SLC34A2 (see FIG. 22). The location of the breakpoint is in SLC34A2, is based on the peak HiC signal (and underlying sequence information) and distance dependent decay signal moving away from (in this case downstream) from the breakpoint.

Example 23: Discovery and Validation of Translocations in an FFPE GIST Tumor

A 7-8 um FFPE section of a gastrointestinal stromal tumor (GIST) was de-waxed and rehydrated, and then put through a protocol optimized for FFPE samples, as described herein (no tissue dissociation (extracellular matrix protease), treatment with lysis buffer and 40 min of solubilization and decompaction at 74° C.). The sample was then subject to HiC using 2 4-cutter restriction enzymes. Shallow sequencing analysis indicated high long-range cis readouts (see FIG. 23A). Furthermore, genome-wide shallow sequencing analysis (0.75× sequencing; ~$30 costs) identified 19 translocations, with several breakpoints implicating genes associated with cancer but not commonly targeted by gene panels. For example, the analysis discovered a POLA2-PIGU translocation. POLA2 has at least 10 reported partners in cancer databases (i.e. COSMIC, Quiver, TCGA), and is recurrently translocated in GIST. PIGU has >13 reported partners, but neither POLA2 nor PIGU are targeted by tumor genetic profiling panels (such as Agilent ClearSeq (Agilent Technologies, Inc., Santa Clara, Calif.), underscoring the power of HiC to discover promiscuous and partner-agnostic translocations. To obtain sub-Kb breakpoint resolution for PCR validation, sequencing was performed up to ~10× (see FIG. 23B). One inter-chr translocation involving UQCC1 (>12 reported partners) and ARHGAP20 (1 reported translocation in B-CLL) were selected for PCR validation. Test primer pairs (and control primer pairs, not shown) were designed to amplify across the translocation breakpoint (see FIG. 23C). PCR results confirmed a single PCR amplicon (see FIG. 23D), validating the optimized FFPE-HiC protocol and translocation discovery analyses in FFPE tumor tissue.

Example 24: Discovery of Translocations in an FFPE Pediatric Ependymoma Tumor

Figure 24A:
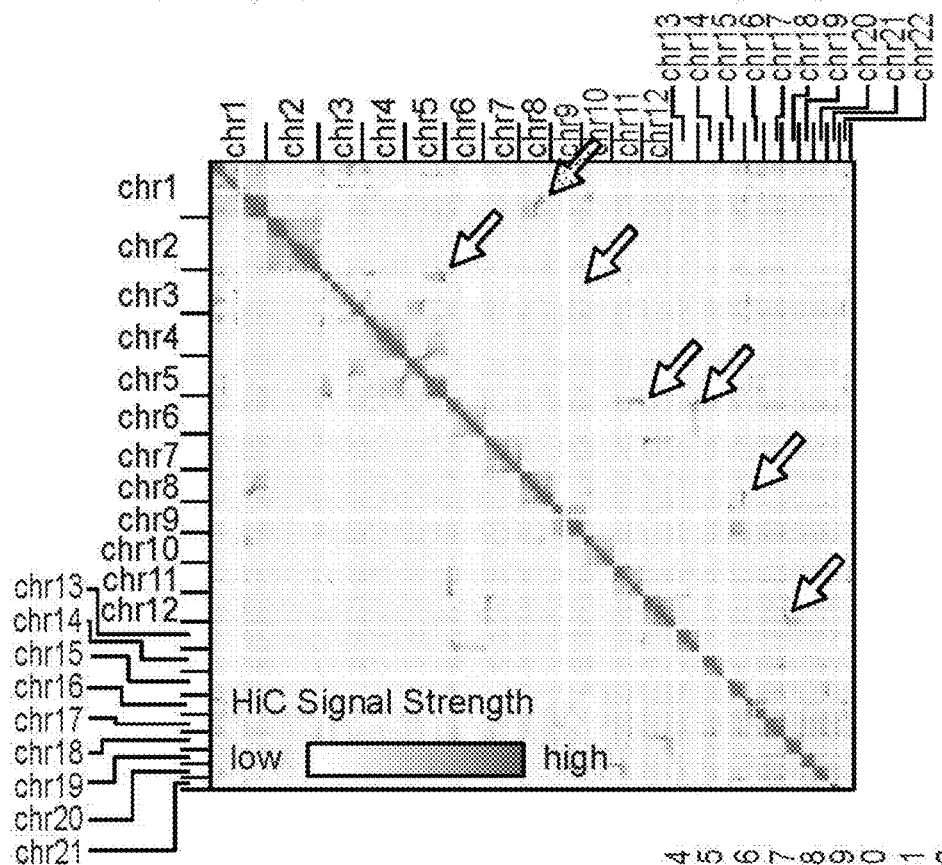
FIGS. 24A-C show discovery of translocations in an FFPE pediatric ependymoma tumor.
Figure 24B:
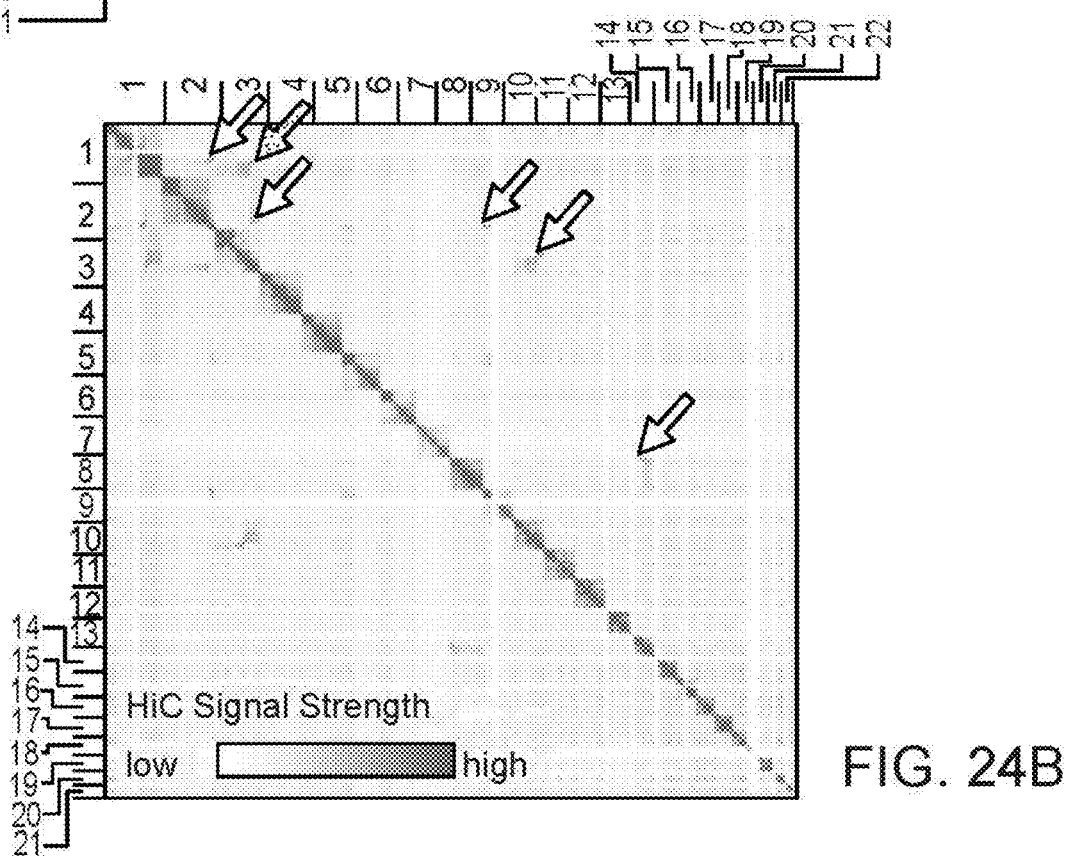
Figure 24C:
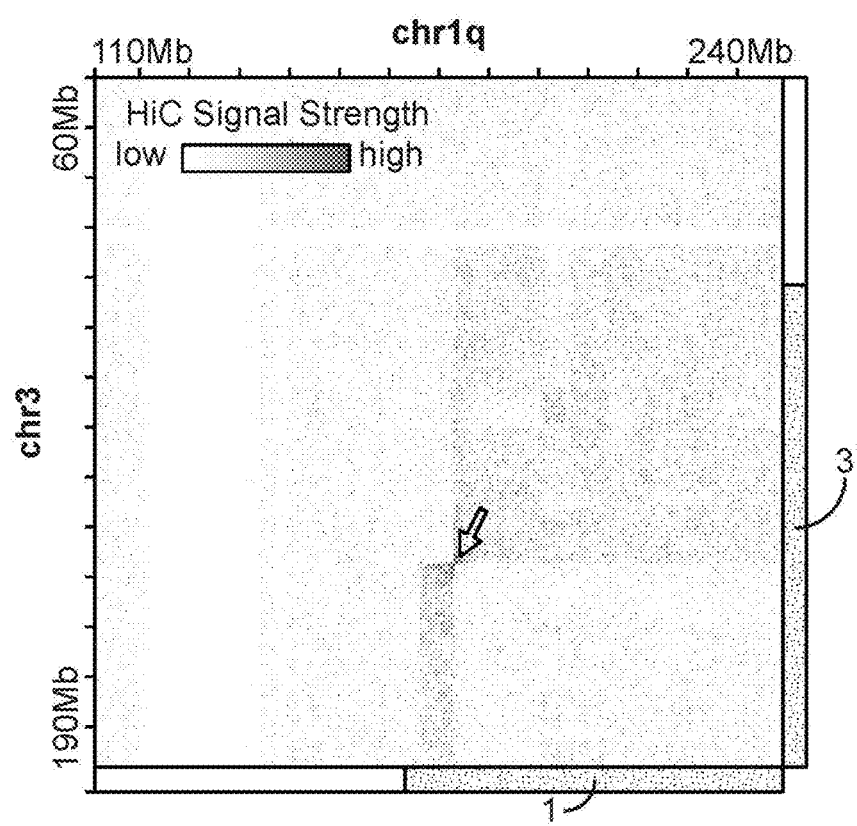
Figure 25A:
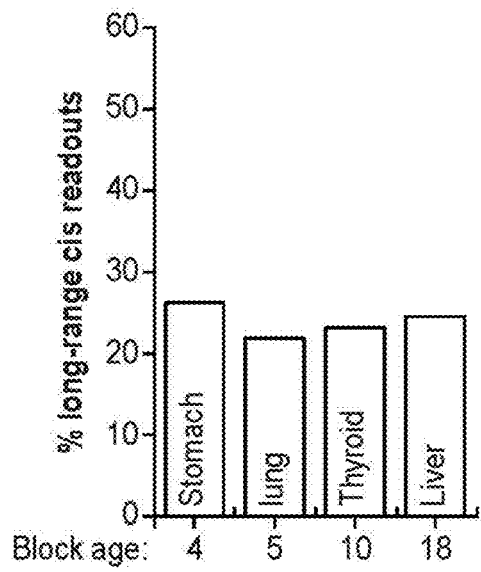
FIGS. 25A-D show discovery of translocations in FFPE tumors across archival periods.
Figure 25B:
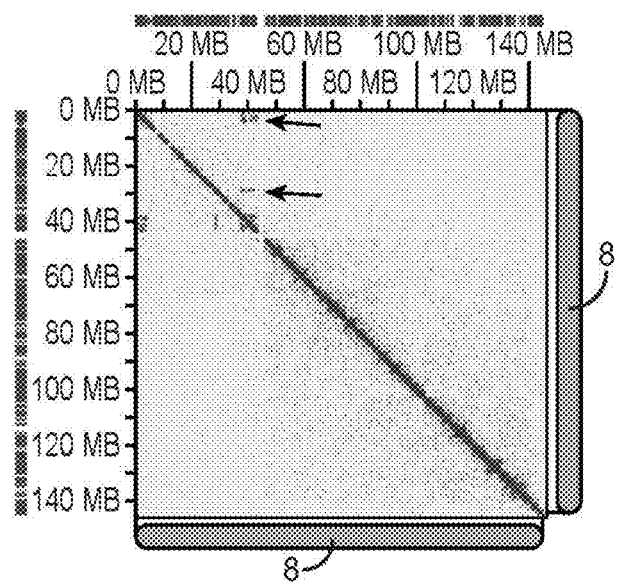
Figure 25C:
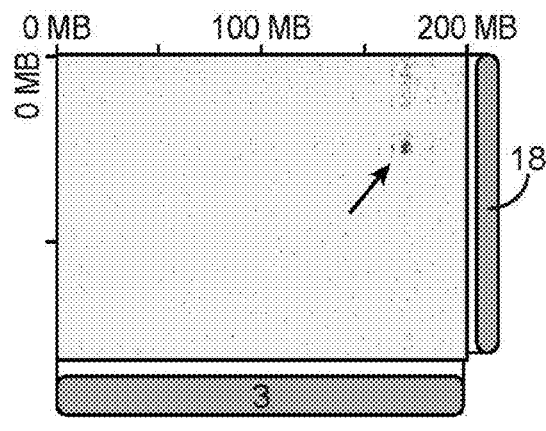
Figure 25D:
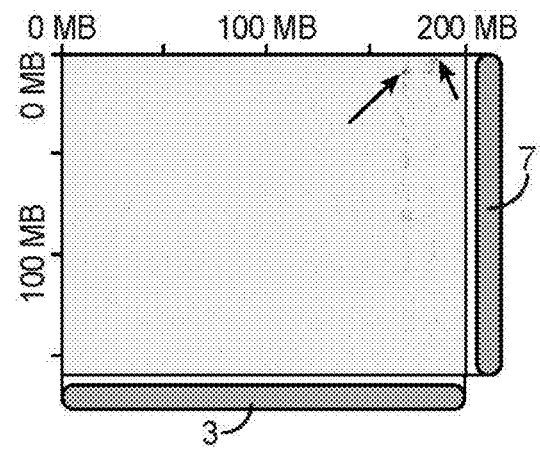

A 5 um FFPE section of a posterior fossa ependymoma (PFE) tumor was de-waxed and rehydrated, and then put through a protocol optimized for FFPE samples, as described herein (no tissue dissociation (extracellular matrix protease), treatment with lysis buffer and 40 min of solubilization and decompaction at 74° C.). The sample was then subject to HiC using 2 4-cutter restriction enzymes. Genome-wide shallow sequencing analysis (0.25× sequencing; ~$10 costs) revealed the presence of several translocations (see FIG. 24B), similar to what has been previously observed in HiC data from PFE cell lines (see FIG. 24A; personal communication with Dr. Lukas Chavez, UCSD). In fact, FFPE-HiC analyses of this PFE tumor identified a chr1;chr3 translocation (see FIG. 24C), whereby the chr1 partner was the same gene involved in a chr1;chr8 translocation previously identified from a PFE cell line derived from a different individual, indicating the potential for FFPE-HiC to identify previously underappreciated, partner-agnostic, and recurring translocations in tumor tissues. Also of note, this FFPE PFE tumor had previously been analyzed using conventional WGS and RNA-seq, but no somatic mutations or translocations were found, thus underscoring the analytical sensitivity of FFPE-HiC compared to state-of-the-art genome-wide (WGS) and targeted (RNA-seq) methodologies for translocation analyses.

Example 25: Discovery of Translocations in FFPE Tumors Across Archival Periods 5 um sections from FFPE blocks containing tumor tissue from either stomach, lung, thyroid, or liver were obtained from BioChain Institute Inc. (Newark, N.J.). Each tumor block had an archival period of 4, 5, 10, or 18 years, respectively (see FIG. 25A). FFPE sections were de-waxed and rehydrated, and then put through a protocol optimized for FFPE samples, as described herein (no tissue dissociation (extracellular matrix protease), treatment with lysis buffer and 40 min of solubilization and decompaction at 74° C.). The processed sections were then subject to HiC using 2 4-cutter restriction enzymes Shallow sequencing analysis indicated moderately high, yet consistent long-range cis readouts across the range of archival periods, even out to 18 years (see FIG. 25A) without negative impact on the quality of the long-range information in the data. From this extremely low sequencing depth (0.05× sequencing; ~$2 costs) in the lung tumor, evidence of 7 translocations were identified, including intra-chr translocations (see FIG. 25B), inter-chromosomal translocation between chr3;chr18 (see FIG. 25C) and chr3;chr7 (see FIG. 25D).

Example 26: High Quality FFPE-HiC from Low Input FFPE Tissue 5-10 um FFPE sections were obtained from mouse liver tissue or human GIST, PFE, lung, liver, stomach, and thyroid tumors. Each tumor section was de-waxed and rehydrated, and then put through a protocol optimized for FFPE samples, as described herein (no tissue dissociation (extracellular matrix protease), treatment with lysis buffer and 40 min of solubilization and decompaction at 74° C.). The processed sections were then subject to HiC using 2 4-cutter restriction enzymes Shallow sequencing analysis indicated moderate to high long-range cis readouts, even in cases where the total amount of DNA extraction from the FFPE tissue section was considered low input, defined here as <200 ng.

Example 27: Non-Limiting Examples of Embodiments

Listed hereafter are non-limiting examples of certain embodiments of the technology.
A1. A method for preparing nucleic acids from a formalin-fixed paraffin-embedded (FFPE) sample, that preserves spatial-proximal contiguity information, comprising:
  a) providing a formalin-fixed paraffin-embedded sample;
  b) de-waxing the sample to produce a de-waxed sample;
  c) rehydrating the de-waxed sample, thereby generating a de-waxed/rehydrated sample;
  d) contacting the de-waxed/rehydrated sample with lysis buffer; thereby generating a lysed sample;
  e) contacting the lysed sample; with a denaturing detergent at a temperature greater than 65° C., thereby generating a solubilized and decompacted sample; and
  f) contacting the solubilized and decompacted sample with one or more reagents that preserve spatial-proximal contiguity information in the nucleic acids of the solubilized and decompacted sample.
A1.1. The method of embodiment A1, wherein the formalin-fixed paraffin-embedded (FFPE) sample is a tissue sample.
A1.2. The method of embodiment A1 or A1.1, wherein the de-waxed/rehydrated sample is contacted with an extracellular matrix protease prior to contact with lysis buffer.
A1.3. The method of embodiment A1.2, wherein the protease is a collagenase and/or a dispase.
A1.4. The method of embodiment A1.3, wherein the collagenase is ColI, ColIII or ColIV, and the dispase is Dispase I.
A2. The method of any one of embodiments A1 to A1.4, wherein contact with the denaturing detergent is for greater than 10 minutes.
A3. The method of embodiment A2, wherein contact with the denaturing detergent is 15 to 80 minutes.
A3.1. The method of embodiment A3, wherein contact with the denaturing detergent is 30 to 50 minutes
A4. The method of embodiment A3.1, wherein contact with the denaturing detergent about 40 minutes.
A4.1 The method of embodiment A4, wherein contact with the denaturing detergent is 40 minutes.
A5. The method of any one of embodiments A1-A4.1, wherein the temperature is greater than 65° C. and less than 80° C.
A6. The method of embodiment A5, wherein the temperature is between 70° C. and 80° C.
A7. The method of embodiment A6, wherein the temperature is about 74° C.
A7.1 The method of embodiment A7, wherein the temperature is 74° C.
A7.2. The method of any one of embodiments A1-A1.4, wherein contact with a denaturing detergent is for 40 minutes at a temperature of 74° C.
A8. The method of any one of embodiments A1-A7.2, wherein the detergent is sodium dodecyl sulfate (SDS).
A9. The method of any one of embodiments A1-A8, wherein one or more reagents that preserve spatial-proximal contiguity information comprise reagents that generate proximity ligated nucleic acid molecules.
A9.1. The method of embodiment A9, wherein the reagents that generate proximity ligated nucleic acid molecules comprise one or more of the following reagents: at least one restriction endonuclease, a DNA polymerase, a plurality of nucleotides comprising at least one biotinylated nucleotide, and a ligase.
A9.2. The method of embodiment A9.1, comprising two restriction endonucleases.
A10. The method of any one of embodiments A9 to A9.2, wherein the proximity ligated nucleic acid molecules are generated in situ.
A11. The method of any one of embodiments A1-A8, wherein one or more reagents that preserve spatial-proximal contiguity information comprise solid phase elements that form complexes with the spatially proximal nucleic acid of the solubilized and decompacted sample to generate spatially proximal nucleic acid of the solubilized and decompacted sample complexed to solid phase elements.

A12. The method of embodiment A11, wherein the solid phase elements are solid phase substrates functionalized with a nucleic acid crosslinking agent.

A13. The method of embodiment A11, wherein the solid phase elements are solid phase substrates functionalized with an affinity purification molecule and the nucleic acid molecules are labeled with an affinity purification marker.

A13.1. The method of any one of embodiments A11 to A13, wherein the spatially proximal nucleic acid of the solubilized and decompacted sample complexed to solid phase elements is contacted with one or more reagents for compartmentalization and tagging with a molecular barcode.

A13.2. The method of embodiment A13.1, wherein the one or more reagents for compartmentalization comprise a microfluidic compartmentalization device that produces microfluidic droplets or microtiter plate wells into which complexes are diluted.

A13.3. The method of embodiment A13.1 or A13.2, wherein tagging with a molecular barcode is by primer extension polymerization (PEP) or by ligation.

A14. The method of embodiment A11, wherein the solid phase elements are solid phase substrates functionalized with a transposase comprising a barcoded oligonucleotide that generate spatially-proximal nucleic acid comprising a barcoded oligonucleotide and complexed to the solid phase substrate functionalized with a transposase A14.1. The method of embodiment A14, wherein the transposase is Tn5.

A15. The method of any one of embodiments A1 to A14.1, wherein the formalin-fixed paraffin-embedded sample is provided on a solid surface.

A15.1. The method of embodiment A15.1, wherein the solid surface is a pathology slide.

A16. The method of any one of embodiments A1 to A8, wherein one or more reagents that preserve spatial-proximal contiguity information comprise reagents that compartmentalize and tag by attaching compartment-specific molecular barcodes to the nucleic acids of the solubilized and decompacted sample.

A16.1. The method of embodiment A16, wherein the one or more reagents that compartmentalize comprise a microfluidic compartmentalization device that produces microfluidic droplets or microtiter plate wells into which complexes are diluted.

A16.2. The method of embodiment A16 or A16.1, wherein the one or more reagents that tag by attaching compartment-specific molecular barcodes comprise reagents for primer extension polymerization (PEP), reagents for ligation or a transposase comprising a barcoded oligonucleotide.

A17. The method of any one of embodiments A1 to A16.2, wherein the formalin-fixed paraffin-embedded sample is provided as a tissue section of about 5 um to about 10 um in thickness.

A18. The method of any one of embodiments, A1 to A8, wherein one or more reagents that preserve spatial-proximal contiguity information comprise a Tn5 tetramer.

A19. The method of any one of embodiments, A1 to A18, wherein step (f) generates nucleic acids with preserved spatial-proximal contiguity information and the nucleic acids with preserved spatial-proximal contiguity information are subjected to bisulfite treatment to generate bisulfite treated nucleic acids with preserved spatial-proximal contiguity information.

A20. The method of embodiment A19, wherein the bisulfite treated nucleic acids with preserved spatial-proximal contiguity information are sequenced to determine the methylation status of the nucleic acids with preserved spatial-proximal contiguity information.

A21. The method of any one of embodiments A1 to A18, wherein step (f) generates nucleic acids with preserved spatial-proximal contiguity information and the nucleic acids with preserved spatial-proximal contiguity information are sequenced to produce sequence readouts.

A22. The method of embodiment A21, wherein the sequencing is at a depth of 30× or less.

A23. The method of embodiment A21 or A22, wherein the sequence readouts have a % of long-range cis readouts greater than the % of long-range cis readouts produced without contact with a denaturing detergent at a temperature greater than 65° C.

A24. The method of embodiment A23, wherein % of long-range cis readouts is greater than 40% of the readouts.

A25. The method of any one of embodiments A1 to A18, wherein the formalin-fixed paraffin-embedded (FFPE) sample has an archival period of about 4 years to about 20 years.

A26. The method of any one of embodiments A1 to A18, wherein the formalin-fixed paraffin-embedded (FFPE) sample has an archival period of about 20 years to about 70 years.

A27. The method of embodiment A25 or A26, wherein step (f) generates nucleic acids with preserved spatial-proximal contiguity information and the nucleic acids with preserved spatial-proximal contiguity information are sequenced to produce sequence readouts.

A28. The method of embodiment A27, wherein the sequencing at a depth of 30× or less.

A29. The method of embodiment A27 or A28, wherein the sequence readouts have a % of long-range cis readouts greater than the % of long-range cis readouts produced without contact with a denaturing detergent at a temperature greater than 65° C.

A30. The method of any one of embodiments A1 to A18, wherein the nucleic acid obtained from the formalin-fixed paraffin-embedded (FFPE) sample is less than 200 ng.

A31. The method of embodiment A30, wherein step (f) generates nucleic acids with preserved spatial-proximal contiguity information and the nucleic acids with preserved spatial-proximal contiguity information are sequenced to produce sequence readouts.

A32. The method of embodiment A31, wherein the sequencing at a depth of 30× or less.

A33. The method of embodiment A31 or A32, wherein the sequence read-outs have a % of long-range cis readouts greater than the % of long-range cis readouts produced without contact with a denaturing detergent at a temperature greater than 65° C.

A34. The method of embodiment A33, wherein % of long-range cis readouts is greater than 40% of the readouts.

A35. The method of any one of embodiments A1 to A34, wherein the method is essentially carried out using automated equipment.

A36. The method of any one of embodiments A1 to A35, wherein after step (f) crosslinking is reversed by contacting the sample with proteinase K at a temperature of less than 68° C. for about 30 minutes.

A37. The method of embodiment A36, wherein the temperature is about 55° C.

A37.1. The method of embodiment A37, wherein the temperature is 55° C.

A38. The method of any one of embodiments A1 to A35, wherein after step (f) crosslinking is reversed by incubating the sample at a temperature of about 95° C. for about 1 hour in the absence of proteinase K.

A38.1. The method of embodiment A38, wherein after step (f) crosslinking is reversed by incubating the sample at a temperature of 95° C. for 1 hour in the absence of proteinase K.

B1. A method for preparing nucleic acids from a formalin-fixed paraffin-embedded (FFPE) sample, that preserves spatial-proximal contiguity information, comprising:
   a) providing a formalin-fixed paraffin-embedded sample;
   b) de-waxing the sample to produce a de-waxed sample;
   c) rehydrating the de-waxed sample, thereby generating a de-waxed/rehydrated sample;
   d) contacting the de-waxed/rehydrated sample with a denaturing detergent at a temperature greater than 65° C., thereby generating a solubilized and decompacted sample; and
   e) contacting the solubilized and decompacted sample with one or more reagents that preserve spatial-proximal contiguity information in the nucleic acids of the solubilized and decompacted sample.

B1.1. The method of embodiment B1, wherein the formalin-fixed paraffin-embedded (FFPE) sample is a tissue sample.

B1.2. The method of embodiment B1 or B1.1, wherein the dewaxed/rehydrated sample is contacted with an extracellular matrix protease prior to contact with a denaturing detergent.

B1.3. The method of embodiment B1.2, wherein the protease is a collagenase and/or a dispase.

B1.4. The method of embodiment B1.3, wherein the collagenase is ColI, ColIII or ColIV and the dispase is Dispase I.

B2. The method of any one of embodiments B1 to B1.4, wherein contact with the denaturing detergent is for greater than 10 minutes.

B3. The method of embodiment B2, wherein contact with the denaturing detergent is 15 to 80 minutes.

B4. The method of embodiment B3, wherein contact with the denaturing detergent is 30 to 50 minutes.

B4.1. The method of embodiment B4, wherein contact with the denaturing detergent is about 40 minutes.

B4.2. The method of embodiment B4.1, wherein contact with the denaturing detergent is 40 minutes.

B5. The method of any one of embodiments B1-B4.2, wherein the temperature is greater than 65° C. and less than 80° C.

B6. The method of embodiment B5, wherein the temperature is between 70° C. and 80° C.

B7. The method of embodiment B6, wherein the temperature is about 74° C.

B7.1 The method of embodiment B7, wherein the temperature is 74° C.

B7.2. The method of any one of embodiments B1-B1.4, wherein contact with a denaturing detergent is for 40 minutes at a temperature of 74° C.

B8. The method of any one of embodiments B1-B7.2, wherein the detergent is sodium dodecyl sulfate (SDS).

B9. The method of any one of embodiments B1-B8, wherein one or more reagents that preserve spatial-proximal contiguity information comprise reagents that generate proximity ligated nucleic acid molecules.

B9.1. The method of embodiment B9, wherein the reagents that generate proximity ligated nucleic acid molecules comprise one or more of the following reagents: at least one restriction endonuclease, a DNA polymerase, a plurality of nucleotides comprising at least one biotinylated nucleotide, and a ligase.

B9.2. The method of embodiment B9.1, comprising two restriction endonucleases.

B10. The method of any one of embodiments B9 to B9.2, wherein the proximity ligated nucleic acid molecules are generated in situ.

B11. The method of any one of embodiments B1-B8, wherein one or more reagents that preserve spatial-proximal contiguity information comprise solid phase elements that form complexes with the spatially-proximal nucleic acids of the solubilized and decompacted sample to generate spatially-proximal nucleic acid of the solubilized and decompacted sample complexed to solid phase elements.

B12. The method of embodiment B11, wherein the solid phase elements are solid phase substrates functionalized with a nucleic acid crosslinking agent.

B13. The method of embodiment B11, wherein the solid phase elements are solid phase substrates functionalized with an affinity purification molecule and the nucleic acid molecules are labeled with an affinity purification marker.

B13.1. The method of any one of embodiments B11 to B13, wherein the spatially proximal nucleic acid of the solubilized and decompacted sample complexed to solid phase elements is contacted with one or more reagents for compartmentalization and tagging with a molecular barcode.

B13.2. The method of embodiment B13.1, wherein the one or more reagents for compartmentalization comprise a microfluidic compartmentalization device that produces microfluidic droplets or microtiter plate wells into which complexes are diluted.

B13.3. The method of embodiment B13.1 or B13.2, wherein tagging with a molecular barcode is by primer extension polymerization (PEP) or by ligation.

B14. The method of embodiment B11, wherein the solid phase elements are solid phase substrates functionalized with a transposase comprising a barcoded oligonucleotide that generate spatially-proximal nucleic acid comprising a ligated barcoded oligonucleotide and complexed to the solid phase substrate functionalized with a transposase.

B14.1. The method of embodiment B14, wherein the transposase is Tn5.

B15. The method of any one of embodiments B1 to B14.1, wherein the formalin-fixed paraffin-embedded sample is provided on a solid surface.

B15.1. The method of embodiment B15, wherein the solid surface is a pathology slide.

B16. The method of any one of embodiments B1 to B8, wherein one or more reagents that preserve spatial-proximal contiguity information comprise reagents that compartmentalize and attach compartment-specific molecular barcodes to the nucleic acids of the solubilized and decompacted sample.

B16.1. The method of embodiment B16, wherein the one or more reagents that compartmentalize comprise a microfluidic compartmentalization device that produces microfluidic droplets or microtiter plate wells into which complexes are diluted.

B16.2. The method of embodiment B16 or B16.1, wherein the one or more reagents that tag by attaching compartment-specific molecular barcodes comprise reagents for primer extension polymerization (PEP), reagents for ligation or a transposase comprising a barcoded oligonucleotide.

B17. The method of any one of embodiments B1 to B16.2, wherein the formalin-fixed paraffin-embedded sample is provided as a tissue section of about 5 um to about 10 um in thickness.

B18. The method of embodiments B17, wherein the formalin-fixed paraffin-embedded sample is provided as a tissue section of about 5 um in thickness.

B19. The method of any one of embodiments, B1 to B8, wherein the one or more reagents that preserve spatial-proximal contiguity information comprise a Tn5 tetramer.

B20. The method of any one of embodiments, B1 to B19, wherein step (e) generates nucleic acids with preserved spatial-proximal contiguity information and the nucleic acids with preserved spatial-proximal contiguity information are subjected to bisulfite treatment to generate bisulfite treated nucleic acids with preserved spatial-proximal contiguity information.

B21. The method of embodiment B20, wherein the bisulfite treated nucleic acids with preserved spatial-proximal contiguity information are sequenced to determine the methylation status of the nucleic acids with preserved spatial-proximal contiguity information.

B22. The method of any one of embodiments B1 to B19, wherein step (e) generates nucleic acids with preserved spatial-proximal contiguity information and the nucleic acids with preserved spatial-proximal contiguity information are sequenced to produce sequence readouts.

B23. The method of embodiment B22, wherein the sequencing is at a depth of 30x or less.

B24. The method of embodiment B22 or B23, wherein the sequence readouts have a % of long-range cis readouts greater than the % of long-range cis readouts produced without contact with a denaturing detergent at a temperature greater than 65° C.

B25. The method of embodiment B24, wherein % of long-range cis readouts is greater than 40% of the readouts.

B26. The method of any one of embodiments B1 to B19, wherein the formalin-fixed paraffin-embedded (FFPE) sample has an archival period of about 4 years to about 20 years.

B27. The method of any one of embodiments B1 to B19, wherein the formalin-fixed paraffin-embedded (FFPE) sample has an archival period of about 20 years to about 70 years.

B28. The method of embodiment B26 or B27, wherein step (e) generates nucleic acids with preserved spatial-proximal contiguity information and the nucleic acids with preserved spatial-proximal contiguity information are sequenced to produce sequence readouts.

B29. The method of embodiment B28, wherein the sequencing at a depth of 30x or less.

B30. The method of embodiment B28 or B29, wherein the sequence readouts have a % of long-range cis readouts greater than the % of long-range cis readouts produced without contact with a denaturing detergent at a temperature greater than 65° C.

B31. The method of any one of embodiments B1 to B19, wherein the nucleic acid obtained from the formalin-fixed paraffin-embedded (FFPE) sample is less than 200 ng.

B32. The method of embodiment B31, wherein step (e) generates nucleic acids with preserved spatial-proximal contiguity information and the nucleic acids with preserved spatial-proximal contiguity information are sequenced to produce sequence readouts.

B33. The method of embodiment B32, wherein the sequencing at a depth of 30x or less.

B34. The method of embodiment B32 or B33, wherein the sequence read-outs have a % of long-range cis readouts greater than the % of long-range cis readouts produced without contact with a denaturing detergent at a temperature greater than 65° C.

B35. The method of embodiment B34, wherein % of long-range cis readouts is greater than 40% of the readouts.

B36. The method of any one of embodiments B1 to B35, wherein the method is essentially carried out using automated equipment.

B37. The method of any one of embodiments B1 to B36, wherein after step (e) crosslinking is reversed by contacting the sample with proteinase K at a temperature of less than 68° C. for about 30 minutes.

B38. The method of embodiment B37, wherein the temperature is about 55° C.

B38.1. The method of embodiment B38, wherein the temperature is 55° C.

B39. The method of any one of embodiments B1 to B36, wherein after step (e) crosslinking is reversed by incubating the sample at a temperature of about 95° C. for about 1 hour in the absence of proteinase K.

B39.1. The method of embodiment B39, wherein after step (e) crosslinking is reversed by incubating the sample at a temperature of 95° C. for 1 hour in the absence of proteinase K.

C1. A method for preparing nucleic acids from a formalin-fixed paraffin-embedded (FFPE) sample that preserves spatial-proximal contiguity information comprising:
  a) providing a formalin-fixed paraffin-embedded sample, that has not been de-waxed/rehydrated;
  b) contacting the formalin-fixed paraffin-embedded sample with lysis buffer, thereby generating a lysed sample;
  c) contacting the lysed sample with a denaturing detergent at a temperature greater than 65° C., thereby generating a solubilized and decompacted sample; and
  d) contacting the solubilized and decompacted sample with one or more reagents that preserve spatial-proximal contiguity information in the nucleic acids of the solubilized and decompacted sample.

C1.1. The method of embodiment C1, wherein the formalin-fixed paraffin-embedded (FFPE) sample is a tissue sample.

C1.2. The method of embodiment C1 or C1.1, wherein the dewaxed/rehydrated sample is contacted with an extracellular matrix protease prior to contact with the lysis buffer.

C1.3. The method of embodiment C1.2, wherein the protease is a collagenase and/or a dispase.

C1.4. The method of embodiment C1.3, wherein the collagenase is ColI, ColIII or ColIV and the dispase is Dispase I.

C2. The method of any one of embodiments C1 to C1.4, wherein contact with the denaturing detergent is greater than 10 minutes.

C3. The method of embodiment C2, wherein contact with the denaturing detergent is 15 to 80 minutes.

C3.1 The method of embodiment C3, wherein contact with the denaturing detergent is 30 to 50 minutes.

C4. The method of embodiment C3.1, wherein contact with the denaturing detergent is about 40 minutes.

C4.1. The method of embodiment C4, wherein contact with the denaturing is 40 minutes.

C5. The method of any one of embodiments C1 to C4.1, wherein the temperature is greater than 65° C. and less than 80° C.

C6. The method of embodiment C5, wherein the temperature is between 70° C. and 80° C.

C7. The method of embodiment C6, wherein the temperature is about 74° C.

C7.1. The method of embodiment C7, wherein the temperature is 74° C.

C7.2. The method of any one of embodiments C1-C1.4, wherein contact with the denaturing detergent is for 40 minutes at a temperature of 74° C.

C8. The method of any one of embodiments C1-C7.2, wherein the detergent is sodium dodecyl sulfate (SDS).

C9. The method of any one of embodiments C1-08, wherein one or more reagents that preserve spatial-proximal contiguity information comprise reagents that generate proximity ligated nucleic acid molecules.

C9.1. The method of embodiment C9, wherein the reagents that generate proximity ligated nucleic acid molecules comprise one or more of the following reagents: at least one restriction endonuclease, a DNA polymerase, a plurality of nucleotides comprising at least one biotinylated nucleotide, and a ligase.

C9.2. The method of embodiment C9.1, comprising two restriction endonucleases.

C10. The method of any one of embodiments C9 to C9.2, wherein the proximity ligated nucleic acid molecules are generated in situ.

C11. The method of any one of embodiments C1-08, wherein one or more reagents that preserve spatial-proximal contiguity information comprise solid phase elements that form complexes with spatially proximal nucleic acids of the solubilized and decompacted sample to generate spatially proximal nucleic acid of the solubilized and decompacted sample complexed to solid phase elements.

C12. The method of embodiment C11, wherein the solid phase elements are solid phase substrates functionalized with a nucleic acid crosslinking agent.

C13. The method of embodiment C11, wherein the solid phase elements are solid phase substrates functionalized with an affinity purification molecule and the nucleic acid molecules are labeled with an affinity purification marker.

C13.1. The method of any one of embodiments O11 to C13, wherein the spatially proximal nucleic acid of the solubilized and decompacted sample complexed to solid phase elements is contacted with one or more reagents for compartmentalization and tagging with a molecular barcode.

C13.2. The method of embodiment C13.1, wherein the one or more reagents for compartmentalization comprise a microfluidic compartmentalization device that produces microfluidic droplets or microtiter plate wells into which complexes are diluted.

C13.3. The method of embodiment C13.1 or C13.2, wherein tagging with a molecular barcode is by primer extension polymerization (PEP) or by ligation.

C14. The method of embodiment C11, wherein the solid phase elements are solid phase substrates functionalized with a transposase comprising a barcoded oligonucleotide that generate spatially-proximal nucleic acid comprising a ligated barcoded oligonucleotide and complexed to the solid phase substrate functionalized with a transposase C14.1. The method of embodiment C14, wherein the transposase is Tn5.

C15. The method of any one of embodiments C1 to C14.1, wherein the formalin-fixed paraffin-embedded sample is provided on a solid surface.

C15.1. The method of embodiment C15, wherein the solid surface is a pathology slide.

C16. The method of any one of embodiments C1 to C8, wherein one or more reagents that preserve spatial-proximal contiguity information comprise reagents that compartmentalize and attach compartment-specific molecular barcodes to the nucleic acids of the solubilized and decompacted sample.

C16.1. The method of embodiment C16, wherein the one or more reagents that compartmentalize comprise a microfluidic compartmentalization device that produces microfluidic droplets or microtiter plate wells into which complexes are diluted.

C16.2. The method of embodiment C16 or C16.1, wherein the one or more reagents that tag by attaching compartment-specific molecular barcodes comprise reagents for primer extension polymerization (PEP), reagents for ligation or a transposase comprising a barcoded oligonucleotide.

C17. The method of any one of embodiments C1 to C16.2, wherein the formalin-fixed paraffin-embedded sample is provided as a tissue section of about 5 um to about 10 um in thickness.

C18. The method of any one of embodiments, C1 to C8, wherein one or more reagents that preserve spatial-proximal contiguity information comprise a Tn5 tetramer.

C19. The method of any one of embodiments, C1 to C18, wherein step (d) generates nucleic acids with preserved spatial-proximal contiguity information and the nucleic acids with preserved spatial-proximal contiguity information are subjected to bisulfite treatment to generate bisulfite treated nucleic acids with preserved spatial-proximal contiguity information.

C20. The method of embodiment C19, wherein the bisulfite treated nucleic acids with preserved spatial-proximal contiguity information are sequenced to determine the methylation status of the nucleic acids with preserved spatial-proximal contiguity information.

C21. The method of any one of embodiments C1 to C18, wherein step (d) generates nucleic acids with preserved spatial-proximal contiguity information and the nucleic acids with preserved spatial-proximal contiguity information are sequenced to produce sequence readouts.

C22. The method of embodiment C21, wherein the sequencing is at a depth of 30× or less.

C23. The method of embodiment C21 or C22, wherein the sequence readouts have a % of long-range cis readouts greater than the % of long-range cis readouts produced without contact with a denaturing detergent at a temperature greater than 65° C.

C24. The method of embodiment C23, wherein % of long-range cis readouts is greater than 40% of the readouts.

C25. The method of any one of embodiments C1 to C18, wherein the formalin-fixed paraffin-embedded (FFPE) sample has an archival period of about 4 years to about 20 years.

C26. The method of any one of embodiments C1 to C18, wherein the formalin-fixed paraffin-embedded (FFPE) sample has an archival period of about 20 years to about 70 years.

C27. The method of embodiment C25 or C26, wherein step (d) generates nucleic acids with preserved spatial-proximal contiguity information and the nucleic acids with preserved spatial-proximal contiguity information are sequenced to produce sequence readouts.

C28. The method of embodiment C27, wherein the sequencing at a depth of 30× or less.

C29. The method of embodiments, C27 or C28, wherein the sequence readouts have a % of long-range cis readouts greater than the % of long-range cis readouts produced without contact with a denaturing detergent at a temperature greater than 65° C.

C30. The method of any one of embodiments C1 to C18, wherein the nucleic acid obtained from the formalin-fixed paraffin-embedded (FFPE) sample is less than 200 ng.

C31. The method of embodiment C30, wherein step (d) generates nucleic acids with preserved spatial-proximal contiguity information and the nucleic acids with preserved spatial-proximal contiguity information are sequenced to produce sequence readouts.

C32. The method of embodiment C31, wherein the sequencing at a depth of 30× or less.

C33. The method of embodiment C31 or C32, wherein the sequence read-outs have a % of long-range cis readouts greater than the % of long-range cis readouts produced without contact with a denaturing detergent at a temperature greater than 65° C.

C34. The method of embodiment C33, wherein % of long-range cis readouts is greater than 40% of the readouts.

C35. The method of any one of embodiments C1 to C34, wherein the method is essentially carried out using automated equipment.

C36. The method of any one of embodiments C1 to C35, wherein after step (d) crosslinking is reversed by contacting the sample with proteinase K at a temperature of less than 68° C. for about 30 minutes.

C37. The method of embodiment C36, wherein the temperature is about 55° C.

C37.1. The method of embodiment C37, wherein the temperature is 55° C.

C38. The method of any one of embodiments C1 to C35, wherein after step (d) crosslinking is reversed by incubating the sample at a temperature of about 95° C. for about 1 hour in the absence of proteinase K.

C38.1. The method of embodiment C38, wherein after step (d) crosslinking is reversed by incubating the sample at a temperature of 95° C. for 1 hour in the absence of proteinase K.

D1. A method for preparing nucleic acids from a formalin-fixed paraffin-embedded (FFPE) sample that preserves spatial-proximal contiguity information comprising:
  a) providing a formalin-fixed paraffin-embedded sample, that has not been de-waxed/rehydrated;
  b) contacting the formalin-fixed paraffin-embedded sample with a denaturing detergent at a temperature greater than 65° C., thereby generating a solubilized and decompacted sample; and
  c) contacting the solubilized and decompacted sample with one or more reagents that preserve spatial-proximal contiguity information in the nucleic acids of the solubilized and decompacted sample.

D1.1. The method of embodiment D1, wherein the formalin-fixed paraffin-embedded (FFPE) sample is a tissue sample.

D1.2. The method of embodiment D1 or D1.1, wherein the dewaxed/rehydrated sample is contacted with an extracellular matrix protease prior to contact with a denaturing detergent.

D1.3. The method of embodiment D1.2, wherein the protease is a collagenase and/or a dispase.

D1.4. The method of embodiment D1.3, wherein the collagenase is ColI, ColIII or ColIV and the dispase is Dispase I.

D2. The method of any one of embodiments D1, to D1.4, wherein contact with the denaturing detergent is for greater than 10 minutes.

D3. The method of embodiment D2, wherein contact with the denaturing detergent is 15 to 80 minutes.

D3.1. The method of embodiment D3, wherein contact with the denaturing detergent is 30 to 50 minutes.

D4. The method of embodiment D3.1, wherein contact with the denaturing detergent is about 40 minutes.

D4.1. The method of embodiment D4, wherein contact with the denaturing detergent is 40 minutes.

D5. The method of any one of embodiments D1-D4.1, wherein the temperature is greater than 65° C. and less than 80° C.

D6. The method of embodiment D5, wherein the temperature is between 70° C. and 80° C.

D7. The method of embodiment D6, wherein the temperature is about 74° C.

D7.1. The method of embodiment D7, wherein the temperature is 74° C.

D7.2. The method of any one of embodiments D1 to D1.4, wherein contact with the denaturing detergent is for 40 minutes at a temperature of 74° C.

D8. The method of any one of embodiments D1-D7.2, wherein the detergent is sodium dodecyl sulfate (SDS).

D9. The method of any one of embodiments D1-D8, wherein one or more reagents that preserve spatial-proximal contiguity information comprise reagents that generate proximity ligated nucleic acid molecules.

D9.1. The method of embodiment D9, wherein the reagents that generate proximity ligated nucleic acid molecules comprise one or more of at least one restriction endonuclease, a DNA polymerase, a plurality of nucleotides comprising at least one biotinylated nucleotide, and a ligase.

D9.2. The method of embodiment D9.1, comprising two restriction endonucleases.

D10. The method of any one of embodiments D9 to D9.2, wherein the proximity ligated nucleic acid molecules are generated in situ.

D11. The method of any one of embodiments D1-D8, wherein one or more reagents that preserve spatial-proximal contiguity information comprise solid phase elements that form complexes with spatially-proximal nucleic acids of the solubilized and decompacted sample to generate spatially-proximal nucleic acid of the solubilized and decompacted sample complexed to solid phase elements.

D12. The method of embodiment D11, wherein the solid phase elements are solid phase substrates functionalized with a nucleic acid crosslinking agent.

D13. The method of embodiment D11, wherein the solid phase elements are solid phase substrates functionalized with an affinity purification molecule and the nucleic acid molecules are labeled with an affinity purification marker.

D13.1. The method of any one of embodiments D11 to D13, wherein the spatially proximal nucleic acid of the solubilized and decompacted sample complexed to solid phase elements is contacted with one or more reagents for compartmentalization and tagging with a molecular barcode.

D13.2. The method of embodiment D13.1, wherein the one or more reagents for compartmentalization comprise a microfluidic compartmentalization device that produces microfluidic droplets or microtiter plate wells into which complexes are diluted.

D13.3. The method of embodiment D13.1 or D13.2, wherein tagging with a molecular barcode is by primer extension polymerization (PEP) or by ligation.

D14. The method of embodiment D11, wherein the solid phase elements are solid phase substrates functionalized with a transposase comprising a barcoded oligonucleotide that generate spatially-proximal nucleic acid comprising a ligated barcoded oligonucleotide and complexed to the solid phase substrate functionalized with a transposase.

D14.1. The method of embodiment D14, wherein the transposase is Tn5.

D15. The method of any one of embodiments D1 to D14.1, wherein the formalin-fixed paraffin-embedded sample is provided on a solid surface.

D15.1. The method of embodiment D15.1, wherein the solid surface is a pathology slide.

D16. The method of any one of embodiments D1 to D8, wherein one or more reagents that preserve spatial-proximal contiguity information comprise reagents that compartmentalize and attach compartment-specific molecular barcodes to the nucleic acids of the solubilized and decompacted sample.

D16.1. The method of embodiment D16, wherein the one or more reagents that compartmentalize comprise a microfluidic compartmentalization device that produces microfluidic droplets or microtiter plate wells into which complexes are diluted.

D16.2. The method of embodiment D16 or D16.1, wherein the one or more reagents that tag by attaching compartment-specific molecular barcodes comprise reagents for primer extension polymerization (PEP), reagents for ligation or a transposase comprising a barcoded oligonucleotide.

D17. The method of any one of embodiments D1 to D16.2, wherein the formalin-fixed paraffin-embedded sample is provided as a tissue section of about 5 um to about 10 um in thickness.

D18. The method of embodiments D17, wherein the formalin-fixed paraffin-embedded sample is provided as a tissue section of about 5 um in thickness.

D19. The method of any one of embodiments, D1 to D8, wherein one or more reagents that preserve spatial-proximal contiguity information comprise a Tn5 tetramer.

D20. The method of any one of embodiments, D1 to D19, wherein step (c) generates nucleic acids with preserved spatial-proximal contiguity information and the nucleic acids with preserved spatial-proximal contiguity information are subjected to bisulfite treatment to generate bisulfite treated nucleic acids with preserved spatial-proximal contiguity information.

D21. The method of embodiment D20, wherein the bisulfite treated nucleic acids with preserved spatial-proximal contiguity information are sequenced to determine the methylation status of the nucleic acids with preserved spatial-proximal contiguity information.

D22. The method of any one of embodiments D1 to D19, wherein step (c) generates nucleic acids with preserved spatial-proximal contiguity information and the nucleic acids with preserved spatial-proximal contiguity information are sequenced to produce sequence readouts.

D23. The method of embodiment D22, wherein the sequencing is at a depth of 30× or less.

D24. The method of embodiment D22 or D23, wherein the sequence readouts have a % of long-range cis readouts greater than the % of long-range cis readouts produced without contact with a denaturing detergent at a temperature greater than 65° C.

D25. The method of embodiment D24, wherein % of long-range cis readouts is greater than 40% of the readouts.

D26. The method of any one of embodiments D1 to D19, wherein the formalin-fixed paraffin-embedded (FFPE) sample has an archival period of about 4 years to about 20 years.

D27. The method of any one of embodiments D1 to D19, wherein the formalin-fixed paraffin-embedded (FFPE) sample has an archival period of about 20 years to about 70 years.

D28. The method of embodiment D26 or D27, wherein step (c) generates nucleic acids with preserved spatial-proximal contiguity information and the nucleic acids with preserved spatial-proximal contiguity information are sequenced to produce sequence readouts.

D29. The method of embodiment D28, wherein the sequencing at a depth of 30× or less.

D30. The method of embodiment D28 or D29, wherein the sequence readouts have a % of long-range cis readouts greater than the % of long-range cis readouts produced without contact with a denaturing detergent at a temperature greater than 65° C.

D31. The method of any one of embodiments D1 to D19, wherein the nucleic acid obtained from the formalin-fixed paraffin-embedded (FFPE) sample is less than 200 ng.

D32. The method of embodiment D31, wherein step (c) generates nucleic acids with preserved spatial-proximal contiguity information and the nucleic acids with preserved spatial-proximal contiguity information are sequenced to produce sequence readouts.

D33. The method of embodiment D32, wherein the sequencing at a depth of 30× or less.

D34. The method of embodiment D32 or D33, wherein the sequence read-outs have a % of long-range cis readouts greater than the % of long-range cis readouts produced without contact with a denaturing detergent at a temperature greater than 65° C.

D35. The method of embodiment D34, wherein % of long-range cis readouts is greater than 40% of the readouts.

D36. The method of any one of embodiments D1 to D35, wherein the method is essentially carried out using automated equipment.

D37. The method of any one of embodiments D1 to D36, wherein after step (c) crosslinking is reversed by contacting the sample with proteinase K at a temperature of less than 68° C. for about 30 minutes.

D37.1. The method of embodiment D37, wherein the temperature is about 55° C.

D37.2. The method of embodiment D37.1, wherein the temperature is 55° C.

D38. The method of any one of embodiments D1 to D36, wherein after step (c) crosslinking is reversed by incubating the sample at a temperature of about 95° C. for about 1 hour in the absence of proteinase K.

D38.1. The method of embodiment D38, wherein after step (c) crosslinking is reversed by incubating the sample at a temperature of 95° C. for 1 hour in the absence of proteinase K.

E1. A method for preparing nucleic acids from a deeply formalin-fixed sample that preserves spatial-proximal contiguity information comprising:
  a) providing a deeply formalin-fixed sample;
  b) contacting the deeply formalin-fixed sample with lysis buffer, thereby generated a lysed sample;
  c) contacting the lysed sample with a denaturing detergent at a temperature greater than 65° C., thereby generating a solubilized and decompacted sample; and
  d) contacting the solubilized and decompacted sample with one or more reagents that preserve spatial-proximal contiguity information in the nucleic acids of the solubilized and decompacted sample.

E1.1. The method of embodiment E1, wherein the deeply formalin-fixed sample is a tissue sample.

E1.2. The method of embodiment E1 or E1.1, wherein the deeply formalin-fixed sample is contacted with an extracellular matrix protease prior to contact with lysis buffer.

E1.3. The method of embodiment E1.2, wherein the protease is a collagenase and/or a dispase.

E1.4. The method of embodiment E1.3, wherein the collagenase is ColI, ColIII or ColIV and the dispase is Dispase I.

E1.5. The method of any one of embodiments E1 to E1.4, wherein the deeply formalin-fixed sample is pulverized.

E2. The method of any one of embodiments E1 to E1.5, wherein contact with the denaturing detergent is for greater than 10 minutes.

E3. The method of embodiment E2, wherein contact with the denaturing detergent is 15 to 80 minutes.

E3.1. The method of embodiment E3, wherein contact with the denaturing detergent is 30 to 50 minutes.

E4. The method of embodiment E3.1, wherein contact with the denaturing detergent is about 40 minutes.

E4.1. The method of embodiment E4, wherein contact with the denaturing detergent is 40 minutes.

E5. The method of any one of embodiments E1 to E4.1, wherein the temperature is greater than 65° C. and less than 80° C.

E6. The method of embodiment E5, wherein the temperature is between 70° C. and 80° C.

E7. The method of embodiment E6, wherein the temperature is about 74° C.

E7.1. The method of embodiment E7, wherein the temperature is 74° C.

E7.2. The method of any one of embodiments E1-E1.5, wherein contact with the denaturing detergent is for 40 minutes at a temperature of 74° C.

E8. The method of any one of embodiments E1 to E7.2, wherein the detergent is sodium dodecyl sulfate (SDS).

E9. The method of any one of embodiments E1-E8, wherein one or more reagents that preserve spatial-proximal contiguity information comprise reagents that generate proximity ligated nucleic acid molecules.

E9.1. The method of embodiment E9, wherein the reagents that generate proximity ligated nucleic acid molecules comprise one or more of the following reagents: at least one restriction endonuclease, a DNA polymerase, a plurality of nucleotides comprising at least one biotinylated nucleotide, and a ligase.

E9.2. The method of embodiment E9.1, comprising two restriction endonucleases.

E10. The method of any one of embodiment E9 to E9.2, wherein the proximity ligated nucleic acid molecules are generated in situ.

E11. The method of any one of embodiments E1-E8, wherein one or more reagents that preserve spatial-proximal contiguity information comprise solid phase elements that form complexes with spatially-proximal nucleic acids of the solubilized and decompacted sample to generate spatially-proximal nucleic acid of the solubilized and decompacted sample complexed to solid phase elements.

E12. The method of embodiment E11, wherein the solid phase elements are solid phase substrates functionalized with a nucleic acid crosslinking agent.

E13. The method of embodiment E11, wherein the solid phase elements are solid phase substrates functionalized with an affinity purification molecule and the nucleic acid molecules are labeled with an affinity purification marker.

E13.1. The method of any one of embodiments E11 to E13, wherein the spatially proximal nucleic acid of the solubilized and decompacted sample complexed to solid phase elements is contacted with one or more reagents for compartmentalization and tagging with a molecular barcode.

E13.2. The method of embodiment E13.1, wherein the one or more reagents for compartmentalization comprise a microfluidic compartmentalization device that produces microfluidic droplets or microtiter plate wells into which complexes are diluted.

E13.3. The method of embodiment E13.1 or E13.2, wherein tagging with a molecular barcode is by primer extension polymerization (PEP) or by ligation.

E14. The method of embodiment E11, wherein the solid phase elements are solid phase substrates functionalized with a transposase comprising a barcoded oligonucleotide that generate spatially-proximal nucleic acid comprising a ligated barcoded oligonucleotide that are complexed to the solid phase substrate functionalized with a transposase E14.1. The method of embodiment E14, wherein the transposase is Tn5.

E15. The method of any one of embodiments E1 to E14.1, wherein the deeply formalin-fixed sample is provided on a solid surface.

E15.1. The method of embodiment E15.1, wherein the solid surface is a pathology slide.

E16. The method of any one of embodiments E1 to E8, wherein one or more reagents that preserve spatial-proximal contiguity information comprise reagents that compartmentalize and attach compartment-specific molecular barcodes to the nucleic acids of the solubilized and decompacted sample.

E16.1. The method of embodiment E16, wherein the one or more reagents that compartmentalize are a microfluidic compartmentalization device that produces microfluidic droplets or microtiter plate wells into which complexes are diluted.

E16.2. The method of embodiment E16 or E16.1, wherein the one or more reagents that tag by attaching compartment-specific molecular barcodes comprise reagents for primer extension polymerization (PEP), reagents for ligation or a transposase comprising a barcoded oligonucleotide.

E17. The method of any one of embodiments, E1 to E8, wherein one or more reagents that preserve spatial-proximal contiguity information comprise a Tn5 tetramer.

E18. The method of any one of embodiments, E1 to E17, wherein step (d) generates nucleic acids with preserved spatial-proximal contiguity information and the nucleic acids with preserved spatial-proximal contiguity information are subjected to bisulfite treatment to generate bisulfite treated nucleic acids with preserved spatial-proximal contiguity information.

E19. The method of embodiment E18, wherein the bisulfite treated nucleic acids with preserved spatial-proximal contiguity information are sequenced to determine the methylation status of the nucleic acids with preserved spatial-proximal contiguity information.

E20. The method of any one of embodiments E1 to E17, wherein step (d) generates nucleic acids with preserved spatial-proximal contiguity information and the nucleic acids with preserved spatial-proximal contiguity information are sequenced to produce sequence readouts.

E21. The method of embodiment E20, wherein the sequencing is at a depth of 30× or less.

E22. The method of embodiment E20 or E21, wherein the sequence readouts have a % of long-range cis readouts greater than the % of long-range cis readouts produced without contact with a denaturing detergent at a temperature greater than 65° C.

E23. The method of embodiment E22, wherein % of long-range cis readouts is greater than 40% of the readouts.

E24. The method of any one of embodiments E1 to E17, wherein the deeply formalin-fixed sample has an archival period of about 4 years to about 20 years.

E25. The method of any one of embodiments E1 to E17, wherein the deeply formalin-fixed sample has an archival period of about 20 years to about 70 years.

E26. The method of embodiment E24 or E25, wherein step (d) generates nucleic acids with preserved spatial-proximal contiguity information and the nucleic acids with preserved spatial-proximal contiguity information are sequenced to produce sequence readouts.

E27. The method of embodiment E26, wherein the sequencing at a depth of 30× or less.

E28. The method of embodiment E26 or E27, wherein the sequence readouts have a % of long-range cis readouts greater than the % of long-range cis readouts produced without contact with a denaturing detergent at a temperature greater than 65° C.

E29. The method of any one of embodiments E1 to E17, wherein the nucleic acid obtained from the deeply formalin-fixed sample is less than 200 ng.

E30. The method of embodiment E29, wherein step (d) generates nucleic acids with preserved spatial-proximal contiguity information and the nucleic acids with preserved spatial-proximal contiguity information are sequenced to produce sequence readouts.

E31. The method of embodiment E30, wherein the sequencing at a depth of 30× or less.

E32. The method of embodiment E30 or E31, wherein the sequence read-outs have a % of long-range cis readouts greater than the % of long-range cis readouts produced without contact with a denaturing detergent at a temperature greater than 65° C.

E33. The method of embodiment E32, wherein % of long-range cis readouts is greater than 40% of the readouts.

E34. The method of any one of embodiments E1 to E33, wherein the method is essentially carried out using automated equipment.

E35. The method of any one of embodiments E1 to E34, wherein after step (d) crosslinking is reversed by contacting the sample with proteinase K at a temperature of less than 68° C. for about 30 minutes.

E36. The method of embodiment E35, wherein the temperature is about 55° C.

E37. The method of embodiment E36, wherein the temperature is 55° C.

E38. The method of any one of embodiments E1 to E34, wherein after step (d) crosslinking is reversed by incubating the sample at a temperature of about 95° C. for about 1 hour in the absence of proteinase K.

E38.1. The method of embodiment E38, wherein after step (d) crosslinking is reversed by incubating the sample at a temperature of 95° C. for 1 hour in the absence of proteinase K.

F1. A method for preparing nucleic acids from a sample comprising protein:cfDNA complexes, that preserves spatial-proximal contiguity information, comprising:
  a) providing a sample comprising protein:cfDNA complexes;
  b) crosslinking the protein:cfDNA complexes to neighboring protein:cfDNA complexes; and
  c) contacting the crosslinked protein:cfDNA complexes with one or more reagents that preserve spatial-proximal contiguity information in the cell free DNA of the sample.

F2. The method of embodiment F1, wherein the sample is blood serum, blood plasma or urine.

F2.1. The method of embodiment F1 or F2, wherein the protein:cfDNA complexes are nucleosome complexes or chromatosome complexes.

F2.2. The method of any one of embodiments F1 to F2.1, wherein the protein:cfDNA complexes in the sample are contacted with a solid phase prior to crosslinking, thereby generating protein:cfDNA complexes associated with a solid phase.

F3. The method of embodiment F2.2, wherein the solid phase binds the protein:cfDNA complexes.

F3.1. The method of embodiments F2.2 or F3, wherein the crosslinking agent is formaldehyde.

F4. The method of any one of embodiments F1 to F3.1, wherein one or more reagents that preserve spatial-proximal contiguity information comprise reagents that generate proximity ligated nucleic acid molecules.

F5. The method of embodiment F4, wherein the reagents that generate proximity ligated nucleic acid molecules comprise one or more of a restriction endonuclease, a DNA polymerase, a plurality of nucleotides comprising at least one biotinylated nucleotide, and a ligase.

F6. The method of any one of embodiments F1 to F3.1, wherein the one or more reagents that preserve spatial-proximal contiguity information comprise a Tn5 tetramer.

F7. The method of any one of embodiments F1 to F3.1, wherein the protein:cfDNA complexes are released from the solid support and the one or more reagents that preserve spatial-proximal contiguity information comprise reagents that compartmentalize the protein:cfDNA complexes released from the solid support and tag the compartmentalized protein:cfDNA complexes with a compartment specific molecular barcode.

F7.1. The method of embodiment F7, wherein the one or more reagents that compartmentalize comprise a microfluidic compartmentalization device that produces microfluidic droplets or microtiter plate wells into which complexes are diluted.

F7.2. The method of embodiment F7 or F7.1, wherein the one or more reagents that tag the compartmentalized protein:cfDNA complexes with a compartment specific molecular barcode comprise reagents for primer extension polymerization (PEP), reagents for ligation or a transposase comprising a barcoded oligonucleotide.

F8. The method of any one of embodiments F7 to F7.2, further comprising one or more reagents to affinity purify the protein:cfDNA complexes.

F9. The method of any one of embodiments F1 to F3.1, wherein one or more reagents that preserve spatial-proximal contiguity information comprise Tn5 bound to a solid phase.

F9.1. The method of embodiment F9, wherein the Tn5 comprises a virtual compartment specific molecular barcode.

F10. The method of any one of embodiments, F1 to F9.1, wherein step (c) generates cell free DNA with preserved spatial-proximal contiguity information and the cell free DNA with preserved spatial-proximal contiguity information is subjected to bisulfite treatment to generate bisulfite treated cell free DNA with preserved spatial-proximal contiguity information.

F11. The method of embodiment F10, wherein the bisulfite treated cell free DNA with preserved spatial-proximal contiguity information is sequenced to determine the methylation status of the cell free DNA with preserved spatial-proximal contiguity information.

F12. The method of any one of embodiments F1 to F9.1, wherein step (c) generates nucleic acids with preserved spatial-proximal contiguity information and the nucleic acids with preserved spatial-proximal contiguity information are sequenced to produce sequence readouts.

F13. The method of embodiment F12, wherein the sequencing is at a depth of 30× or less.

F14. The method of any one of embodiments F1 to F13, wherein the method is essentially carried out using automated equipment.

F15. The method of any one of embodiments F1 to F14, wherein after step (c) crosslinking is reversed by contacting the sample with proteinase K at a temperature of less than 68° C. for about 30 minutes.

F16. The method of embodiment F15, wherein the temperature is about 55° C.

F17. The method of embodiment F16, wherein the temperature is 55° C.

F18. The method of any one of embodiments F1 to F14, wherein after step (c) crosslinking is reversed by incubating the sample at a temperature of about 95° C. for about 1 hour in the absence of proteinase K.

F19. The method of embodiment F18, wherein after step (c) crosslinking is reversed by incubating the sample at a temperature of 95° C. for 1 hour in the absence of proteinase K.

G1. A method for preparing nucleic acid from a sample comprising protein:cfDNA complexes, that preserves spatial-proximal contiguity information, comprising:
  a) providing a sample comprising protein:cfDNA complexes;
  b) contacting the sample with a solid phase, thereby generating protein:cfDNA complexes associated with a solid phase;
  c) cross-linking the protein:cfDNA complexes to neighboring protein:cfDNA complexes or to the solid phase; and
  d) contacting the crosslinked protein:cfDNA complexes with one or more reagents that preserve spatial-proximal contiguity information in the cell free DNA of the sample.

G2. The method of embodiment G1, wherein the sample is blood serum, blood plasma or urine.

G2.1. The method of embodiment G1 or G2, wherein the protein:cfDNA complexes are nucleosome complexes or chromatosome complexes.

G3. The method of any one of embodiments G1 to G2.1, wherein the solid phase binds the protein:cfDNA complexes and the protein:cfDNA complexes bound to the solid phase are contacted with a cross-linking reagent.

G3.1. The method of embodiment G3, wherein the crosslinking agent is formaldehyde.

G4. The method of any one of embodiments G1 to G2.1, wherein the solid phase is coated with a crosslinking agent and the protein:cfDNA complexes are crosslinked to the solid phase.

G4.1. The method of embodiment G4, wherein the crosslinking reagent is psoralen.

G5. The method of any one of embodiments G1 to G4.1, wherein one or more reagents that preserve spatial-proximal contiguity information comprise reagents that generate proximity ligated nucleic acid molecules.

G5.1. The method of embodiment G5, wherein the reagents that generate proximity ligated nucleic acid molecules comprise one or more of a restriction endonuclease, a DNA polymerase, a plurality of nucleotides comprising at least one biotinylated nucleotide, and a ligase.

G6. The method of any one of embodiments G1 to G4.1, wherein the one or more reagents that preserve spatial-proximal contiguity information comprise a Tn5 tetramer.

G7. The method of any one of embodiments G1 to G4.1, wherein one or more reagents comprise reagents that compartmentalize the protein:cfDNA complexes released from the solid support and tag the compartmentalized protein:cfDNA complexes with a compartment specific molecular barcode.

G7.1. The method of embodiment G7, wherein the one or more reagents that compartmentalize comprise a microfluidic compartmentalization device that produces microfluidic droplets or microtiter plate wells into which complexes are diluted.

G7.2. The method of embodiment G7 or G7.1, wherein the one or more reagents that tag the compartmentalized protein:cfDNA complexes with a compartment specific molecular barcode comprise reagents for primer extension polymerization (PEP), reagents for ligation or a transposase comprising a barcoded oligonucleotide.

G8. The method of any one of embodiments G7 to G7.2, further comprising one or more reagents to affinity purify the protein:cfDNA complexes prior to compartmentalization.

G9. The method of any one of embodiments G1-G4.1, wherein one or more reagents that preserve spatial-proximal contiguity information comprise Tn5 bound to a solid phase.

G9.1. The method of embodiment G9, wherein the Tn5 comprises a virtual compartment specific molecular barcode.

G10. The method of any one of embodiments, G1 to G9.1, wherein step (d) generates cell free DNA with preserved spatial-proximal contiguity information and the cell free DNA with preserved spatial-proximal contiguity information is subjected to bisulfite treatment to generate bisulfite treated cell free DNA with preserved spatial-proximal contiguity information.

G11. The method of embodiment G10, wherein the bisulfite treated cell free DNA with preserved spatial-proximal contiguity information is sequenced to determine the methylation status of the cell free DNA with preserved spatial-proximal contiguity information.

G12. The method of any one of embodiments G1 to G9.1, wherein step (d) generates nucleic acids with preserved spatial-proximal contiguity information and the nucleic acids with preserved spatial-proximal contiguity information are sequenced to produce sequence readouts.

G13. The method of embodiment G12, wherein the sequencing is at a depth of 30× or less.

G14. The method of any one of embodiments G1 to G13, wherein the method is essentially carried out using automated equipment.

G15. The method of any one of embodiments G1 to G14, wherein after step (d) crosslinking is reversed by contacting the sample with proteinase K at a temperature of less than 68° C. for about 30 minutes.

G16. The method of embodiment G15, wherein the temperature is about 55° C.

G17. The method of embodiment G16, wherein the temperature is 55° C.

G18. The method of any one of embodiments G1 to G14, wherein after step (d) crosslinking is reversed by incubating the sample at a temperature of about 95° C. for about 1 hour in the absence of proteinase K.

G19. The method of embodiment G18, wherein after step (d) crosslinking is reversed by incubating the sample at a temperature of 95° C. for 1 hour in the absence of proteinase K.

H1 A method for preparing nucleic acids from a formalin-fixed paraffin-embedded (FFPE) sample, that preserves spatial-proximal contiguity information, comprising:
  a) providing a formalin-fixed paraffin-embedded sample;
  b) de-waxing the sample to produce a de-waxed sample;
  c) rehydrating the de-waxed sample, thereby generating a de-waxed/rehydrated sample;
  d) contacting the de-waxed/rehydrated sample sample with lysis buffer, thereby generating a lysed sample;

e) contacting the lysed sample with sodium dodecyl sulfate (SDS) at a temperature of 74° C. for 40 minutes, thereby generating a solubilized and decompacted sample; and f) contacting the solubilized and decompacted sample with one or more reagents that generate proximity ligated nucleic acid molecules in situ, thereby preserving spatial-proximal contiguity information in the nucleic acids of the solubilized and decompacted sample.

H1.1. The method of embodiment H1, wherein the formalin-fixed paraffin-embedded (FFPE) sample is a tissue sample.

H2. The method of embodiment H1 or H1.1, wherein the dewaxed/rehydrated sample is contacted with an extracellular matrix protease prior to contact with the lysis buffer.

H2.1. The method of embodiment H2, wherein the protease is a collagenase and/or a dispase.

H2.2. The method of embodiment H2.1, wherein the collagenase is ColI, ColIII or ColIV and the dispase is Dispase I.

H3. The method of any one of embodiments, H1 to H2.2, wherein step (f) generates nucleic acids with preserved spatial-proximal contiguity information and the nucleic acids with preserved spatial-proximal contiguity information are subjected to bisulfite treatment to generate bisulfite treated nucleic acids with preserved spatial-proximal contiguity information.

H4. The method of embodiment H3, wherein the bisulfite treated nucleic acids with preserved spatial-proximal contiguity information are sequenced to determine the methylation status of the nucleic acids with preserved spatial-proximal contiguity information.

H5. The method of any one of embodiments H1 to H2.2, wherein step (f) generates nucleic acids with preserved spatial-proximal contiguity information and the nucleic acids with preserved spatial-proximal contiguity information are sequenced to produce sequence readouts.

H6. The method of embodiment H5, wherein the sequencing is at a depth of 30× or less.

H7. The method of embodiment H5 or H6, wherein the sequence readouts have a % of long-range cis readouts greater than the % of long-range cis readouts produced without contact with a denaturing detergent at a temperature of 74° C. for 40 minutes.

H8. The method of embodiment H7, wherein % of long-range cis readouts is greater than 40% of the readouts.

H9. The method of any one of embodiments H1 to H2.2, wherein the formalin-fixed paraffin-embedded (FFPE) sample has an archival period of about 4 years to about 20 years.

H10. The method of any one of embodiments H1 to H2.2, wherein the formalin-fixed paraffin-embedded (FFPE) sample has an archival period of about 20 years to about 70 years.

H11. The method of embodiment H9 or H10, wherein step (f) generates nucleic acids with preserved spatial-proximal contiguity information and the nucleic acids with preserved spatial-proximal contiguity information are sequenced to produce sequence readouts.

H12. The method of embodiment H11, wherein the sequencing at a depth of 30× or less.

H13. The method of embodiment H11 or H12, wherein the sequence readouts have a % of long-range cis readouts greater than the % of long-range cis readouts produced without contact with a denaturing detergent at a temperature of 74° C. for 40 minutes.

H14. The method of any one of embodiments H1 to H2.2, wherein the nucleic acid obtained from the formalin-fixed paraffin-embedded (FFPE) sample is less than 200 ng.

H15. The method of embodiment H14, wherein step (f) generates nucleic acids with preserved spatial-proximal contiguity information and the nucleic acids with preserved spatial-proximal contiguity information are sequenced to produce sequence readouts.

H16. The method of embodiment H15, wherein the sequencing at a depth of 30× or less.

H17. The method of embodiment H15 or H16, wherein the sequence read-outs have a % of long-range cis readouts greater than the % of long-range cis readouts produced without contact with a denaturing detergent at a temperature of 74° C. for 40 minutes.

H18. The method of embodiment H17, wherein % of long-range cis readouts is greater than 40% of the readouts.

H19. The method of any one of embodiments H1 to H18, wherein the method is essentially carried out using automated equipment.

H20. The method of any one of embodiments H1 to H19, wherein after step (f) crosslinking is reversed by contacting the sample with proteinase K at a temperature of less than 68° C. for about 30 minutes.

H21. The method of embodiment H20, wherein the temperature is about 55° C.

H22. The method of embodiment H21, wherein the temperature is 55° C.

H23. The method of any one of embodiments H1 to H19, wherein after step (f) crosslinking is reversed by incubating the sample at a temperature of about 95° C. for about 1 hour in the absence of proteinase K.

H24. The method of embodiment H23, wherein after step (f) crosslinking is reversed by incubating the sample at a temperature of 95° C. for 1 hour in the absence of proteinase K.

I1. A method for preparing nucleic acids from a deeply formalin-fixed sample that preserves spatial-proximal contiguity information comprising:
  a) providing a deeply formalin-fixed sample;
  b) contacting the deeply formalin-fixed sample with a denaturing detergent at a temperature greater than 65° C., thereby generating a solubilized and decompacted sample; and
  c) contacting the solubilized and decompacted sample with one or more reagents that preserve spatial-proximal contiguity information in the nucleic acids of the solubilized and decompacted sample.

I1.1. The method of embodiment I1, wherein the deeply formalin-fixed sample is a tissue sample.

I1.2. The method of embodiment I1 or I1.1, wherein the deeply formalin-fixed sample is contacted with an extracellular matrix protease prior to contact with lysis buffer.

I1.3. The method of embodiment I1.2, wherein the protease is a collagenase and/or a dispase.

I1.4. The method of embodiment I1.3, wherein the collagenase is ColI, ColIII or ColIV and the dispase is Dispase I.

I1.5. The method of any one of embodiments I1 to I1.4, wherein the deeply formalin-fixed sample is pulverized.

I2. The method of any one of embodiments I1 to I1.5, wherein contact with the denaturing detergent is for greater than 10 minutes.

I3. The method of embodiment I2, wherein contact with the denaturing detergent is 15 to 80 minutes.

I3.1. The method of embodiment I3, wherein contact with the denaturing detergent is 30 to 50 minutes.

I4. The method of embodiment I3.1, wherein contact with the denaturing detergent is about 40 minutes.

I4.1. The method of embodiment I4, wherein contact with the denaturing detergent is 40 minutes.

I5. The method of any one of embodiments I1 to I4.1, wherein the temperature is greater than 65° C. and less than 80° C.

I6. The method of embodiment I5, wherein the temperature is between 70° C. and 80° C.

I7. The method of embodiment I6, wherein the temperature is about 74° C.

I7.1. The method of embodiment I7, wherein the temperature is 74° C.

I7.2. The method of any one of embodiments I1-I1.5, wherein contact with the denaturing detergent is for 40 minutes at a temperature of 74° C.

I8. The method of any one of embodiments I1 to I7.2, wherein the detergent is sodium dodecyl sulfate (SDS).

I9. The method of any one of embodiments I1-I8, wherein one or more reagents that preserve spatial-proximal contiguity information comprise reagents that generate proximity ligated nucleic acid molecules.

I9.1. The method of embodiment I9, wherein the reagents that generate proximity ligated nucleic acid molecules comprise one or more of the following reagents: at least one restriction endonuclease, a DNA polymerase, a plurality of nucleotides comprising at least one biotinylated nucleotide, and a ligase.

I9.2. The method of embodiment I9.1, comprising two restriction endonucleases.

I10. The method of any one of embodiment I9 to I9.2, wherein the proximity ligated nucleic acid molecules are generated in situ.

I11. The method of any one of embodiments I1-I8, wherein one or more reagents that preserve spatial-proximal contiguity information comprise solid phase elements that form complexes with spatially-proximal nucleic acids of the solubilized and decompacted sample to generate spatially-proximal nucleic acid of the solubilized and decompacted sample complexed to solid phase elements.

I12. The method of embodiment I11, wherein the solid phase elements are solid phase substrates functionalized with a nucleic acid crosslinking agent.

I13. The method of embodiment I11, wherein the solid phase elements are solid phase substrates functionalized with an affinity purification molecule and the nucleic acid molecules are labeled with an affinity purification marker.

I13.1. The method of any one of embodiments I11 to I13, wherein the spatially proximal nucleic acid of the solubilized and decompacted sample complexed to solid phase elements is contacted with one or more reagents for compartmentalization and tagging with a molecular barcode.

I13.2. The method of embodiment I13.1, wherein the one or more reagents for compartmentalization comprise a microfluidic compartmentalization device that produces microfluidic droplets or microtiter plate wells into which complexes are diluted.

I13.3. The method of embodiment I13.1 or I13.2, wherein tagging with a molecular barcode is by primer extension polymerization (PEP) or by ligation.

I14. The method of embodiment I11, wherein the solid phase elements are solid phase substrates functionalized with a transposase comprising a barcoded oligonucleotide that generate spatially-proximal nucleic acid comprising a ligated barcoded oligonucleotide that are complexed to the solid phase substrate functionalized with a transposase I14.1. The method of embodiment I14, wherein the transposase is Tn5.

I15. The method of any one of embodiments I1 to I14.1, wherein the deeply formalin-fixed sample is provided on a solid surface.

I15.1. The method of embodiment I15.1, wherein the solid surface is a pathology slide.

I16. The method of any one of embodiments I1 to I8, wherein one or more reagents that preserve spatial-proximal contiguity information comprise reagents that compartmentalize and attach compartment-specific molecular barcodes to the nucleic acids of the solubilized and decompacted sample.

I16.1. The method of embodiment I16, wherein the one or more reagents that compartmentalize are a microfluidic compartmentalization device that produces microfluidic droplets or microtiter plate wells into which complexes are diluted.

I16.2. The method of embodiment I16 or I16.1, wherein the one or more reagents that tag by attaching compartment-specific molecular barcodes comprise reagents for primer extension polymerization (PEP), reagents for ligation or a transposase comprising a barcoded oligonucleotide.

I17. The method of any one of embodiments, I1 to I8, wherein one or more reagents that preserve spatial-proximal contiguity information comprise a Tn5 tetramer.

I18. The method of any one of embodiments, I1 to I17, wherein step (c) generates nucleic acids with preserved spatial-proximal contiguity information and the nucleic acids with preserved spatial-proximal contiguity information are subjected to bisulfite treatment to generate bisulfite treated nucleic acids with preserved spatial-proximal contiguity information.

I19. The method of embodiment I18, wherein the bisulfite treated nucleic acids with preserved spatial-proximal contiguity information are sequenced to determine the methylation status of the nucleic acids with preserved spatial-proximal contiguity information.

I20. The method of any one of embodiments I1 to I17, wherein step (c) generates nucleic acids with preserved spatial-proximal contiguity information and the nucleic acids with preserved spatial-proximal contiguity information are sequenced to produce sequence readouts.

I21. The method of embodiment I20, wherein the sequencing is at a depth of 30× or less.

I22. The method of embodiment I20 or I21, wherein the sequence readouts have a % of long-range cis readouts greater than the % of long-range cis readouts produced without contact with a denaturing detergent at a temperature greater than 65° C.

I23. The method of embodiment I22, wherein % of long-range cis readouts is greater than 40% of the readouts.

I24. The method of any one of embodiments I1 to I17, wherein the deeply formalin-fixed sample has an archival period of about 4 years to about 20 years.

I25. The method of any one of embodiments I1 to I17, wherein the deeply formalin-fixed sample has an archival period of about 20 years to about 70 years.

I26. The method of embodiment I24 or I25, wherein step (c) generates nucleic acids with preserved spatial-proximal contiguity information and the nucleic acids with preserved spatial-proximal contiguity information are sequenced to produce sequence readouts.

I27. The method of embodiment I26, wherein the sequencing at a depth of 30× or less.

I28. The method of embodiment I26 or I27, wherein the sequence readouts have a % of long-range cis readouts greater than the % of long-range cis readouts produced without contact with a denaturing detergent at a temperature greater than 65° C.

I29. The method of any one of embodiments I1 to I17, wherein the nucleic acid obtained from the deeply formalin-fixed sample is less than 200 ng.

I30. The method of embodiment I29, wherein step (c) generates nucleic acids with preserved spatial-proximal contiguity information and the nucleic acids with preserved spatial-proximal contiguity information are sequenced to produce sequence readouts.

I31. The method of embodiment I30, wherein the sequencing at a depth of 30× or less.

I32. The method of embodiment I30 or I31, wherein the sequence read-outs have a % of long-range cis readouts greater than the % of long-range cis readouts produced without contact with a denaturing detergent at a temperature greater than 65° C.

I33. The method of embodiment I32, wherein % of long-range cis readouts is greater than 40% of the readouts.

I34. The method of any one of embodiments I1 to I33, wherein the method is essentially carried out using automated equipment.

I35. The method of any one of embodiments I1 to I34, wherein after step (c) crosslinking is reversed by contacting the sample with proteinase K at a temperature of less than 68° C. for about 30 minutes.

I36. The method of embodiment I35, wherein the temperature is about 55° C.

I37. The method of embodiment I36, wherein the temperature is 55° C.

I38. The method of any one of embodiments I1 to I34, wherein after step (c) crosslinking is reversed by incubating the sample at a temperature of about 95° C. for about 1 hour in the absence of proteinase K.

I39. The method of embodiment I38, wherein after step (c) crosslinking is reversed by incubating the sample at a temperature of 95° C. for 1 hour in the absence of proteinase K.

J1. A kit comprising:
  a dewaxing reagent;
  a lysis buffer;
  a denaturing detergent; and
  one or more reagents that preserve spatial-proximal contiguity information.

J1.1. The kit of embodiment J1, wherein the dewaxing reagent is xylene or mineral oil.

J1.2. The kit of embodiment J1 or J1.1, wherein the lysis buffer comprises one or more salts, a protease inhibitor and a non-ionic, non-denaturing detergent.

J1.3. The kit of any one of embodiments J1 to J1.2, wherein the denaturing detergent is sodium dodecyl sulfate (SDS).

J1.4. The kit of any one of embodiments J1 to J1.3, comprising a reagent to quench the denaturing-detergent.

J1.5. The kit of embodiment J1.4, wherein the reagent is TritonX-100.

J1.6. The kit of embodiment of any one of embodiments J1 to J1.5, comprising an extracellular matrix protease.

J1.7. The kit of embodiment J1.6, wherein the protease is a collagenase and/or a dispase.

J1.8. The kit of embodiment J1.7, wherein the collagenase is ColI, ColIII or ColIV, and the dispase is Dispase I.

J1.9. The kit of any one of embodiments J1 to J1.8, wherein one or more reagents that preserve spatial-proximal contiguity information comprise reagents that generate proximity ligated nucleic acid molecules.

J1.9.1. The kit of embodiment J1.9, wherein the reagents that generate proximity ligated nucleic acid molecules comprise one or more of the following reagents: at least one restriction endonuclease, a DNA polymerase, a plurality of nucleotides comprising at least one biotinylated nucleotide, and a ligase.

J1.9.2. The kit of embodiment J1.9.1, comprising two restriction endonucleases.

J1.10. The kit of any one of embodiments J1 to J1.8, wherein one or more reagents that preserve spatial-proximal contiguity information comprise solid phase elements.

J1.10.1. The kit of embodiment J1.10, wherein the solid phase elements are beads.

J1.11. The kit of embodiment J1.10 or J1.10.1, wherein the solid phase elements are solid phase substrates functionalized with a nucleic acid crosslinking reagent.

J1.12. The kit of embodiment J1.11, wherein the crosslinking reagent is psoralen.

J1.13. The kit of embodiment J1.10 or J1.10.1, wherein the solid phase elements are solid phase substrates functionalized with an affinity purification molecule.

J1.13.1. The kit of embodiment J1.13, wherein the affinity purification molecule is streptavidin.

J1.13.2. The kit of embodiment J1.13 or J1.13.1, comprising an affinity purification marker.

J1.13.3. The kit of embodiment J1.13.2, wherein the affinity purification marker is biotin.

J1.14. The kit of embodiment J1.10 or J1.10.1, wherein the solid phase elements are solid phase substrates functionalized with a transposase comprising a barcoded oligonucleotide.

J1.15. The kit of embodiment J1.14, wherein the transposase is Tn5.

J1.16. The kit of any one of embodiments J1 to J1.8, wherein one or more reagents that preserve spatial-proximal contiguity information comprise compartment-specific molecular barcodes, reagents that tag by attaching compartment-specific molecular barcodes and/or reagents that compartmentalize.

J1.16.1. The kit of embodiment J1.16, wherein the one or more reagents that compartmentalize comprise a microfluidic compartmentalization device that produces microfluidic droplets or microtiter plate wells into which complexes are diluted.

J1.16.2. The kit of embodiment J1.16 or J1.16.1, wherein the one or more reagents that tag by attaching compartment-specific molecular barcodes comprise reagents for primer extension polymerization (PEP), reagents for ligation or a transposase comprising a barcoded oligonucleotide.

J1.17. The kit of any one of embodiments J1 to J1.8, wherein one or more reagents that preserve spatial-proximal contiguity information comprise a Tn5 tetramer.

J1.17.1. The kit of embodiment J1.17, wherein the Tn5 tetramer comprises a biotinylated linker sequence.

J1.18. The kit of any one of embodiments J1 to J1.17.1, comprising a pathology slide.

J1.19. The kit of any one of embodiments J1 to J1.18, comprising a bisulfite reagent.

J2. A kit comprising:
  a dewaxing reagent;
  a denaturing detergent; and
  one or more reagents that preserve spatial-proximal contiguity information.

J2.1. The kit of embodiment J2, wherein the dewaxing reagent is xylene or mineral oil.

J2.2. The kit of embodiment J2 or J2.1, wherein the denaturing detergent is sodium dodecyl sulfate (SDS).

J2.3. The kit of any one of embodiments J2 to J2.2, comprising a reagent to quench the denaturing detergent.

J2.4. The kit of embodiment J2.3, wherein the reagent is TritonX-100.

J2.5. The kit of embodiment of any one of embodiments J2 to J2.4, comprising an extracellular matrix protease.

J2.6. The kit of embodiment J2.5, wherein the protease is a collagenase and/or a dispase.

J2.7. The kit of embodiment J2.6, wherein the collagenase is ColI, ColIII or ColIV, and the dispase is Dispase I.

J2.8. The kit of any one of embodiments J2 to J2.7, wherein one or more reagents that preserve spatial-proximal contiguity information comprise reagents that generate proximity ligated nucleic acid molecules.

J2.8.1. The kit of embodiment J2.8, wherein the reagents that generate proximity ligated nucleic acid molecules comprise one or more of the following reagents: at least one restriction endonuclease, a DNA polymerase, a plurality of nucleotides comprising at least one biotinylated nucleotide, and a ligase.

J2.8.2. The kit of embodiment J2.8.1, comprising two restriction endonucleases.

J2.9. The kit of any one of embodiments J2 to J2.7, wherein one or more reagents that preserve spatial-proximal contiguity information comprise solid phase elements.

J2.9.1. The kit of embodiment J2.9, wherein the solid phase elements are beads.

J2.10. The kit of embodiment J2.9 or J2.9.1, wherein the solid phase elements are solid phase substrates functionalized with a nucleic acid crosslinking reagent.

J2.11. The kit of embodiment J2.10, wherein the crosslinking reagent is psoralen.

J2.12. The kit of embodiment J2.9 or J2.9.1, wherein the solid phase elements are solid phase substrates functionalized with an affinity purification molecule.

J2.12.1. The kit of embodiment J2.12, wherein the affinity purification molecule is streptavidin.

J2.12.2. The kit of embodiment J2.12 or J2.12.1, comprising an affinity purification marker.

J2.12.3. The kit of embodiment J2.12.2, wherein the affinity purification marker is biotin.

J2.13. The kit of embodiment J2.9 or J2.9.1, wherein the solid phase elements are solid phase substrates functionalized with a transposase comprising a barcoded oligonucleotide.

J2.14. The kit of embodiment J2.13, wherein the transposase is Tn5.

J2.15. The kit of any one of embodiments J2 to J2.7, wherein one or more reagents that preserve spatial-proximal contiguity information comprise compartment-specific molecular barcodes, reagents that tag by attaching compartment-specific molecular barcodes and/or reagents that compartmentalize.

J2.15.1. The kit of embodiment J2.15, wherein the one or more reagents that compartmentalize comprise a microfluidic compartmentalization device that produces microfluidic droplets or microtiter plate wells into which complexes are diluted.

J2.15.2. The kit of embodiment J2.15. or J2.15.1, wherein the one or more reagents that tag by attaching compartment-specific molecular barcodes comprise reagents for primer extension polymerization (PEP), reagents for ligation or a transposase comprising a barcoded oligonucleotide.

J2.16. The kit of any one of embodiments J2 to J2.7, wherein one or more reagents that preserve spatial-proximal contiguity information comprise a Tn5 tetramer.

J2.16.1. The kit of embodiment J2.16, wherein the Tn5 tetramer comprises a biotinylated linker sequence.

J2.17. The kit of any one of embodiments J2 to J2.16.1, comprising a pathology slide.

J2.18. The kit of any one of embodiments J2 to J2.17, comprising a bisulfite reagent.

J3. A kit comprising:
 a lysis buffer;
 a denaturing detergent; and
 one or more reagents that preserve spatial-proximal contiguity information.

J3.1. The kit of embodiment J3, wherein the lysis buffer comprises one or more salts, a protease inhibitor and a non-ionic, non-denaturing detergent.

J3.2. The kit of embodiment J3 or J3.1, comprising a reagent to quench the denaturing detergent.

J3.3. The kit of embodiment J3.2, wherein the reagent is TritonX-100.

J3.4. The kit of any one of embodiments J3 to J3.3, wherein one or more reagents that preserve spatial-proximal contiguity information comprise reagents that generate proximity ligated nucleic acid molecules.

J3.5. The kit of embodiment J3.4, wherein the reagents that generate proximity ligated nucleic acid molecules comprise one or more of the following reagents: at least one restriction endonuclease, a DNA polymerase, a plurality of nucleotides comprising at least one biotinylated nucleotide, and a ligase.

J3.5.1. The kit of embodiment J3.5, comprising two restriction endonucleases.

J3.6. The kit of any one of embodiments J3 to J3.3, wherein one or more reagents that preserve spatial-proximal contiguity information comprise solid phase elements.

J3.6.1. The kit of embodiment J3.6, wherein the solid phase elements are beads.

J3.7. The kit of embodiment J3.6 or J3.6.1, wherein the solid phase elements are solid phase substrates functionalized with a nucleic acid crosslinking reagent.

J3.8. The kit of embodiment J3.7, wherein the crosslinking reagent is psoralen.

J3.9. The kit of embodiment J3.6 or J3.6.1, wherein the solid phase elements are solid phase substrates functionalized with an affinity purification molecule.

J3.9.1. The kit of embodiment J3.9, wherein the affinity purification molecule is streptavidin.

J3.9.2. The kit of embodiment J3.9 or J3.9.1, comprising an affinity purification marker.

J3.9.3. The kit of embodiment J3.9.2, wherein the affinity purification marker is biotin.

J3.10. The kit of embodiment J3.6 or J3.6.1, wherein the solid phase elements are solid phase substrates functionalized with a transposase comprising a molecular barcoded oligonucleotide.

J3.11. The kit of embodiment J3.10, wherein the transposase is Tn5.

J3.12. The kit of any one of embodiments J3 to J3.3, wherein one or more reagents that preserve spatial-proximal contiguity information comprise compartment-specific molecular barcodes, reagents that tag by attaching compartment-specific molecular barcodes and/or reagents that compartmentalize.

J3.12.1. The kit of embodiment J3.12, wherein the one or more reagents that compartmentalize comprise a microfluidic compartmentalization device that produces microfluidic droplets or microtiter plate wells into which complexes are diluted.

J3.12.2. The kit of embodiment J3.12 or J3.12.1, wherein the one or more reagents that tag by attaching compartment-specific molecular barcodes comprise reagents for primer extension polymerization (PEP), reagents for ligation or a transposase comprising a barcoded oligonucleotide.

J3.13. The kit of any one of embodiments J3 to J3.3, wherein one or more reagents that preserve spatial-proximal contiguity information comprise a Tn5 tetramer.

J3.13.1. The kit of embodiment J3.13, wherein the Tn5 tetramer comprises a biotinylated linker sequence.

J3.14. The kit of any one of embodiments J3 to J3.13.1, comprising a pathology slide.

J3.15. The kit of any one of embodiments J3 to J3.14, comprising a bisulfite reagent.

J3.16. The kit of embodiment of any one of embodiments J3 to J3.15, comprising an extracellular matrix protease.

J3.17. The kit of embodiment J3.16, wherein the protease is a collagenase and/or a dispase.

J3.18. The kit of embodiment J3.17, wherein the collagenase is ColI, ColIII or ColIV, and the dispase is Dispase I.

J4. A kit comprising:
 a denaturing detergent; and
 one or more reagents that preserve spatial-proximal contiguity information.

J4.1. The kit of embodiment J4, wherein the denaturing detergent is sodium dodeccyl sulfate (SDS).

J4.2. The kit of embodiment J4 or J4.1, comprising a reagent to quench the denaturing detergent.

J4.3. The kit of embodiment J4.2, wherein the reagent is TritonX-100.

J4.4. The kit of any one of embodiments J4 to J4.3, wherein one or more reagents that preserve spatial-proximal contiguity information comprise reagents that generate proximity ligated nucleic acid molecules.

J4.5. The kit of embodiment J4.4, wherein the reagents that generate proximity ligated nucleic acid molecules comprise one or more of the following reagents: at least one restriction endonuclease, a DNA polymerase, a plurality of nucleotides comprising at least one biotinylated nucleotide, and a ligase.

J4.5.1. The kit of embodiment J4.5, comprising two restriction endonucleases.

J4.6. The kit of any one of embodiments J4 to J4.3, wherein one or more reagents that preserve spatial-proximal contiguity information comprise solid phase elements.

J4.7. The kit of embodiment J4.6, wherein the solid phase elements are beads.

J4.8. The kit of embodiment J4.6 or J4.7, wherein the solid phase elements are solid phase substrates functionalized with a nucleic acid crosslinking reagent.

J4.9. The kit of embodiment J4.8, wherein the crosslinking reagent is psoralen.

J4.10. The kit of embodiment J4.6 or J4.7, wherein the solid phase elements are solid phase substrates functionalized with an affinity purification molecule.

J4.10.1. The kit of embodiment J4.10, wherein the affinity purification molecule is streptavidin J4.10.2. The kit of embodiment J4.10 or J4.10.1, comprising an affinity purification marker.

J4.10.3. The kit of embodiment J4.10.2, wherein the affinity purification marker is biotin.

J4.11. The kit of embodiment J4.6 or J4.7, wherein the solid phase elements are solid phase substrates functionalized with a transposase comprising a barcoded oligonucleotide.

J4.12. The kit of embodiment J4.11, wherein the transposase is Tn5.

J4.13. The kit of any one of embodiments J4 to J4.3, wherein one or more reagents that preserve spatial-proximal contiguity information comprise compartment-specific molecular barcodes, reagents that tag by attaching compartment-specific molecular barcodes and/or reagents that compartmentalize.

J4.13.1. The kit of embodiment J4.13, wherein the one or more reagents that compartmentalize comprise a microfluidic compartmentalization device that produces microfluidic droplets or microtiter plate wells into which complexes are diluted.

J4.13.2. The method of embodiment J4.13 or J4.13.1, wherein the one or more reagents that tag by attaching compartment-specific molecular barcodes comprise reagents for primer extension polymerization (PEP), reagents for ligation or a transposase comprising a barcoded oligonucleotide.

J4.13.3. The kit of any one of embodiments J4.13 to J4.13.2, further comprising one or more reagents that affinity purify native spatially proximal nucleic acid molecules.

J4.14. The kit of any one of embodiments J4 to J4.3, wherein one or more reagents that preserve spatial-proximal contiguity information comprise a Tn5 tetramer.

J4.14.1. The kit of embodiment J4.14, wherein the Tn5 tetramer comprises a biotinylated linker sequence.

J4.15. The kit of any one of embodiments J4 to J4.14.1, comprising a pathology slide.

J4.16. The kit of any one of embodiments J4 to J4.15, comprising a bisulfite reagent.

J4.17. The kit of embodiment of any one of embodiments J4 to J4.16, comprising an extracellular matrix protease.

J4.18. The kit of embodiment J4.17, wherein the protease is a collagenase and/or a dispase.

J4.19. The kit of embodiment J4.18, wherein the collagenase is ColI, ColIII or ColIV, and the dispase is Dispase I.

J5. A kit comprising:
 a solid phase; and
 one or more reagents that preserve spatial-proximal contiguity information.

J5.1. The kit of embodiment J5, wherein the solid phase comprises a carboxylated surface.

J5.2. The kit of embodiment J5.1, wherein the solid phase comprises a microplate or a bead.

J5.3. The kit of embodiment J5, wherein the solid phase is coated with a cross-linking reagent.

J5.4. The kit of embodiment J5.3, wherein the cross-linking reagent is psoralen.

J5.5. The kit of embodiment J5.3 or 15.4, wherein the solid phase is a magnetic bead.

J5.6. The kit of any one of embodiments J5 to J5.2, wherein one or more reagents that preserve spatial-proximal contiguity information comprise reagents that generate proximity ligated nucleic acid molecules.

J5.7. The kit of embodiment J5.6, wherein the reagents that generate proximity ligated nucleic acid molecules comprise one or more of the following reagents: a restriction endonuclease, a DNA polymerase, a plurality of nucleotides comprising at least one biotinylated nucleotide, and a ligase.

J5.8. The kit of any one of embodiments J5 to J5.5, wherein the one or more reagents that preserve spatial-proximal contiguity information comprise a Tn5 tetramer.

J5.9. The kit of embodiment J5.8, wherein the Tn5 tetramer comprises a biotinylated linker sequence.

J5.10. The kit of any one of embodiments J5 to J5.4 wherein one or more reagents that preserve spatial-proximal contiguity information comprise compartment-specific molecular barcodes, reagents that tag by attaching compartment-specific molecular barcodes and/or reagents that compartmentalize.

J5.11. The kit of embodiment J5.10, wherein the one or more reagents that compartmentalize comprise a microfluidic compartmentalization device that produces microfluidic droplets or microtiter plate wells into which complexes are diluted.

J5.11.1. The kit of embodiment J5.10 or J5.11, wherein the one or more reagents that tag with a compartment specific molecular barcode comprise reagents for primer extension polymerization (PEP), reagents for ligation or a transposase comprising a barcoded oligonucleotide.

J5.11.2. The kit of any one of embodiments J5.10 to J5.11.1, further comprising one or more reagents that affinity purify native spatially proximal nucleic acid molecules.

J5.12. The kit of any one of embodiments J5 to J5.2, wherein one or more reagents that preserve spatial-proximal contiguity information comprise a transposome comprising a compartment-specific barcoded oligonucleotide and the transposome comprising a compartment-specific barcoded oligonucleotide is linked to a solid phase element.

J5.13. The kit of embodiment J15.12, wherein the transposome is Tn5.

J5.14. The kit of any one of embodiments J5 to J5.13, comprising a bisulfite reagent.

K1. A method for reversing crosslinking in a sample crosslinked to preserve spatial-proximal contiguity information, wherein crosslinking is reversed by contacting the sample with proteinase K at a temperature of less than 68° C. for about 30 minutes.

K2. The method of embodiment K1, wherein the temperature is about 55° C.

K3. The method of embodiment K2, wherein the temperature is 55° C.

L1. A method for reversing crosslinking in a sample crosslinked to preserve spatial-proximal contiguity information, wherein crosslinking is reversed by incubating the sample at a temperature of about 95° C. for about 1 hour in the absence of proteinase K.

L2. The method of embodiment L1, wherein crosslinking is reversed by incubating the sample at a temperature of 95° C. for 1 hour in the absence of proteinase K.

M1. A method for preparing nucleic acids from a formalin-fixed paraffin-embedded (FFPE) sample of cells, that preserves spatial-proximal contiguity information, comprising:
   a) providing a formalin-fixed paraffin-embedded sample of cells;
   b) de-waxing the sample to produce a de-waxed sample;
   c) rehydrating the de-waxed sample, thereby generating a de-waxed/rehydrated sample;
   d) contacting the de-waxed/rehydrated sample with lysis buffer; thereby generating a lysed sample;
   e) contacting the lysed sample; with a denaturing detergent at a temperature of about 62° C. for greater than 10 minutes, thereby generating a solubilized and decompacted sample; and
   f) contacting the solubilized and decompacted sample with one or more reagents that preserve spatial-proximal contiguity information in the nucleic acids of the solubilized and decompacted sample.

M1.1. The method of embodiment M1, wherein the temperature is 62° C.

M2. The method of embodiment M1 or M1.1, wherein contact with the denaturing detergent is 15 to 80 minutes.

M3. The method of embodiment M2, wherein contact with the denaturing detergent is 30 to 50 minutes M4. The method of embodiment M3, wherein contact with the denaturing detergent about 40 minutes.

M5. The method of embodiment M4, wherein contact with the denaturing detergent is 40 minutes.

M6. The method of any one of embodiments M1 to M5, wherein the detergent is sodium dodecyl sulfate (SDS).

M7. The method of any one of embodiments M1 to M6, wherein one or more reagents that preserve spatial-proximal contiguity information comprise reagents that generate proximity ligated nucleic acid molecules.

M8. The method of embodiment M7, wherein the reagents that generate proximity ligated nucleic acid molecules comprise one or more of the following reagents: at least one restriction endonuclease, a DNA polymerase, a plurality of nucleotides comprising at least one biotinylated nucleotide, and a ligase.

M9. The method of embodiment M8, comprising two restriction endonucleases.

M10. The method of any one of embodiments M7 to M9, wherein the proximity ligated nucleic acid molecules are generated in situ.

M11. The method of any one of embodiments M1 to M6, wherein one or more reagents that preserve spatial-proximal contiguity information comprise solid phase elements that form complexes with the spatially proximal nucleic acid of the solubilized and decompacted sample to generate spatially proximal nucleic acid of the solubilized and decompacted sample complexed to solid phase elements.

M12. The method of any one of embodiments M1 to M6, wherein one or more reagents that preserve spatial-proximal contiguity information comprise reagents that compartmentalize and tag by attaching compartment-specific molecular barcodes to the nucleic acids of the solubilized and decompacted sample.

M13. The method of any one of embodiments M1 to M6, wherein one or more reagents that preserve spatial-proximal contiguity information comprise a Tn5 tetramer.

M14. The method of any one of embodiments M1 to M13, wherein step (f) generates nucleic acids with preserved spatial-proximal contiguity information and the nucleic acids with preserved spatial-proximal contiguity information are sequenced to produce sequence readouts.

M15. The method of any one of embodiments M1 to M14, wherein the dewaxing/rehydration of the sample is omitted.

N1. A method for preparing nucleic acids from a formalin-fixed paraffin-embedded (FFPE) sample of cells, that preserves spatial-proximal contiguity information, comprising:
   a) providing a formalin-fixed paraffin-embedded sample of cells;
   b) de-waxing the sample to produce a de-waxed sample;
   c) rehydrating the de-waxed sample, thereby generating a de-waxed/rehydrated sample;
   d) contacting the de-waxed/rehydrated sample with a denaturing detergent at a temperature of about 62° C. for greater than 10 minutes, thereby generating a solubilized and decompacted sample; and
   e) contacting the solubilized and decompacted sample with one or more reagents that preserve spatial-proximal contiguity information in the nucleic acids of the solubilized and decompacted sample.

N1.1. The method of embodiment N1, wherein the temperature is 62° C.

N2. The method of embodiment N1 or N1.1, wherein contact with the denaturing detergent is 15 to 80 minutes.

N3. The method of embodiment N2, wherein contact with the denaturing detergent is 30 to 50 minutes N4. The method of embodiment N3, wherein contact with the denaturing detergent about 40 minutes.

N5. The method of embodiment N4, wherein contact with the denaturing detergent is 40 minutes.
N6. The method of any one of embodiments N1 to N5, wherein the detergent is sodium dodecyl sulfate (SDS).
N7. The method of any one of embodiments N1 to N6, wherein one or more reagents that preserve spatial-proximal contiguity information comprise reagents that generate proximity ligated nucleic acid molecules.
N8. The method of embodiment N7, wherein the reagents that generate proximity ligated nucleic acid molecules comprise one or more of the following reagents: at least one restriction endonuclease, a DNA polymerase, a plurality of nucleotides comprising at least one biotinylated nucleotide, and a ligase.
N9. The method of embodiment N8, comprising two restriction endonucleases.
N10. The method of any one of embodiments N7 to N9, wherein the proximity ligated nucleic acid molecules are generated in situ.
N11. The method of any one of embodiments N1 to N6, wherein one or more reagents that preserve spatial-proximal contiguity information comprise solid phase elements that form complexes with the spatially proximal nucleic acid of the solubilized and decompacted sample to generate spatially proximal nucleic acid of the solubilized and decompacted sample complexed to solid phase elements.
N12. The method of any one of embodiments N1 to N6, wherein one or more reagents that preserve spatial-proximal contiguity information comprise reagents that compartmentalize and tag by attaching compartment-specific molecular barcodes to the nucleic acids of the solubilized and decompacted sample.
N13. The method of any one of embodiments N1 to N6, wherein one or more reagents that preserve spatial-proximal contiguity information comprise a Tn5 tetramer.
N14. The method of any one of embodiments N1 to N13, wherein step (e) generates nucleic acids with preserved spatial-proximal contiguity information and the nucleic acids with preserved spatial-proximal contiguity information are sequenced to produce sequence readouts.
N15. The method of any one of embodiments N1 to N14, wherein the dewaxing/rehydration of the sample is omitted.
O1. A method for preparing nucleic acids from a deeply formalin-fixed sample of cells that preserves spatial-proximal contiguity information comprising:
  a) providing a deeply formalin-fixed sample of cells;
  b) contacting the deeply formalin-fixed sample with lysis buffer, thereby generated a lysed sample;
  c) contacting the lysed sample with a denaturing detergent at a temperature of about 62° C. for greater than 10 minutes, thereby generating a solubilized and decompacted sample; and
  d) contacting the solubilized and decompacted sample with one or more reagents that preserve spatial-proximal contiguity information in the nucleic acids of the solubilized and decompacted sample.
O1.1. The method of embodiment O1, wherein the temperature is 62° C.
O2. The method of embodiment O1 or O1.1, wherein contact with the denaturing detergent is 15 to 80 minutes.
O3. The method of embodiment O2, wherein contact with the denaturing detergent is 30 to 50 minutes
O4. The method of embodiment O3, wherein contact with the denaturing detergent about 40 minutes.
O5. The method of embodiment O4, wherein contact with the denaturing detergent is 40 minutes.
O6. The method of any one of embodiments O1 to O5, wherein the detergent is sodium dodecyl sulfate (SDS).
O7. The method of any one of embodiments O1 to O6, wherein one or more reagents that preserve spatial-proximal contiguity information comprise reagents that generate proximity ligated nucleic acid molecules.
O8. The method of embodiment O7, wherein the reagents that generate proximity ligated nucleic acid molecules comprise one or more of the following reagents: at least one restriction endonuclease, a DNA polymerase, a plurality of nucleotides comprising at least one biotinylated nucleotide, and a ligase.
O9. The method of embodiment O8, comprising two restriction endonucleases.
O10. The method of any one of embodiments O7 to O9, wherein the proximity ligated nucleic acid molecules are generated in situ.
O11. The method of any one of embodiments O1 to O6, wherein one or more reagents that preserve spatial-proximal contiguity information comprise solid phase elements that form complexes with the spatially proximal nucleic acid of the solubilized and decompacted sample to generate spatially proximal nucleic acid of the solubilized and decompacted sample complexed to solid phase elements.
O12. The method of any one of embodiments O1 to O6, wherein one or more reagents that preserve spatial-proximal contiguity information comprise reagents that compartmentalize and tag by attaching compartment-specific molecular barcodes to the nucleic acids of the solubilized and decompacted sample.
O13. The method of any one of embodiments O1 to O6, wherein one or more reagents that preserve spatial-proximal contiguity information comprise a Tn5 tetramer.
O14. The method of any one of embodiments O1 to O13, wherein step (d) generates nucleic acids with preserved spatial-proximal contiguity information and the nucleic acids with preserved spatial-proximal contiguity information are sequenced to produce sequence readouts.
P1. A method for preparing nucleic acids from a deeply formalin-fixed sample of cells that preserves spatial-proximal contiguity information comprising:
  a) providing a deeply formalin-fixed sample of cells;
  b) contacting the deeply formalin-fixed sample with a denaturing detergent at a temperature of about 62° C. for greater than 10 minutes, thereby generating a solubilized and decompacted sample; and
  c) contacting the solubilized and decompacted sample with one or more reagents that preserve spatial-proximal contiguity information in the nucleic acids of the solubilized and decompacted sample.
P1.1. The method of embodiment P1, wherein the temperature is 62° C.
P2. The method of embodiment P1 or P1.1, wherein contact with the denaturing detergent is 15 to 80 minutes.
P3. The method of embodiment P2, wherein contact with the denaturing detergent is 30 to 50 minutes
P4. The method of embodiment P3, wherein contact with the denaturing detergent about 40 minutes.
P5. The method of embodiment P4, wherein contact with the denaturing detergent is 40 minutes.
P6. The method of any one of embodiments P1 to P5, wherein the detergent is sodium dodecyl sulfate (SDS).
P7. The method of any one of embodiments P1 to P6, wherein one or more reagents that preserve spatial-proximal contiguity information comprise reagents that generate proximity ligated nucleic acid molecules.

P8. The method of embodiment P7, wherein the reagents that generate proximity ligated nucleic acid molecules comprise one or more of the following reagents: at least one restriction endonuclease, a DNA polymerase, a plurality of nucleotides comprising at least one biotinylated nucleotide, and a ligase.

P9. The method of embodiment P8, comprising two restriction endonucleases.

P10. The method of any one of embodiments P7 to P9, wherein the proximity ligated nucleic acid molecules are generated in situ.

P11. The method of any one of embodiments P1 to P6, wherein one or more reagents that preserve spatial-proximal contiguity information comprise solid phase elements that form complexes with the spatially proximal nucleic acid of the solubilized and decompacted sample to generate spatially proximal nucleic acid of the solubilized and decompacted sample complexed to solid phase elements.

P12. The method of any one of embodiments P1 to P6, wherein one or more reagents that preserve spatial-proximal contiguity information comprise reagents that compartmentalize and tag by attaching compartment-specific molecular barcodes to the nucleic acids of the solubilized and decompacted sample.

P13. The method of any one of embodiments P1 to P6, wherein one or more reagents that preserve spatial-proximal contiguity information comprise a Tn5 tetramer.

P14. The method of any one of embodiments P1 to P13, wherein step (c) generates nucleic acids with preserved spatial-proximal contiguity information and the nucleic acids with preserved spatial-proximal contiguity information are sequenced to produce sequence readouts.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents. Their citation is not an indication of a search for relevant disclosures. All statements regarding the date(s) or contents of the documents is based on available information and is not an admission as to their accuracy or correctness.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claim(s) that follow(s).

What is claimed:

1. A method for preparing nucleic acids from a formalin-fixed paraffin-embedded (FFPE) sample, that preserves spatial-proximal contiguity information, comprising:
    a) providing a formalin-fixed paraffin-embedded sample comprising crosslinked nucleic acid molecules;
    b) de-waxing the sample to produce a de-waxed sample;
    c) rehydrating the de-waxed sample, thereby generating a de-waxed/rehydrated sample;
    d) contacting the de-waxed/rehydrated sample with lysis buffer, thereby generating a lysed sample;
    e) contacting the lysed sample with a denaturing detergent at a temperature greater than 65° C. and less than 80° C., thereby generating a solubilized and decompacted sample; and
    f) generating proximity ligated nucleic acid molecules, thereby preserving spatial-proximal contiguity information in the nucleic acids of the solubilized and decompacted sample.

2. The method of claim 1, wherein the formalin-fixed paraffin-embedded (FFPE) sample is a tissue sample.

3. The method of claim 1, wherein the de-waxed/rehydrated sample is contacted with an extracellular matrix protease prior to contact with lysis buffer.

4. The method of claim 1, wherein the temperature is 74° C.

5. The method of claim 1, wherein contact with the denaturing detergent is 15 to 80 minutes.

6. The method of claim 5, wherein contact with the denaturing detergent is 40 minutes.

7. The method of claim 1, wherein the detergent is sodium dodecyl sulfate (SDS).

8. The method of claim 1, wherein the formalin-fixed paraffin-embedded sample is provided as a tissue section of about 5 um to about 10 um in thickness.

9. The method of claim 1, wherein the nucleic acids with preserved spatial-proximal contiguity information prepared from the sample are sequenced and produce >40% of mapped de-duplicated reads representing long-range readouts.

10. The method of claim 1, wherein the proximity ligated nucleic acid molecules are generated in situ.

11. The method of claim 9, wherein the long-range readouts are utilized for identification of genomic variants, to inform genome assemblies de novo, for deconvolution of haplotype phase information and/or for genomic rearrangement detection.

12. The method of claim 1, wherein the solubilized and decompacted sample generated in (e) comprises crosslinked nucleic acid molecules.

\* \* \* \* \*